(12) United States Patent
Czech et al.

(10) Patent No.: US 12,031,161 B2
(45) Date of Patent: Jul. 9, 2024

(54) TARGETING Nrip1 TO ALLEVIATE METABOLIC DISEASE

(71) Applicant: University of Massachusetts, Boston, MA (US)

(72) Inventors: Michael P. Czech, Westborough, MA (US); Emmanouela Tsagkaraki, Worcester, MA (US); Sarah M. Nicoloro, Holden, MA (US); Silvia Corvera, Westborough, MA (US)

(73) Assignee: University of Massachusetts, Boston, MA (US)

( * ) Notice: Subject to any disclaimer, the term of this patent is extended or adjusted under 35 U.S.C. 154(b) by 11 days.

(21) Appl. No.: 17/497,367

(22) Filed: Oct. 8, 2021

(65) Prior Publication Data

US 2022/0220461 A1 Jul. 14, 2022

Related U.S. Application Data

(60) Provisional application No. 63/089,955, filed on Oct. 9, 2020.

(51) Int. Cl.
*C12N 9/22* (2006.01)
*A61K 35/35* (2015.01)
*A61P 3/04* (2006.01)
*C12N 5/077* (2010.01)
*C12N 15/11* (2006.01)
*C12N 15/90* (2006.01)

(52) U.S. Cl.
CPC .............. *C12N 9/22* (2013.01); *A61K 35/35* (2013.01); *A61P 3/04* (2018.01); *C12N 5/0653* (2013.01); *C12N 15/11* (2013.01); *C12N 15/907* (2013.01); *C12N 2310/20* (2017.05); *C12N 2506/13* (2013.01); *C12N 2510/00* (2013.01); *C12N 2800/80* (2013.01)

(58) Field of Classification Search
CPC ........ C12N 9/22; C12N 5/0653; C12N 15/11; C12N 15/907; C12N 2310/20; C12N 2506/13; C12N 2510/00; C12N 2800/80; A61P 3/04; A61K 35/35
See application file for complete search history.

(56) References Cited

U.S. PATENT DOCUMENTS

| | | | |
|---|---|---|---|
| 6,103,496 A | 8/2000 | Brash et al. | |
| 6,346,374 B1 | 2/2002 | Tartglia et al. | |
| 6,551,809 B2 | 4/2003 | Yan et al. | |
| 8,093,223 B2 | 1/2012 | Czech et al. | |
| 11,519,009 B2 * | 12/2022 | Czech .................... | C12N 9/22 |
| 2002/0119499 A1 | 8/2002 | Taniguchi et al. | |
| 2003/0153519 A1 | 8/2003 | Kay et al. | |
| 2004/0198682 A1 | 10/2004 | McSwiggen et al. | |
| 2015/0259647 A1 | 9/2015 | Corvera | |
| 2015/0291966 A1 | 10/2015 | Zhang et al. | |
| 2021/0095251 A1 | 4/2021 | Corvera | |

FOREIGN PATENT DOCUMENTS

| | | | |
|---|---|---|---|
| WO | WO 2002/033046 | 4/2002 | |
| WO | WO 2005/083127 | 9/2002 | |
| WO | WO 2002/103361 | 12/2002 | |
| WO | WO 2004/053103 | 6/2004 | |
| WO | WO 2013/025763 | 2/2013 | |
| WO | WO 2015/048577 | 4/2015 | |
| WO | WO-2018129440 A1 * | 7/2018 | ......... A01K 67/0278 |
| WO | WO-2019010384 A1 * | 1/2019 | ......... C12N 15/1089 |

OTHER PUBLICATIONS

Sequence ID: NM_001358238.1, Mus musculus nuclear receptor interacting protein 1 (Nrip1), transcript variant 2, mRNA, first published 1998, pp. 1-9 (Year: 1998).*
Alignment documentation. attached as an NPL, p. 1-5. (Year: 2023).*
Aagaard et al., "RNAi therapeutics: principles, prospects and challenges," Advanced Drug Delivery Reviews, Mar. 30, 2007, 59(2-3):75-86.
Agarwal et al., "AGPAT2 is mutated in congenital generalized lipodystrophy linked to chromosome 9q34," Nature Genetics, Apr. 22, 2002, 31(1):21-3.
Aitman et al., "Identification of Cd36 (Fat) as an insulin-resistance gene causing defective fatty acid and glucose metabolism in hypertensive rats," Nature Genetics, Jan. 1999, 21(1):76-83.
Alizadeh et al., "The lymphochip: a specialized cDNA microarray for the genomic-scale analysis of gene expression in normal and malignant lymphocytes," Cold Spring Harbor Symposia on Quantitative Biology, Jan. 1, 1999, 64:71-78.
Aranda et al., "Nuclear Hormone Receptors and Gene Expression," Physiological Reviews, Jul. 1, 2001, 81(3):1269-304.
Arner et al., "Adipocyte turnover: relevance to human adipose tissue morphology," Diabetes, Jan. 1, 2010, 59(1):105-9.
AU Office Action in Australian Appln. No. 2005311684, dated Feb. 16, 2011, 3 pages.
Baatout et al., "Matrigel: a useful tool to study endothelial differentiation," Romanian Journal of Internal Medicine= Revue Roumaine de Medecine Interne, 1996, 34(3-4):263-9.
Baer et al., "Adipose-derived mesenchymal stromal/stem cells: tissue localization, characterization, and heterogeneity," Stem Cells International, Jan. 12, 2012, 2012, 12 pages.
Bass, "The short answer," Nature, May 2001, 411(6836):428-9.
Benton et al., "Advancing science and technology via 3D culture on basement membrane matrix," Journal of Cellular Physiology, Oct. 2009, 221(1):18-25.
Bernal-Mizrachi et al., "Dexamethasone induction of hypertension and diabetes is PPAR-α dependent in LDL receptor-null mice," Nature Medicine, Aug. 2003, 9(8):1069-75.

(Continued)

*Primary Examiner* — Arthur S Leonard
*Assistant Examiner* — Jianjian Zhu
(74) *Attorney, Agent, or Firm* — Fish & Richardson P.C.

(57) ABSTRACT

Provided herein are methods and compositions for disrupting expression of nuclear receptor interacting protein 1 (Nrip1) in adipose cells, and methods of use of such adipose cells for treating, or reducing risk of, a condition associated with an elevated body mass index (BMI).

10 Claims, 50 Drawing Sheets

Figure 1A:
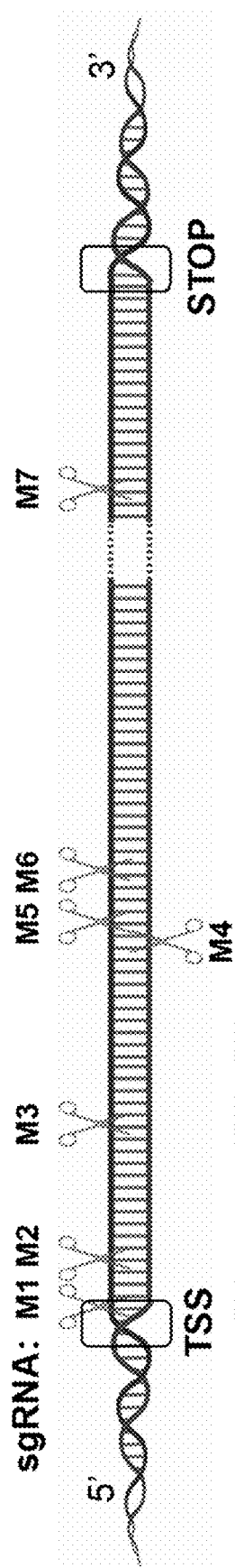

Specification includes a Sequence Listing.

(56) References Cited

OTHER PUBLICATIONS

Bernlohr et al., "Expression of specific mRNAs during adipose differentiation: identification of an mRNA encoding a homologue of myelin P2 protein," Proceedings of the National Academy of Sciences, Sep. 1984, 81(17):5468-72.
Besset et al., "The Identification and Characterization of Expression of Pftaire-1, a Novel Cdk Family Member, Suggest Its Function in the Mouse Testis and Nervous System," Molecular Reproduction and Development: Incorporating Gamete Research, May 1998, 50(1):18-29.
Bjorkman et al. "Genomic Structure of PEX13, a Candidate Peroxisome Biogenesis Disorder Gene," Genomics, Dec. 15, 1998, 54(3):521-8.
Blumenfeld et al., "A direct tissue-grafting approach to increasing endogenous brown fat," Scientific Reports, May 21, 2018, 8(1):1-2.7957, 12 pages.
Bork et al., "Go hunting in sequence databases but watch out for the traps," Trends in Genetics, Oct. 1, 1996, 12(10):425-7.
Bork, "Powers and pitfalls in sequence analysis: the 70% hurdle," Genome Research, Apr. 1, 2000, 10(4):398-400.
Brenner, "Errors in genome annotation," Trends in Genetics, Apr. 1, 1999, 15(4):132-3.
Brown et al., "Effects of metreleptin in pediatric patients with lipodystrophy," The Journal of Clinical Endocrinology & Metabolism, May 1, 2017, 102(5):1511-9.
Cain et al., "Members of the VAMP Family of Synaptic Vesicle Proteins Are Components of Glucose Transporter-containing Vesicles from Rat Adipocytes," Journal of Biological Chemistry, Jun. 15, 1992, 267(17):11681-4.
Caldas et al., "NSDHL, an enzyme involved in cholesterol biosynthesis, traffics through the Golgi and accumulates on ER membranes and on the surface of lipid droplets," Human Molecular Genetics, Nov. 15, 2003, 12(22):2981-91.
Ceddia et al., "A compendium of G-protein-coupled receptors and cyclic nucleotide regulation of adipose tissue metabolism and energy expenditure," Clinical Science, Mar. 2020, 134(5):473-512.
Chen et al., "Nrg4 promotes fuel oxidation and a healthy adipokine profile to ameliorate diet-induced metabolic disorders," Molecular Metabolism, Aug. 1, 2017, 6(8):863-72.
Chinnadurai, "CtBP family proteins: more than transcriptional corepressors," Bioessays, Jan. 2003, 25(1):9-12.
Christian et al., "Characterization of four autonomous repression domains in the corepressor receptor interacting protein 140," Journal of Biological Chemistry, Apr. 9, 2004, 279(15):15645-51.
Chung et al., "Targeted delivery of CRISPR interference system against Fabp4 to white adipocytes ameliorates obesity, inflammation, hepatic steatosis, and insulin resistance," Genome Research, Sep. 1, 2019, 29(9):1442-52.
Corvera, "CRISPR-Based Gene Editing to Induce Thermogenic Adipose Tissue in Type 2 Diabetes," University of Massachusetts School, Aug. 1, 2019, 26 pages.
Czech et al., "Signaling Mechanisms That Regulate Glucose Transport" Journal of Biological Chemistry, Jan. 22, 1999, 274(4):1865-8.
Czech, "Insulin action and resistance in obesity and type 2 diabetes," Nature Medicine, Jul. 2017, 23(7):804-14.
Danesch et al., "Cloning and Transcriptional Regulation of a Novel Adipocyte-specific Gene, FSP27," Journal of Biological Chemistry, Apr. 5, 1992, 267(10):7185-93.
Davignon et al., "Gene Structure of MurineGna11andGna15: Tandemly Duplicated Gq Class G Protein α Subunit Genes," Genomics, Feb. 1, 1996, 31(3):359-66.
DiGirolamo et al., "Metabolic patterns and insulin responsiveness of enlarging fat cells," Journal of Lipid Research, vol. 15:332-338 (1974).
Doerks et al., Protein annotation: detective work for function prediction, 1998, Trends in Genetics, vol. 14, pp. 248-250.
Elmendorf et al., "Insulin Signaling Regulating the Trafficking and Plasma Membrane Fusion of GLUT4-Containing Intracellular Vesicles" Exp. Cell Res. 253:55-62 (1999).
Enari et al., "A caspase-activated DNase that degrades DNA during apoptosis, and its inhibitor ICAD," Nature, vol. 391:43-50 (1998).
EP European Search Report in European Appln. No. 18844019.2, dated Mar. 23, 2021, 10 pages.
EP European Search Report, Application No. 05852901.7, dated May 4, 2009.
EP Supplemental European Search Report in EP Application No. 01987792, dated Jun. 18, 2009, received from the European Patent Office (7 pages).
Escobedo-Lucea et al., "A xenogeneic-free protocol for isolation and expansion of human adipose stem cells for clinical uses," PloS one, Jul. 9, 2013, 8(7):e67870, 12 pages.
Farooqui et al., "Effects of Retinoid Ligands on RIP140: Molecular Interaction with Retinoid Receptors and Biological Activity," Biochemistry, vol. 42:971-979 (2003).
Friedman et al., "Mechanisms of NAFLD development and therapeutic strategies," Nature Medicine, Jul. 2018, 24(7):908-22.
Frost et al., "Evidence for the Involvement of Vicinal Sulfhydryl Groups in Insulin-activated Hexose Transport by 3T3-L1 Adipocytes," The Journal of Biological Chemistry, vol. 260:2646-2652 (1985).
Funcke et al., "Beyond adiponectin and leptin: adipose tissue-derived mediators of inter-organ communication," Journal of Lipid Research, Oct. 1, 2019, 60(10):1648, 117 pages.
Gao et al., "Expression of seipin in adipose tissue rescues lipodystrophy, hepatic steatosis and insulin resistance in seipin null mice," Biochemical and Biophysical Research Communications, May 1, 2015, 460(2):143-50.
Garg, "Acquired and inherited lipodystrophies," New England Journal of Medicine, Mar. 18, 2004, 350(12):1220-34.
GenBank Accession No. AB032417, 4 pages (Sep. 14, 1999).
GenBank Accession No. AF180471, 4 pages (Aug. 24, 1999).
GenBank Accession No. AF248484, 51 pages (Apr. 4, 2000).
GenBank Accession No. AK_018652, 5 pages, (Jul. 10, 2000).
GenBank Accession No. AK_078461, 5 pages (Apr. 16, 2002).
GenBank Accession No. AK_129472, 3 pages (Jul. 23, 2003).
GenBank Accession No. AV272221, 3 pages (Nov. 5, 1999).
GenBank Accession No. AY364640, 2 pages (2003).
GenBank Accession No. BC015285, 3 pages (Oct. 1, 2001).
GenBank Accession No. BC023683, 3 pages (Feb. 5, 2002).
GenBank Accession No. BC024811, 3 pages (Mar. 1, 2002).
GenBank Accession No. BC057074, 4 pages (2002).
GenBank Accession No. BC059190, 4 pages (Oct. 1, 2003).
GenBank Accession No. BC063094, 4 pages (Dec. 2, 2003).
GenBank Accession No. M36033, 3 pages (Apr. 11, 1990).
GenBank Accession No. NM_001278, 6 pages (1993).
GenBank Accession No. NM_003489, 5 pages (Mar. 24, 1999).
GenBank Accession No. NM_007700, 6 pages (1995).
GenBank Accession No. NM_008055, 4 pages (1996).
GenBank Accession No. NM_008363, 6 pages (1996).
GenBank Accession No. NM_008696, 8 pages (1997).
GenBank Accession No. NM_008735, 4 pages (Jan. 6, 2000).
GenBank Accession No. NM_008795, 4 pages (1992).
GenBank Accession No. NM_010562, 5 pages (1997).
GenBank Accession No. NM_010941, 4 pages (1975).
GenBank Accession No. NM_011049, 5 pages (1992).
GenBank Accession No. NM_011074, 5 pages (1997).
GenBank Accession No. NM_011517, 4 pages (1997).
GenBank Accession No. NM_016700, 5 pages (1997).
GenBank Accession No. NM_016961, 5 pages (1996).
GenBank Accession No. NM_019730, 3 pages (2000).
GenBank Accession No. NM_022801, 5 pages (1988).
GenBank Accession No. NM_025670, 3 pages (2002).
GenBank Accession No. NM_028385, 6 pages (2001).
GenBank Accession No. NM_053117, 3 pages (2000).
GenBank Accession No. NM_145686, 9 pages (1997).
GenBank Accession No. NM_153694, 4 pages (2000).
GenBank Accession No. NM_173440, 5 pages (Jan. 14, 2003).
GenBank Accession No. NM_178050, 4 pages (1999).
GenBank Accession No. NM_178373, 3 pages (1992).
GenBank Accession No. NM_212502, 6 pages (1992).

(56) References Cited

OTHER PUBLICATIONS

GenBank Accession No. NP_003480, 3 pages (Mar. 24, 1999).
GenBank Accession No. NP_005027, 4 pages (May 14, 1999).
GenBank Accession No. NP_775616, 3 pages (Jan. 14, 2003).
GenBank Accession No. P37231, 13 pages (Oct. 1, 1994).
GenBank Accession No. Q03181, 6 pages (Nov. 18, 2003).
GenBank Accession No. U10115, 3 pages (1992).
GenBank Accession No. X66363, 2 pages (1992).
GenBank Accession No. XM_ 128751, 4 pages (2005).
genenames.org, "Gene Symbol Report: MAP4K4, mitoge-activated protein kinase 4," dated Jun. 2, 2012, retrieved from URL <http://www.genenames.org/data/hgnc_data.php?hgnc_id=6866> on Jun. 2, 2012, 1 page.
Gentleman et al., "Bioconductor: open software development for computational biology and bioinformatics," Genome Biology, vol. 5:R80 (2004).
Graeser et al., "Regulation of the CDK-related protein kinase PCTAIRE-1 and its possible role in neurite outgrowth in Neuro-2A cells," Journal of Cell Science, vol. 115:3479-3490 (2002).
Guilherme et al., "Adipocyte dysfunctions linking obesity to insulin resistance and type 2 diabetes," Nature Reviews Molecular Cell Biology, May 2008, 9(5):367-77.
Guilherme et al., "EHD2 and the Novel EH Domain Binding Protein EHBP1 Couple Endocytosis to the Actin Cytoskeleton," The Journal of Biological Chemistry, vol. 279:10593-10605 (2004).
Han et al., "The spatiotemporal development of adipose tissue," Development, Nov. 15, 2011, 138(22):5027-37.
Hart et al., "The estrogen receptor: more than the average transcription factor," Biochemistry and Cell Biology, vol. 80-335-341 (2002).
Hassan et al., "Promoter Targeting of Chromatin-Modifying Complexes," Frontiers in Bioscience., vol. 6:d1054-1064 (2001).
Heery et al., "A signature motif in transcriptional co-activators mediates binding to nuclear receptors," Nature, vol. 387:733:-736 (1997).
Heller-Harrison et al., "Insulin-mediated Targeting of Phosphatidylinositol 3-Kinase to GLUT4-containing Vesicles (*)," Journal of Biological Chemistry, Apr. 26, 1996, 271(17):10200-4.
Hotamisligil et al., "Increased Adipose Tissue Expression of Tumor Necrosis Factor-a in Human Obesity and Insulin Resistance," J. Clin. Invest., vol. 95:2409-2415 (1995).
Hu et al., AdipoQ Is a Novel Adipose-specific Gene Dysregulated in Obesity (*). Journal of Biological Chemistry, May 3, 1996, 271(18):10697-703.
Hu et al., "Suppressive Effect of Receptor-interacting Protein 140 on Coregulator Binding to Retinoic Acid Receptor Complexes, Histone-modifying Enzyme Activity, and Gene Activation," The Journal of Biological Chemistry, vol. 279:319-325 (2004).
Hughes et al., "Matrigel: a complex protein mixture required for optimal growth of cell culture," Proteomics, May 2010, 10(9):1886-90.
Hussain, "Lipodystrophy syndromes," Endocrinology and Metabolism Clinics, Dec. 1, 2016, 45(4):783-97.
Jiang et al., "Insulin signaling through Akt/protein kinase B analyzed by small interfering RNA-mediated gene silencing," PNAS, vol. 100:7569-7574 (2003).
Joberty et al., "The cell-polarity protein Par6 links Par3 and atypical protein kinase C to Cdc42," Nature Cell Biology, vol. 2:531-539 (2000).
Johnson et al., "A Di-Leucine Sequence and a Cluster of Acidic Amino Acids Are for Dynamic Retention in the Endosomal Recycling Compartment of Fibroblasts," Molecular Biology, vol. 12:367-381 (2001).
Johnson et al., "Identification of an Insulin-Responsive, Slow Endocytic Recycling Mechanism in Chinese Hamster Ovary Cells," Journal of Biological Chemistry, Jul. 10, 1998, 273(28):17968-77.
JP Japanese Office Action in Japanese Appln. No. 2007-544576, dated Jul. 13, 2011, 10 pages (with English translation).
Kajimura et al., "Brown and beige fat: physiological roles beyond heat generation," Cell Metabolism, Oct. 6, 2015, 22(4):546-59.
Kamble et al., "Proof-of-concept for CRISPR/Cas9 gene editing in human preadipocytes: Deletion of FKBP5 and PPARG and effects on adipocyte differentiation and metabolism," Scientific Reports, Jun. 29, 2020, 10(1):1-4.
Kandror et al., "Comparison of glucose-transporter-containing vesicles from rat fat and muscle tissues: evidence for a unique endosomal compartment," Biochemical Journal, Apr. 15, 1995, 307(2):383-90.
Kandror et al., "Compartmentalization of protein traffic in insulin-sensitive cells," American Journal of Physiology-Endocrinology and Metabolism, Jul. 1, 1996, 271(1):E1-4.
Kandror et al., "The insulin-like growth factor II/mannose 6-phosphate receptor utilizes the same membrane compartments as GLUT4 for insulin-dependent trafficking to and from the rat adipocyte cell surface," Journal of Biological Chemistry, Sep. 6, 1996, 271(36):21703-8.
Kirikoshi et al., "Molecular Cloning and Characterization of Human Frizzled-4 on Chromosome 11q14-q21," Biochemical and Bio11hysical Research Communication, vol. 264:955-961 (1999).
Kishida et al., "Wnt-3a and Dvl Induce Neurite Retraction by Activating Rho-Associated Kinase," Molecular and Cellular Biology, vol. 24:4487-4501 (2004).
Kleinman et al., "Matrigel: basement membrane matrix with biological activity," Seminars in Cancer Biology, Oct. 1, 2005, 15(5):378-86.
Klepac et al., "The role of brown and beige adipose tissue in glycaemic control," Molecular Aspects of Medicine, Aug. 1, 2019, 68:90-100.
Koh et al., "Peroxisome Proliferator-Activated Receptor {PP AR)-a Activation Prevents Diabetes in OLETF Rats," Diabetes, vol. 52:2331-2337 (2003).
Kolle et al., "CRIMI, a novel gene encoding a cysteine-rich repeat protein, is developmentally regulated and implicated in vertebrate CNS development and organogenesis," Mechanisms of Development, vol. 90:181-193 (2000).
Krylova et al., "Dishevelled-I Regulates Microtubule Stability: A New Function Mediated by Glycogen Synthase Kinase-313," The Journal of Cell Biology, vol. 151:83-93 (2000).
Kusminski et al., "Targeting adipose tissue in the treatment of obesity-associated diabetes," Nature Reviews Drug Discovery, Sep. 2016, 15(9):639-60.
Lampson et al., "Demonstration of insulin-responsive trafficking of GLUT4 and vpTR in fibroblasts," Journal of Cell Science, Nov. 15, 2000, 113(22):4065-76.
Le et al., "Insulin signaling and glucose homeostasis in mice lacking protein tyrosine phosphatase a," Biochemical and Bio12hysical Research Communications, vol. 314:321-329 (2004).
Lee et al., "An integrated view of immunometabolism," Cell, Jan. 11, 2018, 172(1-2):22-40.
Lee et al., "c-Jun N-terminal Kinase (JNK) Mediates Feedback Inhibition of the Insulin Signaling Cascade," The Journal of Biological Chemistry, vol. 278:2896-2902 (2003).
Lee et al., "Cloning and Characterization of Mouse RIP140, a Corepressor for Nuclear Orphan Receptor TR2," Molecular and Cellular BiolofQI, vol. 18:6745-6755 (1998).
Leonardsson et al., "Nuclear receptor corepressor RIP140 regulates fat accumulation," Proceedings of the National Academy of Sciences, Jun. 1, 2004, 101(22):8437-42.
Leung et al., RNA interference: from gene silencing to gene-specific therapeutics, 2005, Pharmacology and Therapeutics, vol. 107, pp. 222-239.
Lewandowski et al., "Familial partial lipodystrophy as differential diagnosis of polycystic ovary syndrome," Endokrynologia Polska, Dec. 31, 2014, 66(6):550-4.
Liang et al., "Molecular cloning and characterization of CIDE-3, a novel member of the cell-death-inducing DNA-fragmentation-factor (DFF45)-like effector family," Biochem J., vol. 370:195-203 (2003).
Liu et al., "PEX 13 is Mutated in Complementation Group 13 of the Peroxisome-Biogenesis Disorders" Am. J. Hum. Genet. 65:621-634, 1999.
Lynes et al., "The cold-induced lipokine 12, 13-diHOME promotes fatty acid transport into brown adipose tissue," Nature Medicine, May 2017, 23(5):631, 9 pages.

(56) References Cited

OTHER PUBLICATIONS

Martin et al., "GLUT4 Trafficking in Insulin-Sensitive Cells" Cell Biochem. Biophys. 30:89-113 (1999).
Martin et al., "The Glucose Transporter (GLUT-4) and Vesicle-associated Membrane Protein-2 (VAMP-2) Are Segregated from Recycling Endosomes in Insulin-sensitive Cells," The Journal of Cell Biology, Aug. 1996, 134(3):625-35.
McCaffrey et al., "RNA interference in adult mice," Nature, Jul. 2002, 418:38-39.
McDonnell et al., "Connections and Regulation of the Human Estrogen Receptor," Science, vol. 296:1642-1644 (2002).
McKenna et al., "ENDO 2003: Malcolm Parker—RIP140 corepressor is a key regulator of ovulation and adipocyte function," NURSA e-Journal, ID# 2.06242003.2 ISSN 1550-7629, vol. 1, 3 pages (2003).
Mercurio et al., "IKK-1 and IKK-2: Cytokine-Activated IKB Kinases Essential for NF-KB Activation," Science, vol. 278:860-866 (1997).
Merlin et al., "Rosiglitazone and a β3-adrenoceptor agonist are both required for functional browning of white adipocytes in culture," Frontiers in Endocrinology, May 30, 2018, 9:249, 17 pages.
Meyerson et al., "A family of human cdc2-related protein kinases," The EMBO Journal, vol. 11:2909-2917 (1992).
Min et al., "Adipsin, the Adipocyte Serine Protease: Gene Structure and Control of Expression by Tumor Necrosis Factor," Nucleic Acids Research, Nov. 11, 1986, 14(22):8879-92.
Min et al., "Human'brite/beige'adipocytes develop from capillary networks, and their implantation improves metabolic homeostasis in mice," Nature Medicine, Mar. 2016, 22(3):312-8.
Miyamoto et al., "Azoospermia in patients heterozygous for a mutation in SYCP3," The Lancet, vol. 362:1714-1719.
Mootha et al., Erm and Gabpa/b specify PGC-1a-dependent oxidative phosphorylation gene expression that is altered in diabetic muscle, PNAS, vol. 101:6570-6575 (2004).
Morrison et al., "Hormonal Signaling and Transcriptional Control of Adipocyte Differentiation," The Journal of Nutrition, vol. 130:3116S-3121S (2000).
Moyersoen et al., "Biogenesis of peroxisomes and glycosomes: trypanosomatid glycosome assembly is a promising new drug target," FEMS Microbiology Reviews, 28(5):603-643 (2004).
Murphy et al., "PPAR-, agonists: therapeutic role in diabetes, inflammation and cancer," Trends in Pharmacological Sciences, vol. 21:469-474 (2000).
Nautiyal et al., "Distinct functions for RIP140 in development, inflammation, and metabolism," Trends in Endocrinology & Metabolism, Sep. 1, 2013, 24(9):451-9.
Nedergaard et al., "The changed metabolic world with human brown adipose tissue: therapeutic visions," Cell Metabolism, Apr. 7, 2010, 11(4):268-72.
Ngo et al., "Computational complexity, protein structure prediction, and the Levinthal paradox," The Protein Folding Problem and Tertiary Structure Prediction, 1994, 433-506.
Nishimura et al., "Adipogenesis in obesity requires close interplay between differentiating adipocytes, stromal cells, and blood vessels," Diabetes, Jun. 1, 2007, 56(6):1517-26.
Nolis, "Exploring the pathophysiology behind the more common genetic and acquired lipodystrophies," Journal of Human Genetics, Jan. 2014, 59(1):16-23.
Nolte et al., "Ligand binding and co-activator assembly of the peroxisome proliferator-activated receptor-gamma," Nature, vol. 395:137-143 (1998).
Ntambi et al., "Differentiation-induced Gene Expression in 3T3-L1 Preadipocytes," The Journal of Biological Chemistry, vol. 263:17291-17300 (1988).
Okuda et al., "PCTAIRE-1 and PCTAIRE-3, two members of a novel cdc2/CDC28-related protein kinase gene family," Oncogene, vol. 7:2249-2258 (1992).
Park et al., "Before they were fat: adipocyte progenitors," Cell Metabolism, Dec. 6, 2008, 8(6):454-7.

PCT International Preliminary Report on Patentability in International Appln. No. PCT/US2005/043817, dated Nov. 4, 2008, 6 pages.
PCT International Preliminary Report on Patentability in International Appln. No. PCT/US2018/046266, dated Feb. 11, 2020, 9 pages.
PCT International Search Report and Written Opinion in International Appln. No. PCT/US2005/043817, dated Oct. 8, 2008, 14 pages.
PCT International Search Report and Written Opinion in International Appln. No. PCT/US2021/054155, dated Apr. 7, 2022, 14 pages.
PCT International Search Report and Written Opinion in International Appln. No. PCT/US2018/046266, dated Oct. 17, 2018, 17 pages.
Petersen et al., "Regulation of hepatic glucose metabolism in health and disease," Nature Reviews Endocrinology, Oct. 2017, 13(10):572-87.
Phan et al., "Lipin Expression Preceding Peroxisome Proliferator-activated Receptor-y Is Critical for Adipogenesis in Vivo and in Vitro," The Journal of Biological Chemistry, vol. 279:29558-29564 (2004).
Powelka et al., "Suppression of oxidative metabolism and mitochondrial biogenesis by the transcriptional corepressor RIP140 in mouse adipocytes," The Journal of Clinical Investigation, Jan. 4, 2006, 116(1):125-36.
Qi et al., "Peroxisome Proliferator-Activated Receptors, Coactivators, and Downstream Targets," Cell Biochemistry and Biophysics, vol. 32:187-204 (2000).
Richard et al., "ABC50, a Novel Human ATP-Binding Cassette Protein Found in Tumor Necrosis Factor-a-Stimulated Synoviocytes," Genomics, vol. 53:137-145 (1998).
Robbins et al., "The genetics of lipid storage and human lipodystrophies," Trends in Molecular Medicine, Jul. 1, 2015, 21(7):433-8.
Robitaille et al., "Mutant frizzled-4 disrupts retinal angiogenesis in familial exudative vitreoretinopathy," Nature Genetics, vol. 32:326-330 (2002).
Roden et al., "The integrative biology of type 2 diabetes," Nature, Dec. 2019, 576(7785):51-60.
Rosenwald et al., "Bi-directional interconversion of brite and white adipocytes," Nature Cell Biology, Jun. 2013, 15(6):659-67.
Ross et al., "Inhibition of Adipogenesis by Wnt Signaling," Science, vol. 289:950-953 (2000).
Sakahira et al., "Cleavage of CAD inhibitor in CAD activation and DNA degradation during apoptosis," Nature, vol. 391:96-99 (1998).
Sakai et al., Integrin-linked kinase (ILK) is required for polarizing the epiblast, cell adhesion, and controlling actin accumulation, Genes & Develo12ment, vol. 17:926-940 (2003).
Savage et al., "Mouse models of inherited lipodystrophy," Disease Models & Mechanisms, Nov. 1, 2009, 2(11-12):554-62.
Shen et al., "CRISPR-delivery particles targeting nuclear receptor-interacting protein 1 (Nrip1) in adipose cells to enhance energy expenditure," Journal of Biological Chemistry, Nov. 2, 2018, 293(44):17291-305.
Skolnick et al., From genes to protein structure and function: novel applications of computational approaches in the genomic era, 2000, Trends in Biotech, vol. 18, Issue 1, pp. 34-39.
Smith et al., The challenge of genome sequence annotation or "the devil is in the details", 1997, Nature Biotechnology, vol. 15, pp. 1222-1223.
Stanford et al., "Brown adipose tissue regulates glucose homeostasis and insulin sensitivity," The Journal of clinical investigation, Dec. 10, 2012, 123(1).:215-23.
Stephens et al., "Tumor Necrosis Factor-a-induced Insulin Resistance in 3T3-L1 Adipocytes Is Accompanied by a Loss of Insulin Receptor Substrate-I and GLUT4 Expression without a Loss of Insulin Receptor-mediated Signal Transduction," The Journal of Biological Chemistry, vol. 272:971-976 (1997).
Su et al., "NIK is a new Ste20-related kinase that binds NCK and MEKK1 and activates the SAPK/JNK cascade via a conserved regulatory domain," The EMBO Journal, vol. 16:1279-1290 (1997).

(56) References Cited

OTHER PUBLICATIONS

Subtil et al., "Characterization of the Insulin-regulated Endocytic Recycling Mechanism in 3T3-L1 Adipocytes Using a Novel Reporter Molecule" J. Biol. Chem. 275:4787-4795 (2000).
Tamori et al., "Role of Peroxisome Proliferator-Activated Receptor-y in Maintenance of the Characteristics of Mature 3T3-L1 Adipocytes," Diabetes, vol. 51:2045-2055 (2002).
Tan et al., "Thermosensitive injectable hyaluronic acid hydrogel for adipose tissue engineering," Biomaterials, Dec. 1, 2009, 30(36):6844, 24 pages.
Tang et al., "An RNA interference-based screen identifies MAP4K4/NIK as a negative regulator of PPARγ, adipogenesis, and insulin-responsive hexose transport," Proceedings of the National Academy of Sciences, Feb. 14, 2006, 103(7):2087-92.
Tang et al., "Thiazolidinediones regulate adipose lineage dynamics," Cell Metabolism, Jul. 6, 2011, 14(1):116-22.
Tang et al., "White fat progenitor cells reside in the adipose vasculature," Science, Oct. 24, 2008, 322(5901):583-6.
Tesz et al., "Tumor necrosis factor α (TNFα) stimulates Map4k4 expression through TNFα receptor 1 signaling to c-Jun and activating transcription factor 2," Journal of Biological Chemistry, Jul. 2007, 282(27):19302-12.
Tran et al. "Human thermogenic adipocyte regulation by the long noncoding RNA LINC00473," Nature Metabolism, May 2020, 2(5):397-412.
Tran et al., "The vascular endothelium of the adipose tissue gives rise to both white and brown fat cells," Cell Metabolism, Feb. 8, 2012, 15(2):222-9.
Tran et al., "Transplantation of adipose tissue and stem cells: role in metabolism and disease," Nature Reviews Endocrinology, Apr. 2010, 6(4):195-213.
Office Action, in U.S. Appl. No. 11/292,549, dated Apr. 17, 2009 8 pages.
Office Action, in U.S. Appl. No. 11/292,549, dated Jul. 9, 2008 46 pages.
Office Action, in U.S. Appl. No. 11/292,549, dated Sep. 20, 2007, 69 pages.
Restriction Requirement, in U.S. Appl. No. 11/292,549, dated Apr. 18, 2007, 7 pages.
Vakulskas et al., "A high-fidelity Cas9 mutant delivered as a ribonucleoprotein complex enables efficient gene editing in human hematopoietic stem and progenitor cells," Nature Medicine, Aug. 2018, 24(8):1216-24.
Valverde et al., "Insulin and insulin-like growth factor I up-regulate GLUT4 gene expression in fetal brown adipocytes, in a phosphoinositide 3-kinase-dependent manner", Biochemical Journal, Feb. 1, 1999, 337(3):397-405.
Vickers et al., "Efficient Reduction of Target RNAs by Small Interfering RNA and RNase H-dependent Antisense Agents," The Journal of Biological Chemistry, vol. 278:7108-7118 (2003).
Villarroya et al., "Brown adipose tissue as a secretory organ," Nature Reviews Endocrinology, Jan. 2017, 13(1):26-35.
Wang et al., "A PCR primer bank for quantitative gene expression analysis," Nucleic Acids Research, vol. 31:e154 (2003).
Wang et al., "CRISPR-engineered human brown-like adipocytes prevent diet-induced obesity and ameliorate metabolic syndrome in mice," Science Translational Medicine, Aug. 26, 2020, 12(558):eaaz8664, 15 pages.
Wang et al., "The brown fat-enriched secreted factor Nrg4 preserves metabolic homeostasis through attenuation of hepatic lipogenesis," Nature Medicine, Dec. 2014, 20(12):1436-43.
Weitzel et al., "Regulation of mitochondrial biogenesis by thyroid hormone," Experimental Physiology, vol. 88.121-128 {2003}.
Wellen et al., "Obesity-induced inflammatory changes in adipose tissue," The Journal of Clinical Investigation, vol. 112:1785-1788 (2003).
Wells et al., Additivity of mutational effects in proteins, 1990, Biochemistry, vol. 29, pp. 8509-8517.
White et al., "The beneficial effects of brown adipose tissue transplantation," Molecular Aspects of Medicine, Aug. 1, 2019, 68:74-81.
Wilson-Fritch et al., "Mitochondrial Biogenesis and Remodeling during Adipogenesis and in Response to the Insulin Sensitizer Rosiglitazone," Molecular and Cellular Biology, vol. 23:1085-1094 (2003).
Wilson-Fritch et al., "Mitochondrial remodeling in adipose tissue associated with obesity and treatment with rosiglitazone," The Journal of Clinical Investigation, vol. 114:1281-1289 (2004).
Wordinger et al., "Elevated glucose levels influence in vitro hatching, attachment, trophoblast outgrowth and differentiation of the mouse blastocyst," Experientia, Jul. 1978, 34(7):881-2.
Wu et al., "Beige adipocytes are a distinct type of thermogenic fat cell in mouse and human," Cell, Jul. 20, 2012, 150(2):366-76.
Wu et al., "Highly efficient therapeutic gene editing of human hematopoietic stem cells," Nature Medicine, May 2019, 25(5):776-83.
Xiong et al., "A novel brown adipocyte-enriched long non-coding RNA that is required for brown adipocyte differentiation and sufficient to drive thermogenic gene program in white adipocytes," Biochimica Et Biophysica Acta (BBA)-Molecular and Cell Biology of Lipids, Apr. 1, 2018, 1863(4):409, 41 pages.
Xu et al., "Bioorthogonally cross-linked hydrogel network with precisely controlled disintegration time over a broad range," Journal of the American Chemical Society, Mar. 19, 2014, 136(11):4105-8.
Xu et al., "Structural basis for antagonist-mediated recruitment of nuclear co-repressors by PPARalpha," Nature, vol. 415:813-817 (2002).
Xue et al., "Mesodermal patterning defect in mice lacking the Ste20 NCK interacting kinase (NIK)," Development, vol. 128:1559-1572 (2001).
Yao et al., "A Novel Human STE20-related Protein Kinase, HGK, That Specifically Activates the c-Jun N-terminal Kinase Signaling Pathway," The Journal of Biological Chemistry, vol. 274:2118-2125 (1999).
Yoshimura et al., Adipose-derived stem/progenitor cells: roles in adipose tissue remodeling and potential use for soft tissue augmentation, Regenerative Medicine, Mar. 2009. 4(2):265-73.
Yoshimura et al., "Cell-assisted lipotransfer for facial lipoatrophy: efficacy of clinical use of adipose-derived stem cells," Dermatologic Surgery, Sep. 2008, 34(9):1178-85.
Yoshimura et al., "Progenitor-enriched adipose tissue transplantation as rescue for breast implant complications," The Breast Journal, Mar. 2010, 16(2):169-75.
Zhang et al., "Negative Regulation of Peroxisome Proliferator-Activated Receptor-y Gene Expression Contributes to the Antiadipogenic Effects of Tumor Necrosis Factor-a," Molecular Endocrinology, vol. 10:1457-1466 (2007).
Zilliacus et al., Regulatiion of Glucocorticoid Receptor Activity by 14-3-3-Dependent Intracellular Relocalization of the Corepressor RIP140, Molecular Endocrinology, vol. 15:501-511 (2001).
CN Office Action in Chinese Appln. No. 201880051908.1, dated Sep. 27, 2022, 14 pages (with English translation).
CA Office Action in Canadian Appln. No. 3,072,340, dated Aug. 8, 2023, 7 pages.
CN Office Action in Chinese Appln. No. 201880051908.1, dated Apr. 15, 2023, 18 pages (with English translation).
Corvera, "CRISPR-Based Gene Editing to Induce Thermogenic Adipose Tissue in Type 2 Diabetes," University of Massachusetts School, Apr. 1, 2020, 26 pages.
PCT International Preliminary Report on Patentability in International Appln. No. PCT/US2021/054155, dated Apr. 20, 2023, 9 pages.
Farhang et al., "CRISPR-based epigenome editing of cytokine receptors for the promotion of cell survival and tissue deposition in inflammatory environments," Tissue Engineering Part A, Aug. 2017, 23(15-16):738, 14 pages.
Feng et al., "Efficient genome editing in plants using a CRISPR/Cas system," Cell Research, Oct. 2013, 23(10):1229-32.
Jinek et al., "RNA-programmed genome editing in human cells," elife, Jan. 2013, 2:e00471, 9 pages.

(56) References Cited

OTHER PUBLICATIONS

Spaite et al., "Optimal out-of-hospital blood pressure in major traumatic brain injury: a challenge to the current understanding of hypotension," Annals of Emergency Medicine, Jul. 1, 2022, 80(1):46-59.

* cited by examiner

SpyCas9 + NRIP1 sgRNA-H5 + 7.5 pmol dsODN)

| Replicate 1 | sgRNA-H5 sequence | PAM | |
|---|---|---|---|
| | G T C A T G T G C T G C A A G A T T A C N G G | | Reads |
| ▶ | . . . . . . . . . . . . . . . . . . . . . . | | 5220 |

Fig. 11c

SpyCas9 + NRIP1 sgRNA-H5 + 10 pmol dsODN)

| Replicate 2 | sgRNA-H5 sequence | PAM | |
|---|---|---|---|
| | G T C A T G T G C T G C A A G A T T A C N G G | | Reads |
| ▶ | . . . . . . . . . . . . . . . . . . . . . . | | 5687 |

Fig. 11d

| | sgRNA-H5 sequence | PAM |
|---|---|---|
| | G T C A T G T G C T G C A A G A T T A C N G G | |
| hOT1 | A . . . A . . T . . . . . . . . . . . . . . | |
| hOT2 | . A . . . . . . . . . A . . . . . . T . . . | |
| hOT3 | . C . . . . . . . . . . C . T . . . . . . . | |
| hOT4 | T . . . . . T . . . . T T . . . . . . . . . | |
| hOT5 | . . . T . T . . . . . C A . . . . . . . . . | |

Fig. 11e

SEQUENCE LISTING

<160> NUMBER OF SEQ ID NOS: 42

<210> SEQ ID NO 1
<211> LENGTH: 7
<212> TYPE: PRT
<213> ORGANISM: Artificial Sequence
<220> FEATURE:
<223> OTHER INFORMATION: SV40 large T antigen NLS

<400> SEQUENCE: 1

Pro Lys Lys Lys Arg Arg Val
1               5

<210> SEQ ID NO 2
<211> LENGTH: 7
<212> TYPE: PRT
<213> ORGANISM: Artificial Sequence
<220> FEATURE:
<223> OTHER INFORMATION: SV40 large T antigen NLS

<400> SEQUENCE: 2

Pro Lys Lys Lys Arg Lys Val
1               5

<210> SEQ ID NO 3
<211> LENGTH: 18
<212> TYPE: PRT
<213> ORGANISM: Artificial Sequence
<220> FEATURE:
<223> OTHER INFORMATION: SV40 large T antigen NLS

<400> SEQUENCE: 3

Lys Arg Thr Ala Asp Gly Ser Glu Phe Glu Ser Pro Lys Lys Lys Arg
1               5                   10                  15

Lys Val

<210> SEQ ID NO 4
<211> LENGTH: 16
<212> TYPE: PRT
<213> ORGANISM: Artificial Sequence
<220> FEATURE:
<223> OTHER INFORMATION: nucleoplasmin NLS

<400> SEQUENCE: 4

Lys Arg Pro Ala Ala Thr Lys Lys Ala Gly Gln Ala Lys Lys Lys Lys
1               5                   10                  15

<210> SEQ ID NO 5
<211> LENGTH: 60
<212> TYPE: DNA
<213> ORGANISM: Artificial Sequence
<220> FEATURE:
<223> OTHER INFORMATION: polyadenylation signal

<400> SEQUENCE: 5
tagcaataaa ggatcgttta ttttcattgg aagcgtgtgt tggttttttg atcaggcgcg    60

<210> SEQ ID NO 6
<211> LENGTH: 20
<212> TYPE: RNA
<213> ORGANISM: Mus musculus

<400> SEQUENCE: 6
cuuguauuga acaugacuca                                                20

```
<210> SEQ ID NO 7
<211> LENGTH: 20
<212> TYPE: RNA
<213> ORGANISM: Mus musculus

<400> SEQUENCE: 7 augucuuaa cuuaccucga                                                  20

<210> SEQ ID NO 8
<211> LENGTH: 20
<212> TYPE: RNA
<213> ORGANISM: Mus musculus

<400> SEQUENCE: 8
gucaguaccc agacguacca                                                 20

<210> SEQ ID NO 9
<211> LENGTH: 20
<212> TYPE: RNA
<213> ORGANISM: Mus musculus

<400> SEQUENCE: 9
auaagguuug gagucacguc                                                 20

<210> SEQ ID NO 10
<211> LENGTH: 20
<212> TYPE: RNA
<213> ORGANISM: Mus musculus

<400> SEQUENCE: 10
cacuuugucc cacugcggga                                                 20

<210> SEQ ID NO 11
<211> LENGTH: 20
<212> TYPE: RNA
<213> ORGANISM: Mus musculus

<400> SEQUENCE: 11
acaggcuguu gccagcaugg                                                 20

<210> SEQ ID NO 12
<211> LENGTH: 20
<212> TYPE: RNA
<213> ORGANISM: Mus musculus

<400> SEQUENCE: 12
ggagucgaag aacaucugca                                                 20

<210> SEQ ID NO 13
<211> LENGTH: 20
<212> TYPE: RNA
<213> ORGANISM: Homo sapiens

<400> SEQUENCE: 13
cuucuauuga acaugacuca                                                 20

<210> SEQ ID NO 14
<211> LENGTH: 20
<212> TYPE: RNA
<213> ORGANISM: Homo sapiens

<400> SEQUENCE: 14
gcuuggcucu gaugugcacc                                                 20
```

```
<210> SEQ ID NO 15
<211> LENGTH: 20
<212> TYPE: RNA
<213> ORGANISM: Homo sapiens

<400> SEQUENCE: 15
acacauacau aucagggguc                                              20

<210> SEQ ID NO 16
<211> LENGTH: 20
<212> TYPE: RNA
<213> ORGANISM: Homo sapiens

<400> SEQUENCE: 16
acaucaggaa gauucguauc                                              20

<210> SEQ ID NO 17
<211> LENGTH: 20
<212> TYPE: RNA
<213> ORGANISM: Homo sapiens

<400> SEQUENCE: 17
gucaugugcu gcaagauuac                                              20

<210> SEQ ID NO 18
<211> LENGTH: 20
<212> TYPE: RNA
<213> ORGANISM: Homo sapiens

<400> SEQUENCE: 18
uuugcauggu cccuaagaaa                                              20

<210> SEQ ID NO 19
<211> LENGTH: 20
<212> TYPE: RNA
<213> ORGANISM: Artificial Sequence
<220> FEATURE:
<223> OTHER INFORMATION: Non-Targeting control sgRNA

<400> SEQUENCE: 19
gcacuaccag agcuaacuca                                              20

<210> SEQ ID NO 20
<211> LENGTH: 4153
<212> TYPE: DNA
<213> ORGANISM: Mus musculus

<400> SEQUENCE: 20
tactgacgtg cgtttggtga gcaacgaaag atgatgaaga agaaaaacca gcatattccc    60
tgagacctgg gtgccagcgc tgccgctgtg ctaaggaagt tgcgaggctg gcccttgcct   120
agccactcat cagtgctgta gtctgcaccc gagtttgccc cagcctctga gcccctcgtc   180
actgcctgaa gatcccctgg tcagaatgtt aacagtgcat ctctgcccga ctgctatggg   240
aggtgatcag gtgacgctca cttcctgacg tcacgtggga tcttactgac gagaggagct   300
ctttcacgtg aacggaagcc gagccccgtgt gagcgcttgt attgaacatg actcatggag   360
aagagcttgg ctctgatgtg catcaggatt ctattgtctt aacttacctc gaagggttac   420
taatgcatca ggcagcaggg ggatcaggca ctgccattaa caaaaagtct gctggccaca   480
aagaggaaga ccagaacttt aacctctcgg gcagtgcgtt tccctcctgt caaagcaatg   540
gtcccactgt cagtacccag acgtaccagg gatctggcat gctgcacctc aaaaaagcca   600
```

```
gactgctgca gtcttccgag gactggaacg cggcaaagcg gaagaggctg tctgattcca    660
tcgtgaattt aaacgtaaag aaggaagcgt tgctggctgg catggttgac agtgtgccta    720
aaggcaaaca ggatagcaca ttgctggcct ctttgcttca gtcattcagc tctaggctgc    780
agactgttgc tctgtcacag cagattagac agagcctcaa ggagcaggga tatgccctca    840
gtcacgagtc tttaaaagtg gagaaggatt taaggtgcta tggcgtggcc tcaagtcact    900
taaaaactct gttgaagaaa agtaaaacca aggatcaaaa gtcaggtccc accctccctg    960
acgtgactcc aaaccttatc agagatagct tgttgagtc atcccatccc gcagtgggac    1020
aaagtgggac aaaggtcatg agtgagccct tgtcatgtgc tgcaagatta caggctgttg    1080
ccagcatggt ggagaaaagg gcgagtcccg ctgcctcccc aaagcctagt gttgcctgca    1140
gccagttggc gctgctcctg tccagcgagg cccacctgca gcagtactct cgggaacatg    1200
ctctaaaaac gcagaacgca catcaggtgg caagcgaaag acttgcagcc atggccagat    1260
tgcaagagaa tggcagaag gacgtgggca gttcgcagct ctccaaaggg gtgtctggcc    1320
atctcaacgg gcaggccaga gcactgccgg caagcaaact ggtggccaac aagaataacg    1380
ctgccacctt tcagagtcca atgggtgttg tcccttcctc ccccaaaaac acgagctata    1440
agaactcact ggaaagaaac aacctaaagc aggctgctaa taacagtctg cttttgcatc    1500
tcctcaaaag ccagaccata cccacgccga tgaacgggca cagccagaac gagagagcga    1560
gcagttttga gagtagcacg cccaccacga ttgatgagta ctccgataac aacccgagct    1620
ttacagatga cagcagtgga gacgaaagct cgtactccaa ttgcgttccc atagacctgt    1680
cttgcaaaca ccggatcgaa aagccggaag ctgagcggcc cgtttcgctg gagaacctaa    1740
cccagtcctt gttaaacacg tgggatccca agatccccgg cgttgacatc aaagaagatc    1800
aagatacctc aacaaattcc aagctgaatt cacaccagaa agtcactctt cttcagttgc    1860
tgctcggcca taaagtgaa gaaactgttg aaaggaacgc cagccctcag gacatccata    1920
gtgatgggac taagttcagt cctcagaatt acacaaggac ttctgtcatc gaaagcccca    1980
gtaccaacag gactaccccca gtgagcactc caccactgta tacagccagc caagcagagt    2040
ctcccatcaa tctttcccag cactctctgg tcatcaagtg gaattcccg ccgtatgcct    2100 gcagtactcc cgcttccaag ctcacgaaca ccgcgcctag ccacctgatg gacctcacga    2160
aaggcaaaga gtcccaagcc gagaaaccag ccccgagtga aggtgcacaa aattccgcca    2220
cgttcagtgc cagtaaactg ttacaaaatt tggctcagtg cggattgcag tcttccgggc    2280
caggggaaga gcagagaccc tgcaaacagc tgttaagtgg aaacccagac aaacctctcg    2340
gtctgattga tagattaaac agccctctgc tctcaaataa aaccaatgcg gctgaagaga    2400
gcaaagcctt cagcagtcag cctgccgggc ctgagccggg acttcctggt tgtgagatag    2460
aaaatctctt ggaaagacgg actgtccttc agttgctcct gggaaattcc agcaaaggga    2520
agaatgagaa gaaagagaaa accccgcac gagacgaggc tcctcaggag cattcggaga    2580
gggctgcaaa tgaacagata tcatggtga agattaaatc cgagccttgt gacgacttcc    2640
agacccacaa cacaaacctg cccttaaacc acgatgccaa gagcgccccc ttcttaggtg    2700
tgactcccgc catccacagg agcacagcgg ccttaccagt gtcggaggac tttaaatccg    2760
agcctgcttc acctcaggat ttctcttct caaagaacgg gctgttgagt cgcttgctga    2820
gacagaatca agagagttac ccggcagatg agcaggacaa gagtcacaga aacagtgagc    2880
tgccaaccct ggagtcgaag aacatctgca tggtcccgaa gaaaaggaag ctgtatacgg    2940
```

| | | |
|---|---|---|
| aaccactgga gaatccattt aaaaagatga aaaatactgc cgtagatact gccaatcatc | 3000 | |
| acagcggccc ggaagtactc tacgggtcgt tgcttcatca ggaagagctg aagtttagca | 3060 | |
| ggaatgagct cgattataaa taccctgctg ggcatagttc agccagcgat ggtgaccaca | 3120 | |
| ggagttgggc cagagagagc aaaagcttca atgttctcaa gcagctgctg ctctccgaga | 3180 | |
| actgtgtgcg agatctgtcc ccacacagga gtgactctgt ccccgacacg aaaaagaaag | 3240 | |
| gacacaaaaa caacgcgccc ggcagcaaac ctgaattcgg catttcttct ttaaatggac | 3300 | |
| tgatgtatag ttccccgcag cctggcagtt gtgtgacgga tcataggaca ttttcatacc | 3360 | |
| cgggaatggt aaagacccct ctgagccctc cttcccaga gcacttgggc tgtgtgggt | 3420 | |
| ccagaccaga acctgggctt tgaatggat gttccgtgcc cggtgagaag ggacccatta | 3480 | |
| agtgggtcat cgcagatatg gataagaatg aatacgaaaa agactctcca agactgacca | 3540 | |
| aaactaatcc gatcctctat tacatgctcc agaagggagg gggcaattct gttaccacac | 3600 | |
| aagaaaccca ggacaaagac atctggaggg agcctgcgtc agccgagagt ctctcacagg | 3660 | |
| ttacagtcaa agaagagcta cttcccgctg cagaaactaa agcttctttc tttaatctaa | 3720 | |
| gaagcccgta caatagccat atgggaaata atgcttctcg cccacacagt acaaatggag | 3780 | |
| aagtgtatgg acttctggga aacgcgctca ccataaaaaa agagtcagaa taaatgtgta | 3840 | |
| cctgccatac cactttgggt cttttttaaaa tttagtcagt atgaacttga gatctgtata | 3900 | |
| aataagagca tgatttgaga aaagcatggt ataactgaaa ctccttcctt ttgaaagtat | 3960 | |
| tggtcactgg tgatgtttaa atatgcatac taattttgc ttaacattag atgtcatgag | 4020 | |
| gaaacaattg aactcgaggt tggttgttta ctatttctgt atgcatcaga taacaactgt | 4080 | |
| gactagccta cgaatgaacc tgttttata atcgtaaata agaggcatac attaaaatgc | 4140 | |
| acaacttcac cag | 4153 | |

<210> SEQ ID NO 21
<211> LENGTH: 7291
<212> TYPE: DNA
<213> ORGANISM: Homo sapiens

<400> SEQUENCE: 21

| | | |
|---|---|---|
| acactgatat ttgcatttaa tggggaacaa aagatgaaga aggaaaagga atatattcac | 60 | |
| taaggattct atctgcttac tgctacagac ctatgtgtta aggaattctt ctcctcctcc | 120 | |
| ttgcgtagaa gttgatcagc actgtggtca gactgcattt atcttgtcat tgccagaaga | 180 | |
| aatcttggac agaatgtaac agtacgtctc tctctgattg cgatggaagg tgataaactg | 240 | |
| atactccttt attaaagtta catcgcactc accacagaaa accattcttt aaagtgaata | 300 | |
| gaaaccaagc ccttgtgaac acttctattg aacatgactc atggagaaga gcttggctct | 360 | |
| gatgtgcacc aggattctat tgttttaact taccagaag gattactaat gcatcaggca | 420 | |
| gcaggggat caggtactgc cgttgacaaa agtctgctg gcataatga agaggatcag | 480 | |
| aactttaaca tttctggcag tgcatttccc acctgtcaaa gtaatggtcc agttctcaat | 540 | |
| acacatacat atcaggggtc tggcatgctg cacctcaaaa aagccagact gttgcagtct | 600 | |
| tctgaggact ggaatgcagc aaagcggaag aggctgtctg attctatcat gaatttaaac | 660 | |
| gtaaagaagg aagctttgct agctggcatg gttgacagtg tgcctaaagg caaacaggat | 720 | |
| agcacattac tggcctcttt gcttcagtca ttcagctcta ggctgcagac tgttgctctg | 780 | |
| tcacaacaaa tcaggcagag cctcaaggag caaggatatg ccctcagtca tgattcttta | 840 | |
| aaagtggaga aggatttaag gtgctatggt gttgcatcaa gtcacttaaa aactttgttg | 900 | |

```
aagaaaagta aagttaaaga tcaaaagcct gatacgaatc ttcctgatgt gactaaaaac    960
ctcatcagag ataggtttgc agagtctcct catcatgttg acaaagtgg aacaaaggtc   1020
atgagtgaac cgttgtcatg tgctgcaaga ttacaggctg ttgcaagcat ggtggaaaaa   1080
agggctagtc ctgccacctc acctaaacct agtgttgctt gtagccagtt agcattactt   1140
ctgtcaagcg aagcccattt gcagcagtat tctcgagaac acgctttaaa acgcaaaat   1200
gcaaatcaag cagcaagtga aagacttgct gctatggcca gattgcaaga aaatggccag   1260
aaggatgttg gcagttacca gctcccaaaa ggaatgtcaa gccatcttaa tggtcaggca   1320
agaacatcat caagcaaact gatggctagc aaaagtagtg ctacagtgtt tcaaaatcca   1380
atgggtatca ttccttcttc ccctaaaaat gcaggttata agaactcact ggaaagaaac   1440
aatataaaac aagctgctaa caatagtttg ctttacatc ttcttaaaag ccagactata   1500
cctaagccaa tgaatggaca cagtcacagt gagagaggaa gcattttga ggaaagtagt   1560
acacctacaa ctattgatga atattcgat aacaatccta gttttacaga tgacagcagt   1620
ggtgatgaaa gttcttattc caactgtgtt cccatagact tgtcttgcaa acaccgaact   1680
gaaaaatcag aatctgacca acctgttcc ctggataact tcactcaatc cttgctaaac   1740
acttgggatc caaaagtccc agatgtagat atcaaagaag atcaagatac ctcaaagaat   1800
tctaagctaa actcacacca gaaagtaaca cttcttcaat tgctacttgg ccataagaat   1860
gaagaaaatg tagaaaaaaa caccagccct cagggagtac acaatgatgt gagcaagttc   1920
aatacacaaa attatgcaag gacttctgtg atagaaagcc ccagtacaaa tcggactact   1980
ccagtgagca ctccacccttt acttacatca agcaaagcag ggtctcccat caatctctct   2040
caacactctc tggtcatcaa atggaattcc ccaccatatg tctgcagtac tcagtctgaa   2100
aagctaacaa atactgcatc taaccactca atggaccta caaaaagcaa agacccacca   2160
ggagagaaac cagcccaaaa tgaaggtgca cagaactctg caacgtttag tgccagtaag   2220
ctgttacaaa atttagcaca atgtggaatg cagtcatcca tgtcagtgga agagcagaga   2280
cccagcaaac agctgttaac tggaaacaca gataaaccga taggtatgat tgatagatta   2340
aatagccctt tgctctcaaa taaaacaaat gcagttgaag aaaataaagc atttagtagt   2400
caaccaacag gtcctgaacc agggcttttct ggttctgaaa tagaaaatct gcttgaaaga   2460
cgtactgtcc tccagttgct cctggggaac cccaacaaag ggaagagtga aaaaaaagag   2520
aaaactccct aagagatga agtactcag gaacactcag agagagcttt aagtgaacaa   2580
atactgatgg tgaaaataaa atctgagcct tgtgatgact acaaattcc taacacaaat   2640
gtgcacttga gccatgatgc taagagtgcc ccattcttgg gtatggctcc tgctgtgcag   2700
agaagcgcac ctgccttacc agtgtccgaa gactttaaat cggagcctgt ttcacctcag   2760
gatttttctt tctccaagaa tggtctgcta agtcgattgc taagacaaaa tcaagatagt   2820
tacctggcag atgattcaga caggagtcac agaaataatg aaatggcact tctagaatca   2880
aagaatcttt gcatggtccc taagaaaagg aagctttata ctgagccatt agaaaatcca   2940
tttaaaaaga tgaaaacaa cattgttgat gctgcaaaca atcacagtgc cccagaagta   3000
ctgtatgggt ccttgcttaa ccaggaagag ctgaaattta gcagaaatga tcttgaattt   3060
aaatatcctg ctggtcatgg ctcagccagc gaaagtgaac acaggagttg ggccagagag   3120
agcaaaagct ttaatgttct gaacagctg cttctctcag aaaactgtgt gcgagatttg   3180
tccccgcaca gaagtaactc tgtggctgac agtaaaaaga aaggacacaa aaataatgtg   3240
```

-continued

```
accaacagca aacctgaatt tagcatttct tctttaaatg gactgatgta cagttccact    3300
cagcccagca gttgcatgga taacaggaca ttttcatacc caggtgtagt aaaaactcct    3360
gtgagtccta cttttccctga gcacttgggc tgtgcagggt ctagaccaga atctgggctt   3420
ttgaatgggt gttccatgcc cagtgagaaa ggacccatta agtgggttat cactgatgcg    3480
gagaagaatg agtatgaaaa agactctcca agattgacca aaaccaaccc aatactatat    3540
tacatgcttc aaaaaggagg caattctgtt accagtcgag aaacacaaga caaggacatt    3600
tggagggagg cttcatctgc tgaaagtgtc tcacaggtca cagccaaaga agagttactt    3660
cctactgcag aaacgaaagc ttctttcttt aatttaagaa gcccttacaa tagccatatg    3720
ggaaataatg cttctcgccc acacagcgca aatggagaag tttatggact tctgggaagc    3780
gtgctaacga taaagaaaga atcagaataa aatgtacctg ccatccagtt ttggatcttt    3840
ttaaaactaa tgagtatgaa cttgagatct gtataaataa gagcatgatt tgaaaaaaag    3900
catggtataa ttgaaacttt tttcattttg aaaagtattg gttactggtg atgttgaaat    3960
atgcatacta attttttgctt aacattagat gtcatgagga aactactgaa ctagcaattg   4020
gttgtttaac acttctgtat gcatcagata acaactgtga gtagcctatg aatgaaattc    4080
ttttataaat attaggcata aattaaaatg taaaactcca ttcatagtgg attaatgcat    4140
tttgctgcct ttattagggt actttatttt gcttttcaga agtcagccta cataacacat    4200
ttttaaagtc taaactgtta aacaactctt taaaggataa ttatccaata aaaaaaaacc    4260
tagtgctgat tcacagctta ttatccaatt caaaaataaa ttagaaaaat atatgcttac    4320
atttttcact tttgctaaaa agaaaaaaaa aaggtgttta ttttttaactc ttggaagagg   4380
ttttgtggtt cccaatgtgt ctgtcccacc ctgatccttt tcaatatata tttctttaaa    4440
ccttgtgcta cttagtaaaa attgattaca attgagggaa gtttgataga tccttttaaaa   4500
aaaaggcaga tttccatttt ttgtattttta actactttac taaattaata ctcctccttt    4560
tacagaatta gaaaagttaa catttatctt taggtggttt cctgaaaagt tgaatattta    4620
agaaattgtt tttaacagaa gcaaaatggc ttttctttgg acagttttca ccatctcttg    4680
taaaagttaa ttctcaccat tcctgtggta cctgcgagtg ttatgaccag gattccttaa    4740
acctgaactc agaccacttg cattagaacc atctggagca cttgttttaa aatgcagatt    4800
cataggcagc atctcagatc tacagaacaa gaatctctgc taagtggacc tggaatcttc    4860
catctgcatc ttaacatgct ctctaggtgt ttcttgtgtt tgagaaccat gacttatgac    4920
tttcctcaga acatgagact gtaaaacaaa aacaaaaaac tatgtgatgc ctctattttc    4980
cccaatacag tcacacatca gctcaaaatt tgcaatattg tagttcatat attaccgtta    5040
tgtctttgga aatcgggttc agaacacttt ttatgacaaa aattgggtgg agggataac     5100
tttcatatct ggctcaacat ctcaggaaaa tctgtgatta tttgtgtgtt ctaatgagta    5160
acatctactt agttagcctt agggatggaa aaacagggcc acttaccaaa ctcaggtgat    5220
tccaggatgg tttggaaact tctcctgaat gcatccttaa cctttattaa aaccattgtc    5280
ctaagaacaa tgccaacaaa gcttacaaca tttagtttaa acccaagaag ggcactaaac    5340
tcagattgac taaataaaaa gtacaaaggg cacatatacg tgacagaatt gtacacaatc    5400
actccattgg atctttttact ttaaagtagt gatgaaaagt acatgttgat actgtcttag   5460
aagaaattaa tatattagtg aagccacatg gggtttcagt tgcgaaacag gtctgttttt    5520
atgttcagtt tgtacaatcc acaattcatt caccagatat tttgttctta attgtgaacc    5580
aggttagcaa atgacctatc aaaaattatt ctataatcac tactagttag gatattgatt    5640
```

```
taaaattgtt ctacttgaag tggtttctaa gattttata ttaaaaatag gtgtgatttc    5700
ctaatatgat ctaaaaccct aaatggttat ttttcctcag aatgatttgt aaatagctac    5760
tggaaatatt atacagtaat aggagtgggt attatgcaac atcatggaga agtgaaggca    5820
taggcttatt ctgacataaa attccactgg ccagttgaat atattctatt ccatgtccat    5880
actatgacaa tcttattgtc aacactatat aaataagctt ttaaacaagt catttttctt    5940
gatcgttgtg gaaggtttgg agccttagag gtatgtcaga aaaaatatgt tggtattctc    6000
ccttgggtag ggggaaatga ccttttaca agagagtgaa atttaggtca gggaaaagac     6060
caagggccag cattgctact tttgtgtgtg tgtgtgtggg ttttgttttg ttttttggt     6120 tggctggttg ttttcgttgt tgttaacaaa ggaatgagaa tatgtaatac ttaaataaac    6180
atgaccacga agaatgctgt tctgatttac tagagaatgt tcccaatttg aatttagggt    6240
gattttaaag aacagtgaga aagggcatac atccacagat tcactttgtt tatgcatatg    6300
tagatacaag gatgcacata tacacatttt caaggactat tttagatatc tagacaattt    6360
cttctaataa agtcatttgt gaaagggtac tacagcttat tgacatcagt aaggtagcat    6420
tcattacctg tttattctct gctgcatctt acagaagagt aaactggtga gagtatatat    6480
tttatatata tatatatata tatatatata atatgtatat atatatatat tgacttgtta    6540
catgaagatg ttaaaatcgg tttttaaagg tgatgtaaat agtgatttcc ttaatgaaaa    6600
atacatattt tgtattgttc taatgcaaca gaaaagcctt ttaatctctt tggttcctgt    6660
atattccatg tataagtgta aatataatca gacaggttta aaagttgtgc atgtatgtat    6720
acagttgcaa gtctggacaa atgtatagaa taaaccttt atttaagttg tgattacctg     6780
ctgcatgaaa agtgcatggg ggaccctgtg catctgtgca tttggcaaaa tgtcttaaca    6840
aatcagatca gatgttcatc ctaacatgac agtattccat ttctggacat gacgtctgtg    6900
gtttaagctt tgtgaaagaa tgtgctttga ttcgaagggt cttaaagaat tttttaatc     6960 gtcaaccact tttaaacata aagaattcac acaactactt tcatgaattt tttaatccca    7020
ttgcaaacat tattccaaga gtatcccagt attagcaata ctggaatata ggcacattac    7080
cattcatagt aagaattctg gtgtttacac aaccaaattt gatgcgatct gctcagtaat    7140
ataatttgcc attttatta gaaatttaat ttcttcatgt gatgtcatga aactgtacat     7200
actgcagtgt gaatttttt gttttgtttt taatctttt agtgtttact tcctgcagtg      7260
aatttgaata aatgagaaaa aatgcattgt c                                   7291
```

<210> SEQ ID NO 22
<211> LENGTH: 20
<212> TYPE: DNA
<213> ORGANISM: Homo sapiens

<400> SEQUENCE: 22

```
tttgcatggt ccctaagaaa                                                  20
```

<210> SEQ ID NO 23
<211> LENGTH: 63
<212> TYPE: DNA
<213> ORGANISM: Artificial Sequence
<220> FEATURE:
<223> OTHER INFORMATION: synthetic nucleic acid

<400> SEQUENCE: 23

```
ccttgtcatg tgctgcaaga ttacaggctg ttgccagcag ggggaaaaaa gggggagccc     60
``` ccc                                                                    63

<210> SEQ ID NO 24
<211> LENGTH: 23
<212> TYPE: DNA
<213> ORGANISM: Artificial Sequence
<220> FEATURE:
<223> OTHER INFORMATION: sgRNA-M6 sequence PAM

<400> SEQUENCE: 24
acaggctgtt gccagcatgg tgg                                              23

<210> SEQ ID NO 25
<211> LENGTH: 23
<212> TYPE: DNA
<213> ORGANISM: Artificial Sequence
<220> FEATURE:
<223> OTHER INFORMATION: synthetic nucleic acid

<400> SEQUENCE: 25
gagggctgtt gccagcatgg tgg                                              23

<210> SEQ ID NO 26
<211> LENGTH: 23
<212> TYPE: DNA
<213> ORGANISM: Artificial Sequence
<220> FEATURE:
<223> OTHER INFORMATION: synthetic nucleic acid

<400> SEQUENCE: 26
aaaggctgct gccagcatga ggg                                              23

<210> SEQ ID NO 27
<211> LENGTH: 23
<212> TYPE: DNA
<213> ORGANISM: Artificial Sequence
<220> FEATURE:
<223> OTHER INFORMATION: synthetic nucleic acid

<400> SEQUENCE: 27
gggggctgct gccagcatgg ggg                                              23

<210> SEQ ID NO 28
<211> LENGTH: 23
<212> TYPE: DNA
<213> ORGANISM: Artificial Sequence
<220> FEATURE:
<223> OTHER INFORMATION: synthetic nucleic acid

<400> SEQUENCE: 28
gtaggctgct gctagcatgg tgg                                              23

<210> SEQ ID NO 29
<211> LENGTH: 23
<212> TYPE: DNA
<213> ORGANISM: Artificial Sequence
<220> FEATURE:
<223> OTHER INFORMATION: synthetic nucleic acid

<400> SEQUENCE: 29
cacggctgct gtcagcatgg tgg                                              23

<210> SEQ ID NO 30
<211> LENGTH: 23
<212> TYPE: DNA
<213> ORGANISM: Artificial Sequence

```
<220> FEATURE:
<223> OTHER INFORMATION: synthetic nucleic acid

<400> SEQUENCE: 30
acaagctgtt gccatcatgg ggg                                          23

<210> SEQ ID NO 31
<211> LENGTH: 23
<212> TYPE: DNA
<213> ORGANISM: Artificial Sequence
<220> FEATURE:
<223> OTHER INFORMATION: synthetic nucleic acid

<400> SEQUENCE: 31
acagacagtc accagcatgg tgg                                          23

<210> SEQ ID NO 32
<211> LENGTH: 23
<212> TYPE: DNA
<213> ORGANISM: Artificial Sequence
<220> FEATURE:
<223> OTHER INFORMATION: synthetic nucleic acid

<400> SEQUENCE: 32
acaggctgtt gtcagcatgt gga                                          23

<210> SEQ ID NO 33
<211> LENGTH: 23
<212> TYPE: DNA
<213> ORGANISM: Artificial Sequence
<220> FEATURE:
<223> OTHER INFORMATION: synthetic nucleic acid

<400> SEQUENCE: 33
aaaagctgtt gccagcatgt ggg                                          23

<210> SEQ ID NO 34
<211> LENGTH: 23
<212> TYPE: DNA
<213> ORGANISM: Artificial Sequence
<220> FEATURE:
<223> OTHER INFORMATION: synthetic nucleic acid

<400> SEQUENCE: 34
ccaggctggt gccagaatgg agg                                          23

<210> SEQ ID NO 35
<211> LENGTH: 23
<212> TYPE: DNA
<213> ORGANISM: Artificial Sequence
<220> FEATURE:
<223> OTHER INFORMATION: synthetic nucleic acid

<400> SEQUENCE: 35
acaggctagg gctagcatgg agg                                          23

<210> SEQ ID NO 36
<211> LENGTH: 23
<212> TYPE: DNA
<213> ORGANISM: Artificial Sequence
<220> FEATURE:
<223> OTHER INFORMATION: synthetic nucleic acid

<400> SEQUENCE: 36
acaaactgct accagcatag tgg                                          23
```

```
<210> SEQ ID NO 37
<211> LENGTH: 23
<212> TYPE: DNA
<213> ORGANISM: Artificial Sequence
<220> FEATURE:
<223> OTHER INFORMATION: sgRNA-H5 sequence PAM
<220> FEATURE:
<221> NAME/KEY: misc_feature
<222> LOCATION: (21)..(21)
<223> OTHER INFORMATION: n=a, t, c, or g

<400> SEQUENCE: 37
gtcatgtgct gcaagattac ngg                                              23

<210> SEQ ID NO 38
<211> LENGTH: 23
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (21)..(21)
<223> OTHER INFORMATION: n=a, t, c, or g

<400> SEQUENCE: 38
atcaagttct gcaagattac ngg                                              23

<210> SEQ ID NO 39
<211> LENGTH: 23
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (21)..(21)
<223> OTHER INFORMATION: n=a, t, c, or g

<400> SEQUENCE: 39
gacatgtgct gaaagatttc ngg                                              23

<210> SEQ ID NO 40
<211> LENGTH: 23
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (21)..(21)
<223> OTHER INFORMATION: n=a, t, c, or g

<400> SEQUENCE: 40
gccatgtgct ccatgattac ngg                                              23

<210> SEQ ID NO 41
<211> LENGTH: 23
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (21)..(21)
<223> OTHER INFORMATION: n=a, t, c, or g

<400> SEQUENCE: 41
ttcatgttct gttagattac ngg                                              23
```

```
<210> SEQ ID NO 42
<211> LENGTH: 23
<212> TYPE: DNA
<213> ORGANISM: Artificial Sequence
<220> FEATURE:
<223> OTHER INFORMATION: synthetic nucleic acid
<220> FEATURE:
<221> NAME/KEY: misc_feature
<222> LOCATION: (21)..(21)
<223> OTHER INFORMATION: n=a, t, c, or g

<400> SEQUENCE: 42
gtcttttgct caaagattac ngg                                              23
```

TARGETING Nrip1 TO ALLEVIATE METABOLIC DISEASE

CLAIM OF PRIORITY

This application claims the benefit of U.S. Provisional Patent Application Ser. No. 63/089,955, filed on Oct. 9, 2020. The entire contents of the foregoing are hereby incorporated by reference.

FEDERALLY SPONSORED RESEARCH OR DEVELOPMENT

This invention was made with Government support under W81XWH-18-1-0397, and W81XWH-18-1-0398 awarded by the Medical Research and Materiel Command, and DK030898 awarded by the National Institutes of Health. The Government has certain rights in the invention.

TECHNICAL FIELD

Methods and compositions provided herein involve engineered adipose cells for treating conditions associated with an elevated body mass index (BMI) such as diabetes.

INCORPORATION BY REFERENCE OF SEQUENCE LISTING FILED ELECTRONICALLY

This application includes an electronic version of the Sequence Listing, the contents of which are incorporated by reference in their entirety. The computer-readable file, created on Aug. 17, 2023, is 23,185 bytes in size and titled 07917-0422001_SL_ST25.txt.

BACKGROUND

Metabolic disease is a significant issue in human health globally; type 2 diabetes (T2D) affects nearly an astounding 10% of the population of the United States (see cdc.gov/diabetes/basics/type2.html). Overweight and obese men and women account for about two thirds of the USA population, and are greatly at risk of developing T2D. African Americans have an incidence of type 2 diabetes that is higher than the general population and Americans over the age of 65 have an incidence of T2D of over 25% (see cdc.gov/diabetes/data/statistics-report/diagnosed-undiagnosed-diabetes.html). Veterans are no exception and have an incidence of T2D that is higher than average (Liu et al., *Prev. Chronic Dis.,* 2017, 14: 170230 (E135)) and with correspondingly high health care costs. The co-morbidities of type 2 diabetes, which include about a 2-fold increase in cardiovascular disease incidence as well as vascular disease and impaired wound healing, accounting for about 75,000 amputations per year in the United States.

SUMMARY

The present disclosure is based, at least in part, on the surprising discovery that engineered adipocytes comprising a disrupted Nrip1 gene decreased adiposity and liver triglycerides while enhancing glucose tolerance in obese glucose intolerant mice.

Accordingly, aspects of the present disclosure provide a composition comprising an RNA-guided nuclease (RGN) and a guide RNA (gRNA), wherein the gRNA is from 15-100 nucleotides long and comprises a sequence of at least 10 contiguous nucleotides of a target sequence within exon 4 of a nuclear receptor interacting protein 1 (Nrip1) gene.

In some embodiments, the target sequence comprises: nucleotides 596-3811, 596-3110, 665-3811, or 665-3110 within exon 4 of the Nrip1 gene; nucleotides 250, 300, 350, 400, 450, or 500 on the 5' end and nucleotides 2950, 3000, 3050, 3100, or 3110 on the 3' end within exon 4 of the Nrip1 gene; nucleotides 250, 300, 350, 400, 450, 500, or 550 on the 5' end and nucleotides 750, 800, 850, or 100 on the 3' end within exon 4 of the Nrip1 gene; nucleotides 2500, 2550, 2600, 2650, 2750, or 2800 on the 5' end and nucleotides 2950, 3000, 3050, 3100, or 3110 on the 3' end within exon 4 of the Nrip1 gene; or any of the target regions within exon 4 of the Nrip1 gene shown in Table 1, plus up to 50, 75, 100, 200, 300, 400, 500, 750, or 1000 nucleotides on either side.

In some embodiments, the gRNA is from 20-25 nucleotides long. In some embodiments, the gRNA comprises a modification. In some embodiments, the gRNA comprises a sequence selected from the group consisting of:

```
sgRNA-H4
                                     (SEQ ID NO: 16)
ACAUCAGGAAGAUUCGUAUC, sgRNA-H5
                                     (SEQ ID NO: 17)
GUCAUGUGCUGCAAGAUUAC,
or sgRNA-H6
                                     (SEQ ID NO: 18)
UUUGCAUGGUCCCUAAGAAA.
```

In some aspects, the present disclosure provides a method of making a population of mature adipose cells, the method comprising: obtaining a population of adipose progenitor cells, introducing into the population of adipose progenitor cells an engineered nuclease or an inhibitory nucleic acid targeting a nuclear receptor interacting protein 1 (Nrip1) gene to produce a population of adipose progenitor cells comprising a disrupted Nrip1 gene, and maintaining the population of adipose progenitor cells comprising the disrupted Nrip1 gene in culture under conditions sufficient to induce differentiation of the adipose progenitor cells into mature adipose cells comprising the disrupted Nrip1 gene.

In some embodiments, the adipose progenitor cells are Human Adipose Capillary Progenitor Cells (HACAPS) or primary adipose progenitor cells. In some embodiments, the mature adipose cells are white, brite, or brown adipose cells.

In some embodiments, conditions sufficient to induce differentiation comprise maintaining the adipose progenitor cells in culture in the presence of adenylate cyclase activators or adrenergic agonists to induce differentiation of the adipose progenitor cells into brite adipose cells.

In some embodiments, the engineered nuclease is a meganuclease; zinc-finger nuclease; transcription activator effector-like nuclease (TALEN); or Clustered Regularly Interspaced Short Palindromic Repeats (CRISPR) Cas RNA-guided nuclease (RGN).

In some embodiments, the engineered nuclease is a RGN and the method further comprises contacting the adipose progenitor cells with a guide RNA (gRNA) targeting the Nrip1 gene. In some embodiments, the RGN and gRNA are delivered to the progenitor cells as a ribonucleoprotein (RNP) complex. In some embodiments, the RNP complex comprises *Streptococcus pyogenes* Cas9 (SpCas9) and a gRNA comprising a sequence selected from the group consisting of:

sgRNA-H4
(SEQ ID NO: 16)
ACAUCAGGAAGAUUCGUAUC, sgRNA-H5
(SEQ ID NO: 17)
GUCAUGUGCUGCAAGAUUAC,
or sgRNA-H6
(SEQ ID NO: 18)
UUUGCAUGGUCCCUAAGAAA.

In some embodiments, the RNP complex is delivered to the adipose progenitor cells by electroporation.

In some embodiments, the inhibitory nucleic acid is an antisense oligonucleotide or single- or double-stranded RNA interference (RNAi) compound. In some embodiments, the inhibitory nucleic acid comprises one or more modifications.

In some aspects, the present disclosure provides a population of engineered adipose cells produced by any method described herein.

In some aspects, the present disclosure provides a method of treating, or reducing the risk of developing or worsening, of a condition associated with an elevated body mass index (BMI) in a subject, the method comprising administering to the subject an effective amount of the population of engineered adipose cells described herein.

In some embodiments, the subject has a BMI>25.

In some embodiments, the condition associated with an elevated BMI is selected from the group consisting of metabolic syndrome, prediabetes, type 2 diabetes, lipodystrophy, cardiovascular disease, nephropathy, neuropathy, dyslipidemia, diabetic foot syndrome (DFS), leg or foot ulcers, impaired wound healing, fatty liver disease, or a combination thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, And from the claims.

DETAILED DESCRIPTION OF THE DRAWINGS

Figure 1B:
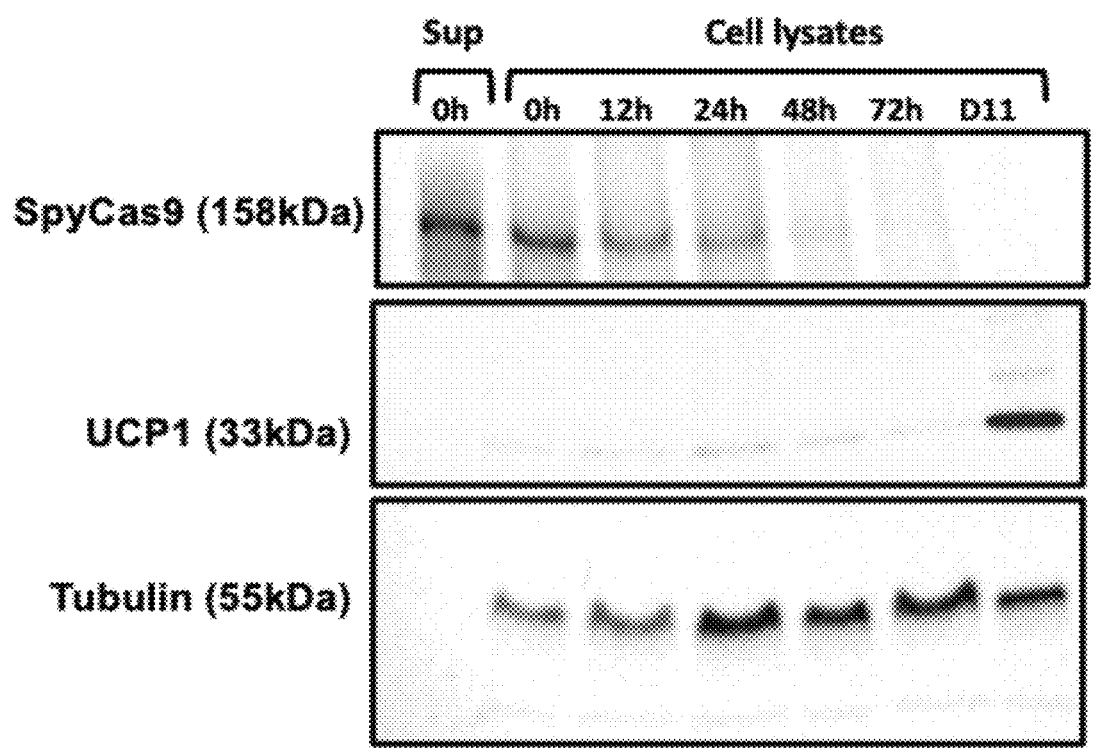
Figure 1C:
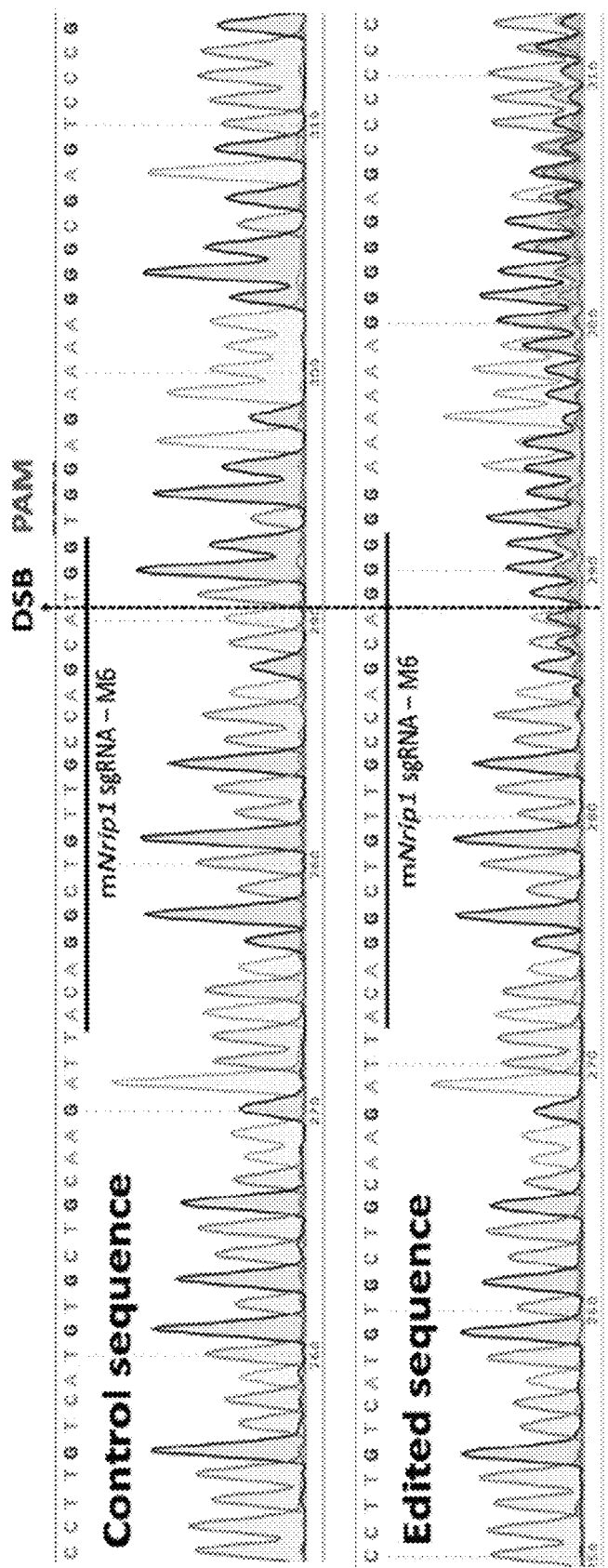
Figure 1D:
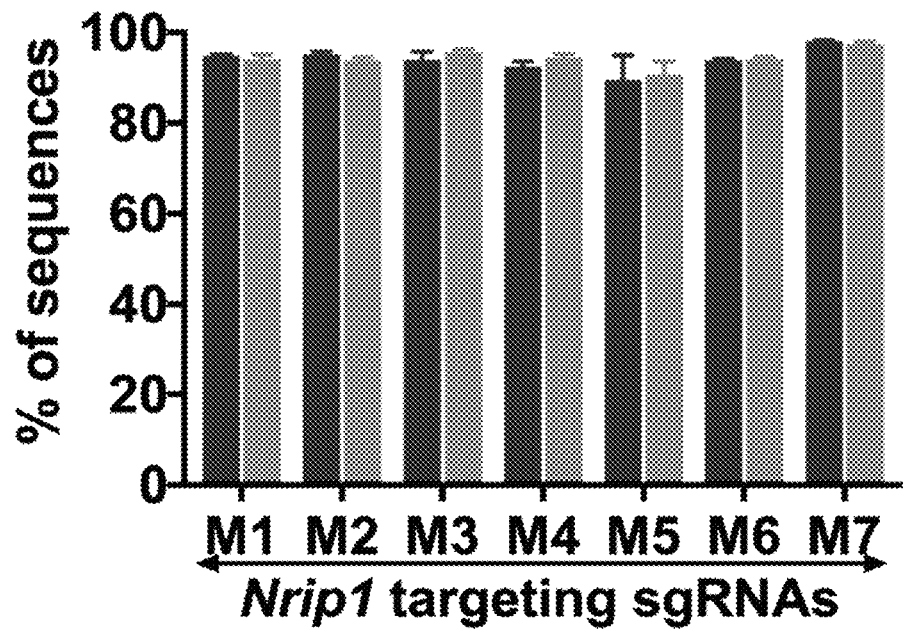
Figure 1E:
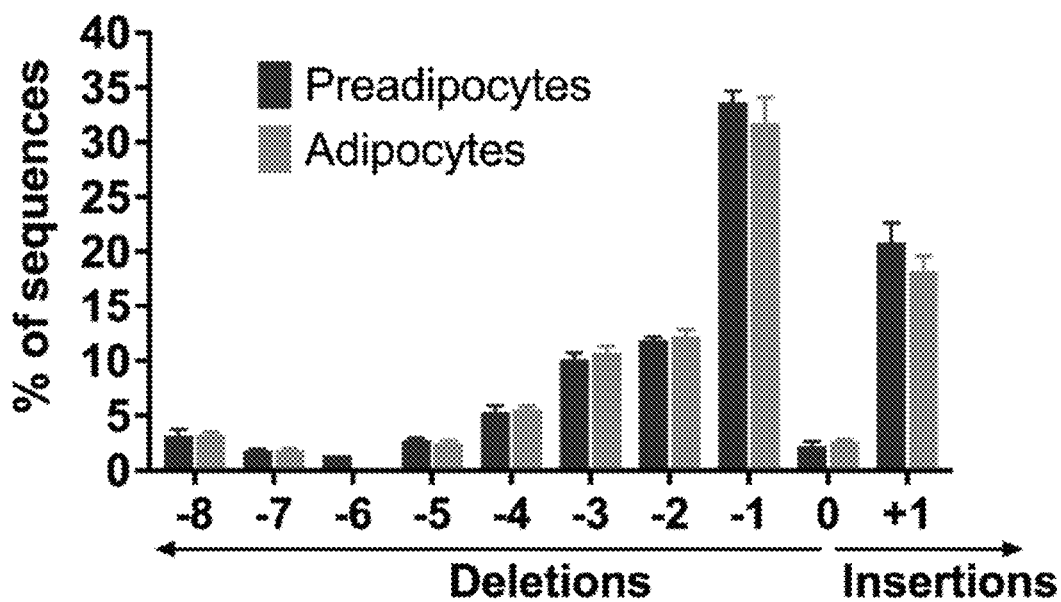
Figure 1F:
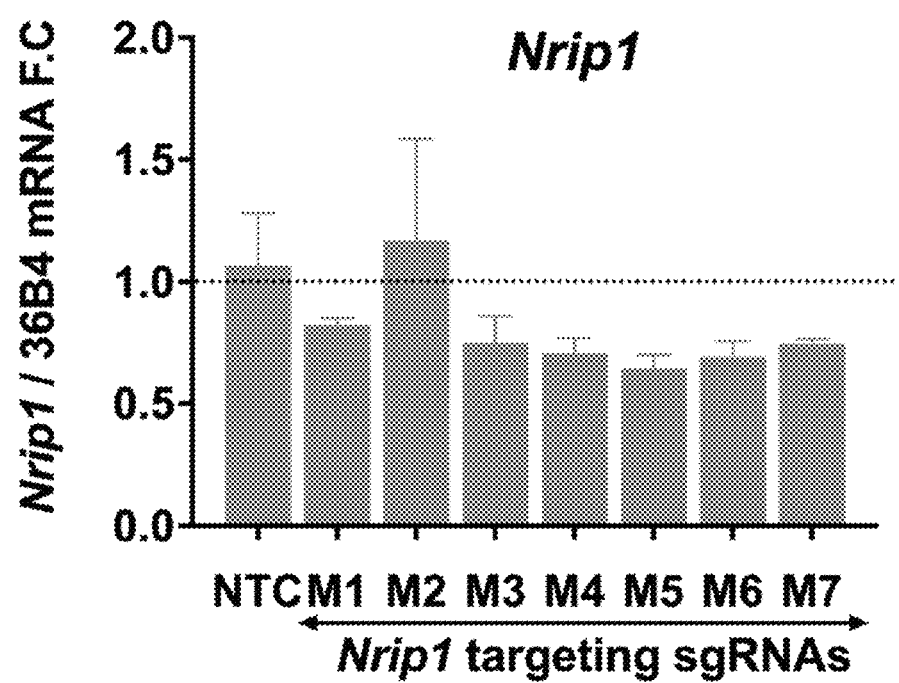
Figure 1G:
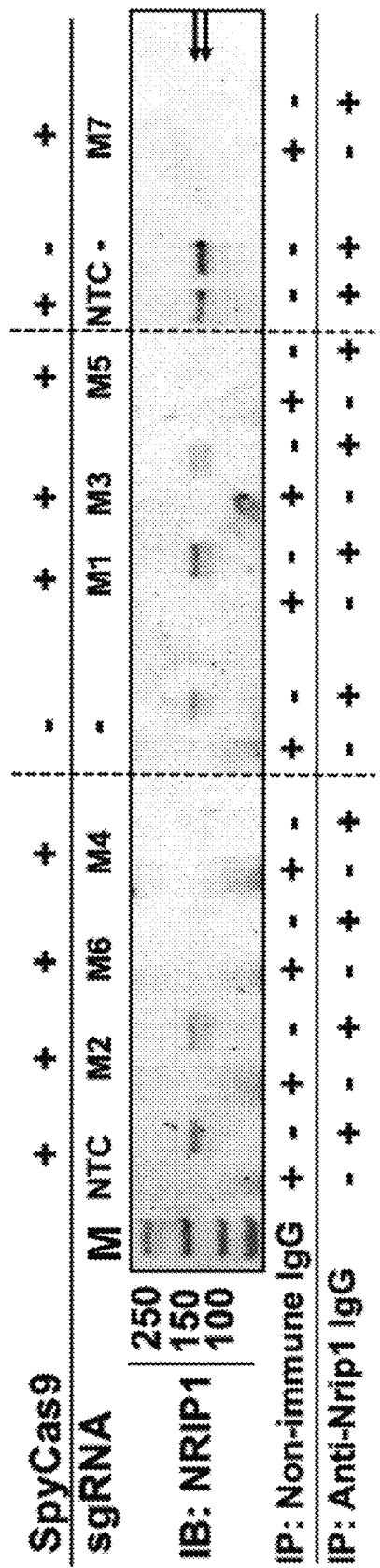
Figure 1H:
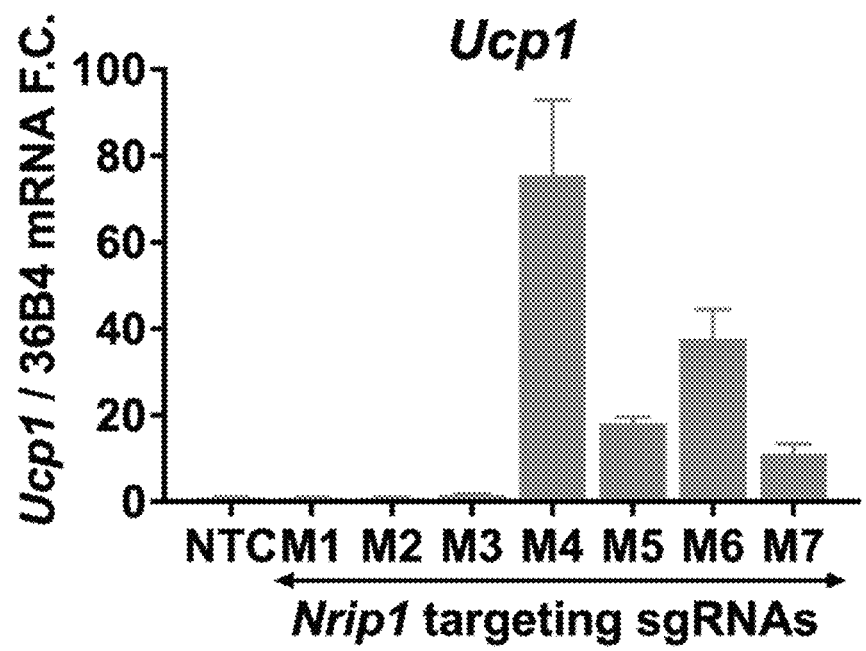
Figure 1I:
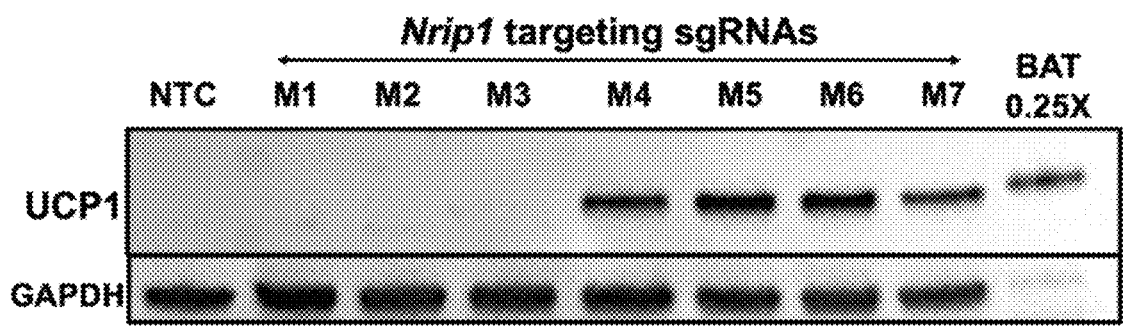

FIGS. 1a-1i: High efficiency Nrip1 gene disruption at 7 loci by SpyCas9/sgRNA RNPs produces variable degrees of NRIP1 protein loss and UCP1 upregulation in murine primary adipocytes. FIG. 1a: Mapping of the sgRNAs M1-M7 targeting various loci of murine Nrip1 coding region which is entirely located in exon 4 (TSS=transcription start site; STOP=stop codon). FIG. 1b: Time-course of SpyCas9 protein degradation detected by Western Blotting in cell lysates at various time points (0-72 hours and day 11 after transfection, which is day 6 of differentiation) after electroporation with RNPs of SpyCas9:sgRNA (3:4 µM). Sup denoted supernatant containing SpyCas9 at 0 hours. FIG. 1c: Sanger sequencing traces of control vs Nrip1 disrupted cells with sgRNA-M6 showing the sgRNA binding site (solid black line), PAM (gray), the double-strand-break (denoted as DSB) site (dashed black line) on the sgRNA-M6 targeting locus and the traces downstream of the DSB created by the DNA repair mechanisms (figure created with SnapGene). The control sequence comprises nucleotides 1048-1110 of SEQ ID NO: 20. The edited sequence is provided as SEQ ID NO: 23. FIG. 1d: Editing efficiency as evaluated with indel percentage 72 hours after the transfection of primary preadipocytes (black) and differentiation to mature primary adipocytes (gray). FIG. 1e: Indel distribution of Nrip1 sgRNA-M6 with frameshift indels that are sustained after differentiation. FIG. 1f: Nrip1 gene expression detected by RT-PCR in mature adipocytes targeted with the different sgRNAs. FIG. 1g: Immunoprecipitation assay for NRIP1 (140 kDa, arrows at right) in mature primary adipocytes on day 6 post differentiation targeted with the different sgRNAs. The total lysate protein amount used in the assay was 250 µg per sample. M denotes molecular weight marker. FIG. 1h: Ucp1 expression by RT-PCR in mature adipocytes targeted with the different sgRNAs compared to non-targeted control cells. FIG. 1i: Western blot for UCP1 protein (33 kDa) in mature adipocytes on day 6 post differentiation targeted with the different sgRNAs. Lanes 1-8 were loaded with 20 µg of total protein while lane 9 was loaded with 5 µg of total protein isolated from mouse BAT. NTC=Non-targeting control. In FIG. 1b and FIG. 1c error bars denote Mean±S.E.M. In FIG. 1e and FIG. 1g, bars denote mean, error bars denote mean±standard deviations, n>3 biological replicates.

Figure 2A:
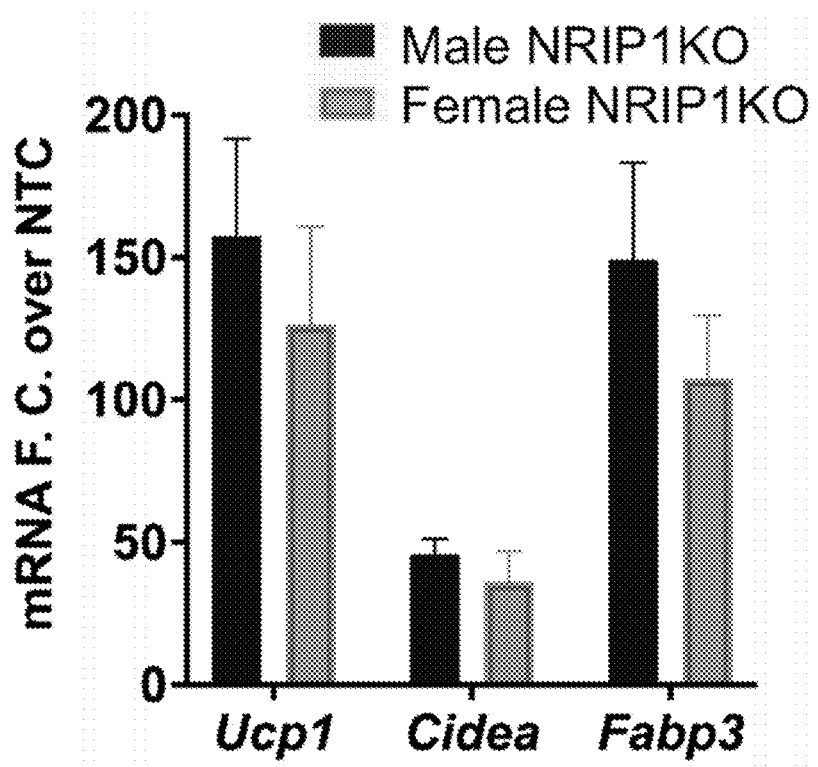
Figure 2B:
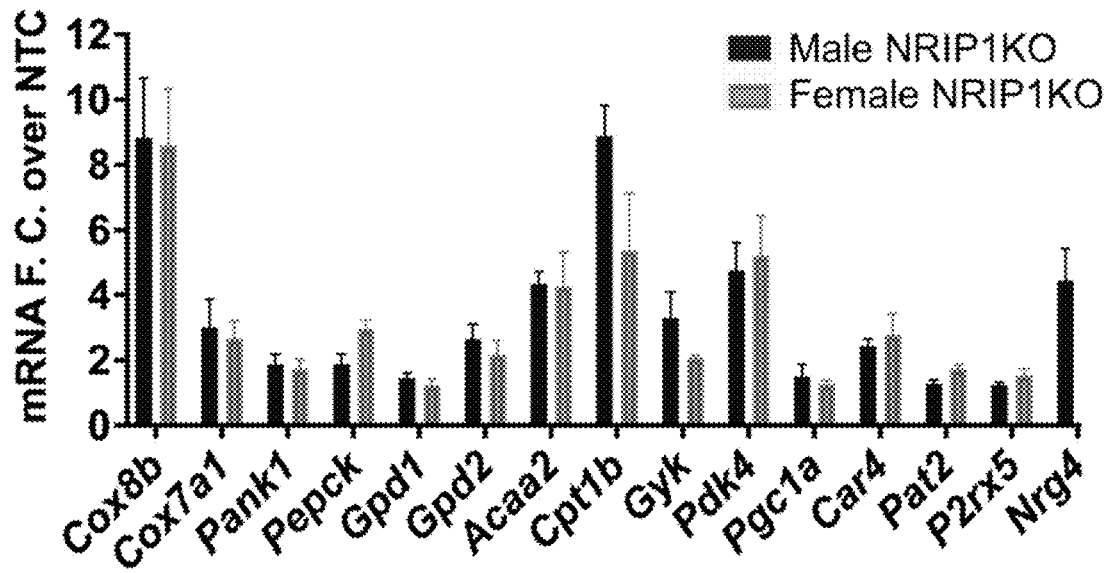
Figure 2C:
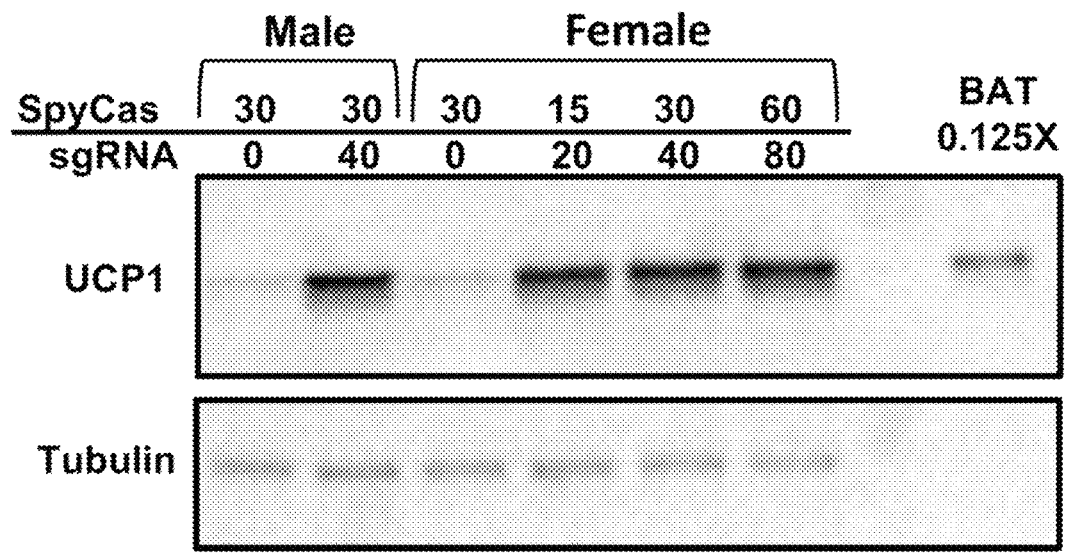
Figure 2D:
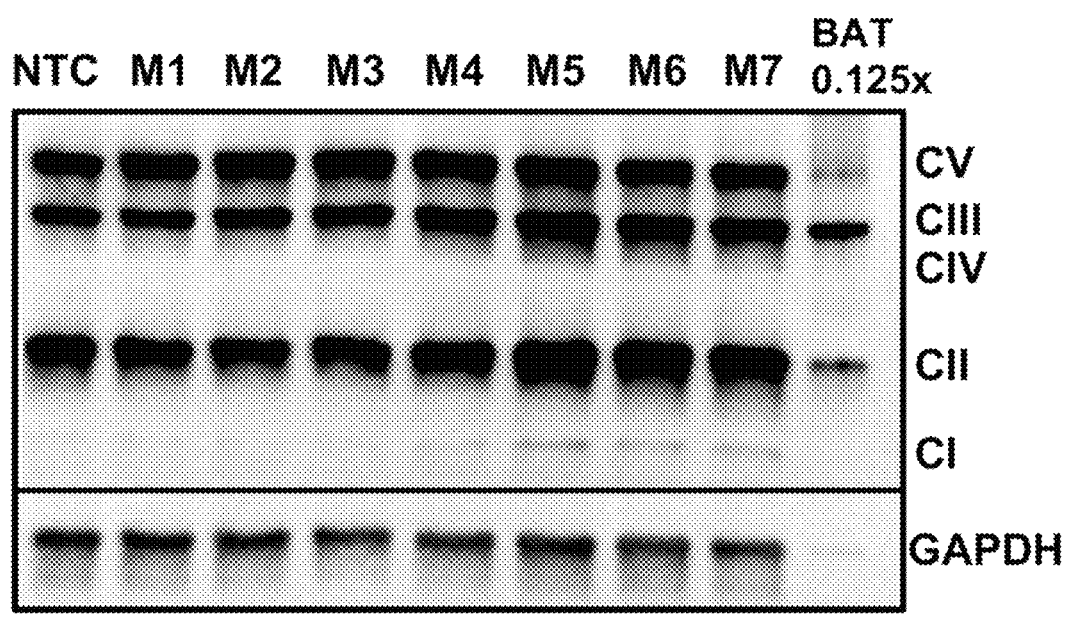
Figure 2E:
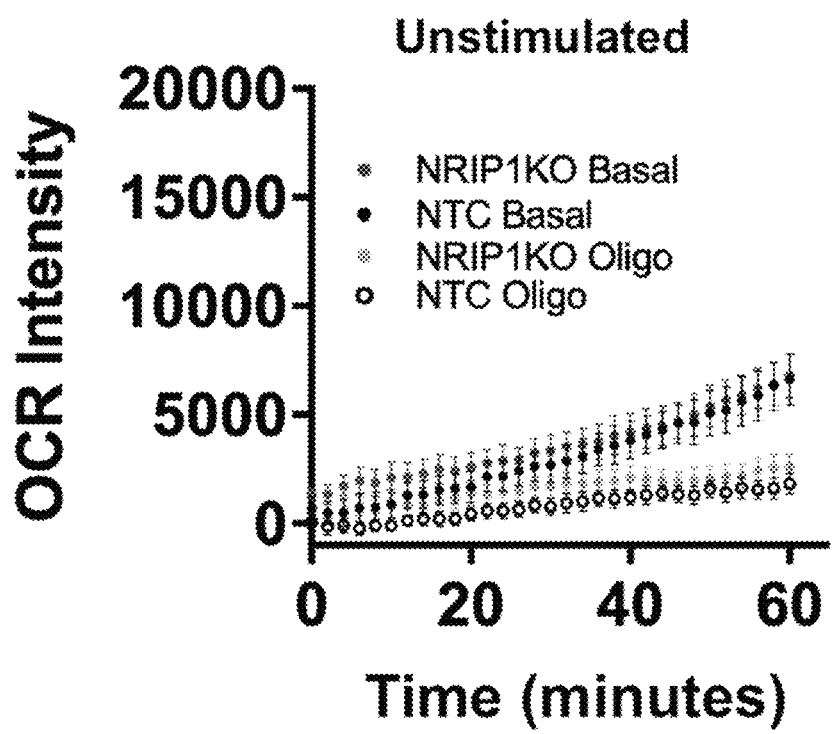
Figure 2F:
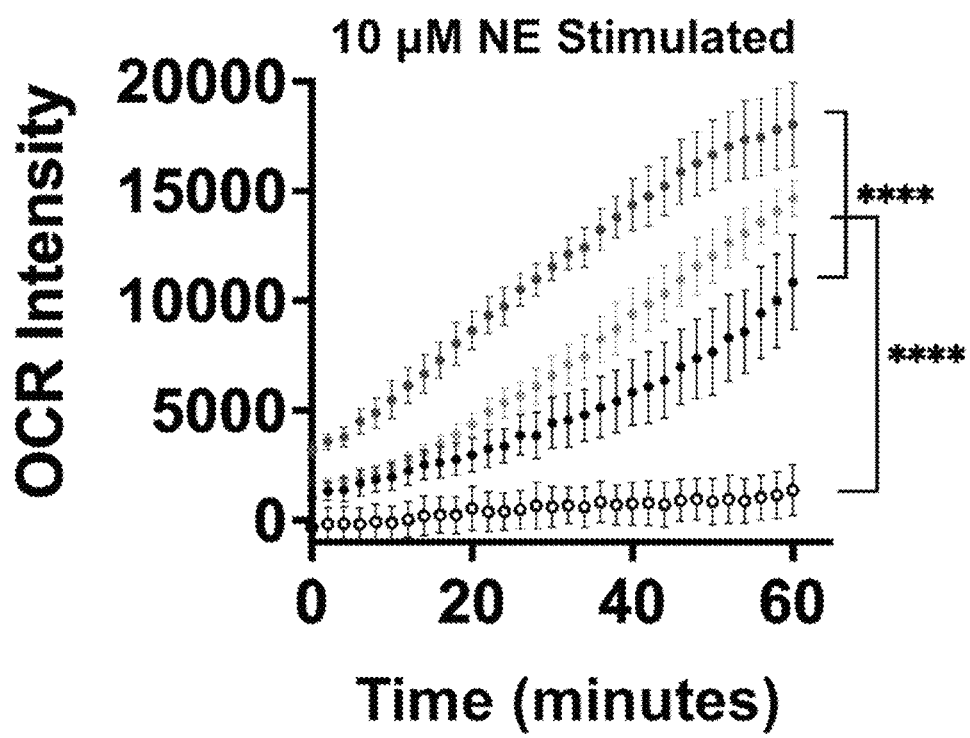
Figure 2G:
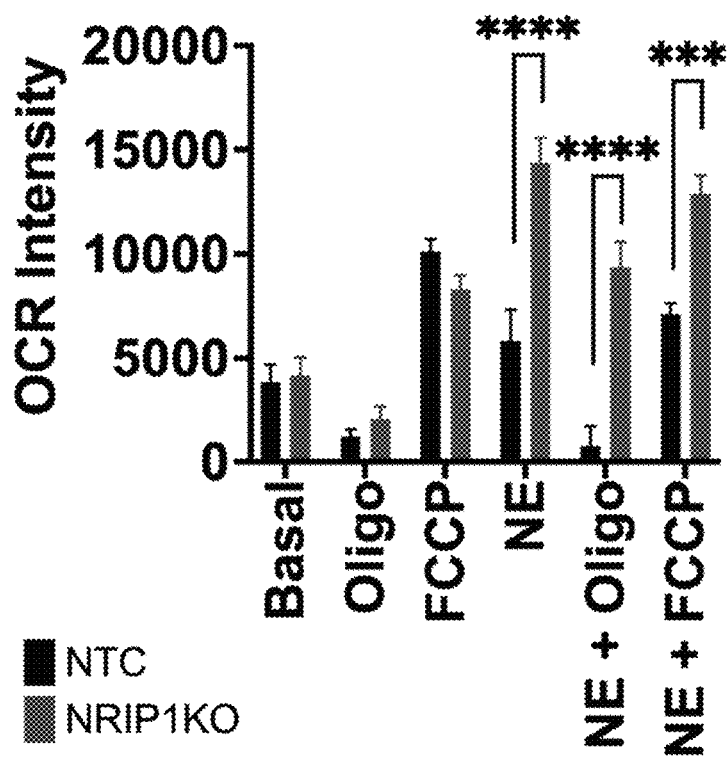
Figure 2H:
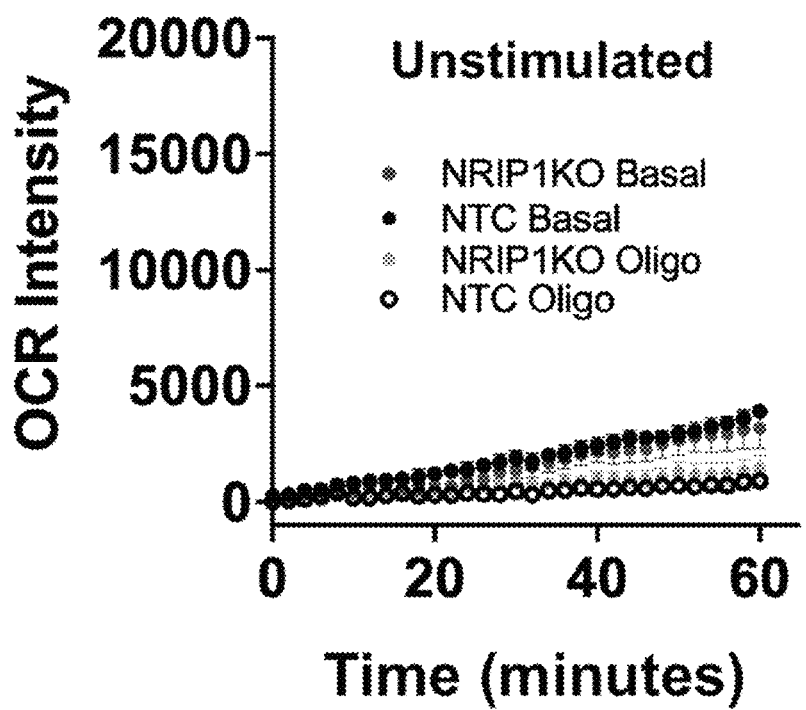

FIGS. 2a-2j: Primary mouse NRIP1KO adipocytes from both male and female mice display increased thermogenic gene expression and uncoupled oxygen consumption. FIGS. 2a-2b: gene expression profiles detected by RT-PCR in mature primary male and female mouse adipocytes. Ucp1, Cidea and Fabp3 gene expression (FIG. 2a) and gene expression in the thermogenic, oxidative phosphorylation and fatty acid oxidation pathways (FIG. 2b). Gene expression represents the fold change over NTC. In FIGS. 2a-2b, male=black (n=3), female=gray (n=3). Error bars denote mean±SEM. FIG. 2c: UCP1 (33 kDa) protein expression in primary male and female adipocytes, 6 days post differentiation in cells with various RNP concentrations. Lanes 1 to 6 contain 20 µg of total protein lysate and lane 8 contains 2.5 µg of total protein from mouse BAT. Tubulin is shown as a loading control. FIG. 2d: Oxidative phosphorylation protein expression in primary male adipocytes on day 7 post differentiation targeted with NTC or NRIP1 sgRNA-M1-M7. Lanes 1 to 8 contain 20 µg of total protein while lane 9 contains 2.5 µg of total protein isolated from mouse BAT. GAPDH is shown as a loading control. FIG. 2e: Oxygen consumption rates (OCR) in basal and ATP-linked mitochondrial respiration from mature primary male adipocytes targeted with NTC or NRIP1 sgRNA-M6 without norepinephrine stimulation and FIG. 2f with norepinephrine stimulation. Statistical comparison for OCR was done for FIGS. 2e-2f using one-way ANOVA with Sidak's multiple comparison test. **$p<0.0001$ FIG. 2g: Summary of oxygen consumption parameters at 40 min in primary male adipocytes with and without norepinephrine stimulation. Statistical comparison for FIG. 2g was done using two-way ANOVA with Sidak's multiple comparison test. $p<0.0001$, *$p=0.0009$. FIG. 2h: Oxygen consumption rates in basal and ATP-linked mitochondrial respiration from mature primary female adipocytes targeted with NTC or NRIP1 sgRNA-M6 without norepinephrine stimulation and FIG. 2i with norepinephrine stimulation. Statistical comparison for OCR was done for FIGS. 2h-2i using one-way ANOVA with Sidak's multiple comparison test. **p<0.0001 FIG. 2j: Summary of oxygen consumption parameters at 40 minutes in primary female adipocytes with and without norepinephrine stimulation. Statistical comparison for FIG. 2j was done using two-way ANOVA with Sidak's multiple comparison test. NE p=0.0034, NE+Oligo **p=0.0059, NE+FCCP *p=0.0399.

Figure 3A:
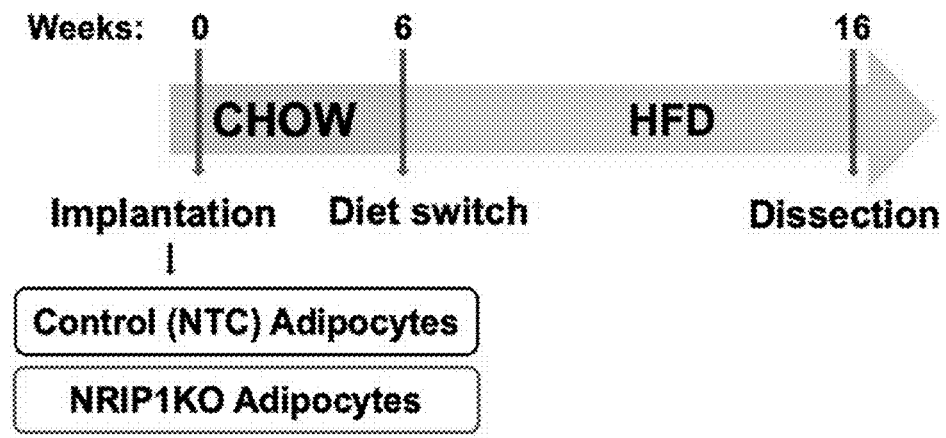
Figure 3B:
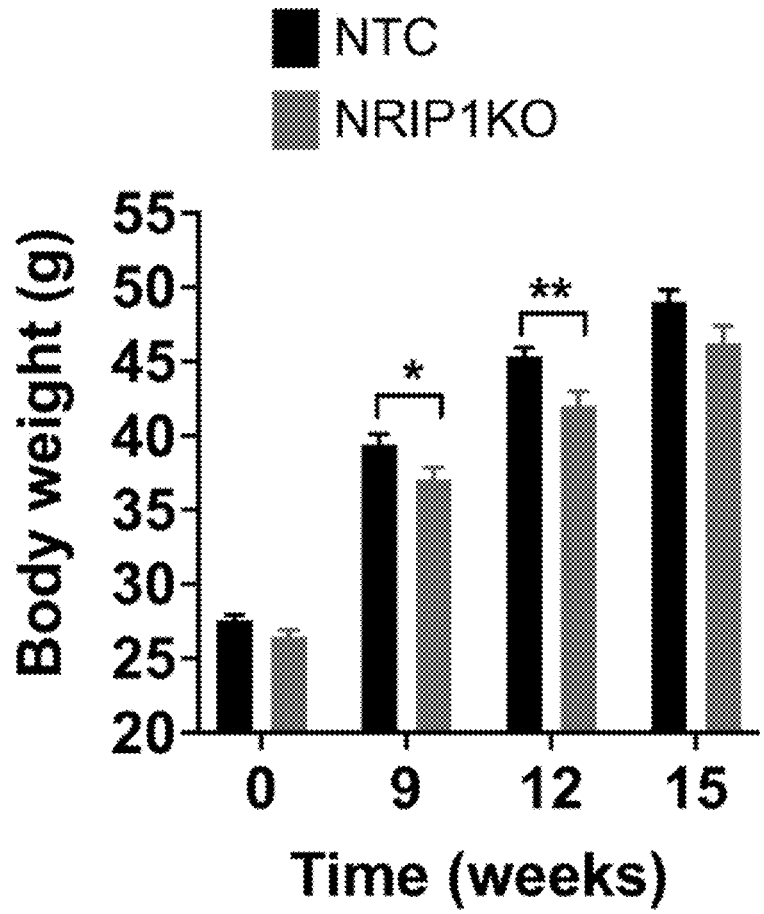
Figure 3C:
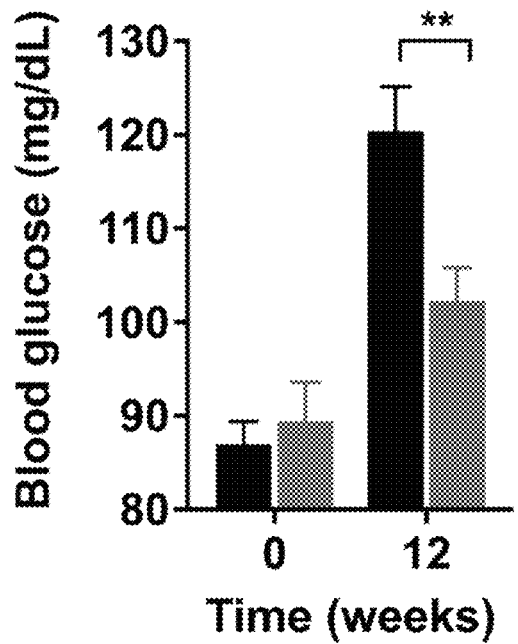
Figure 3D:
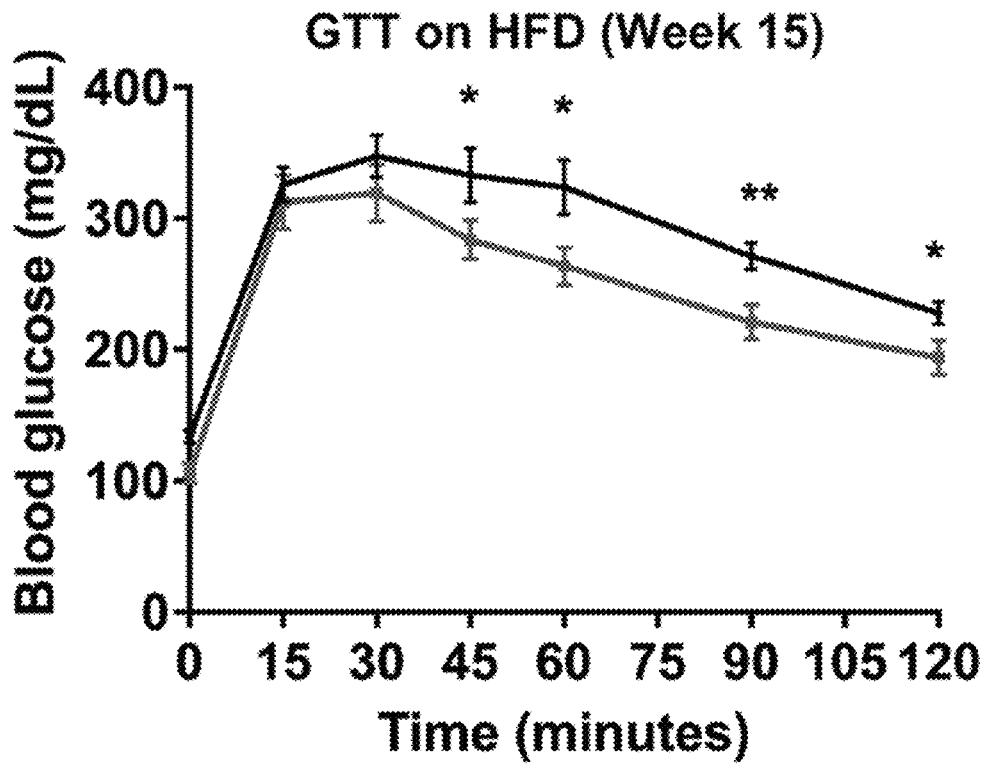
Figure 3E:
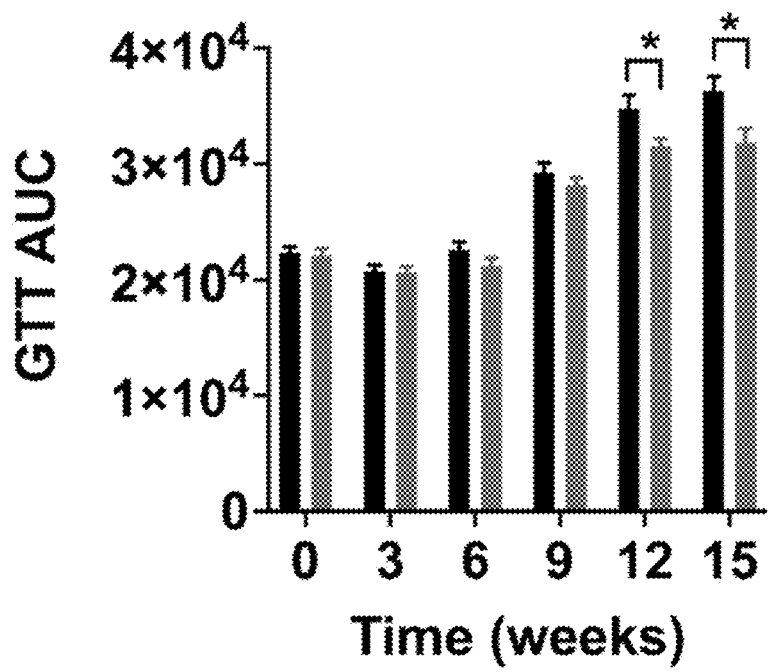
Figure 3F:
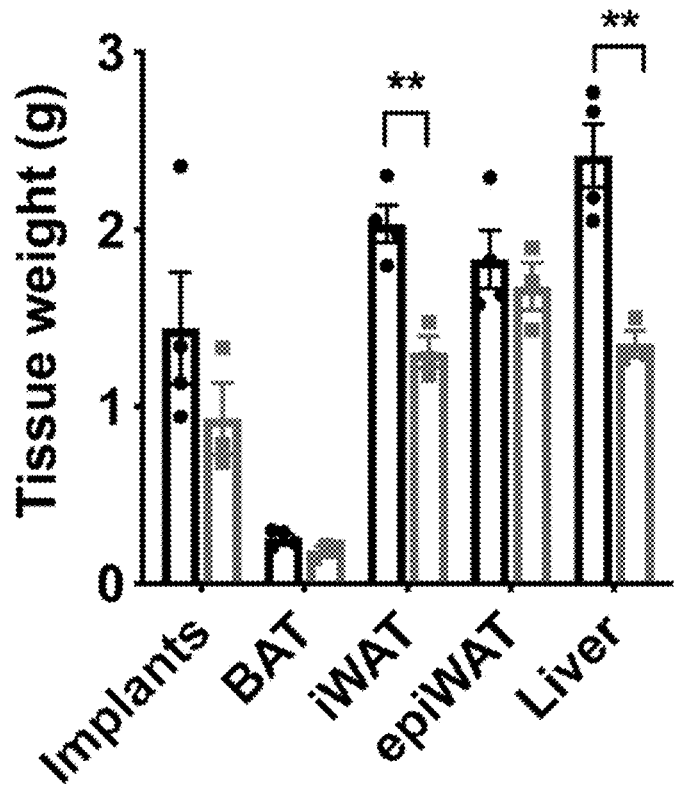
Figure 3G:
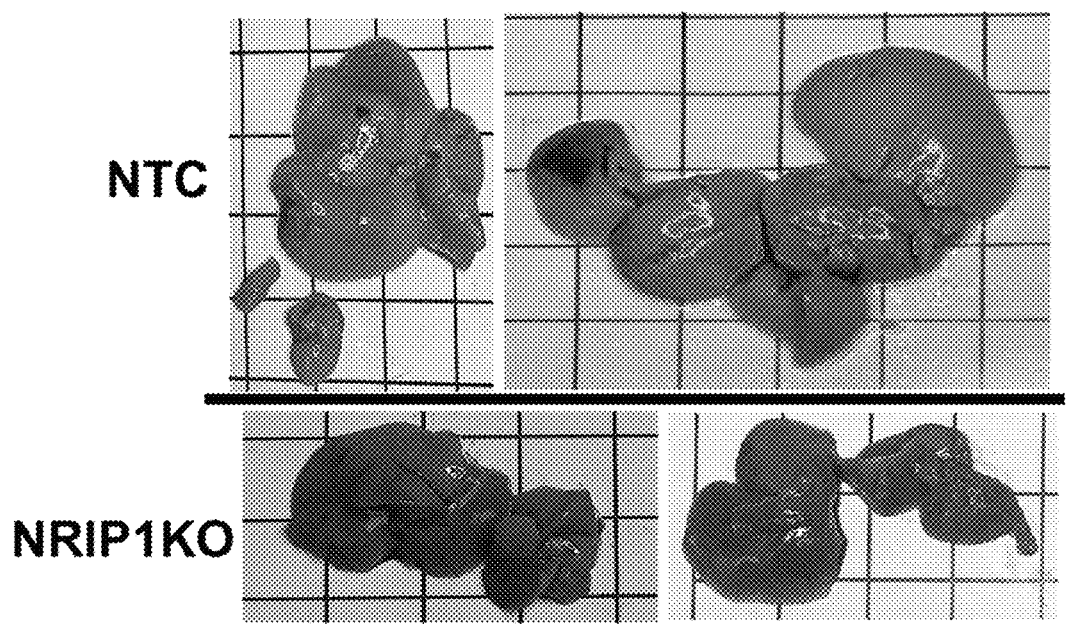
Figure 3H:
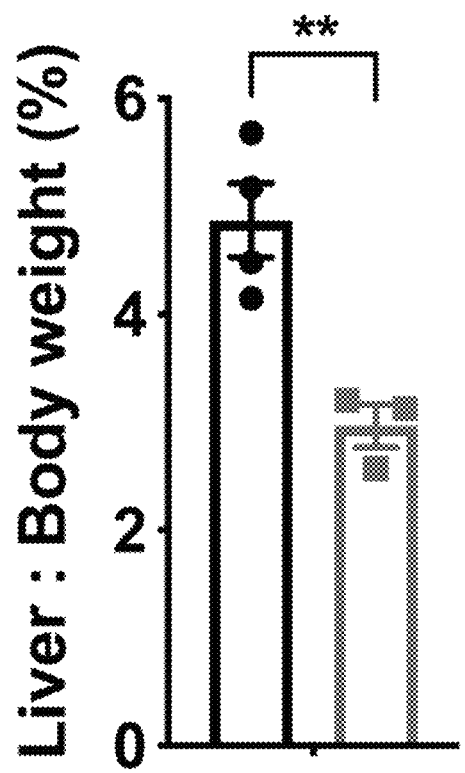
Figure 3I:
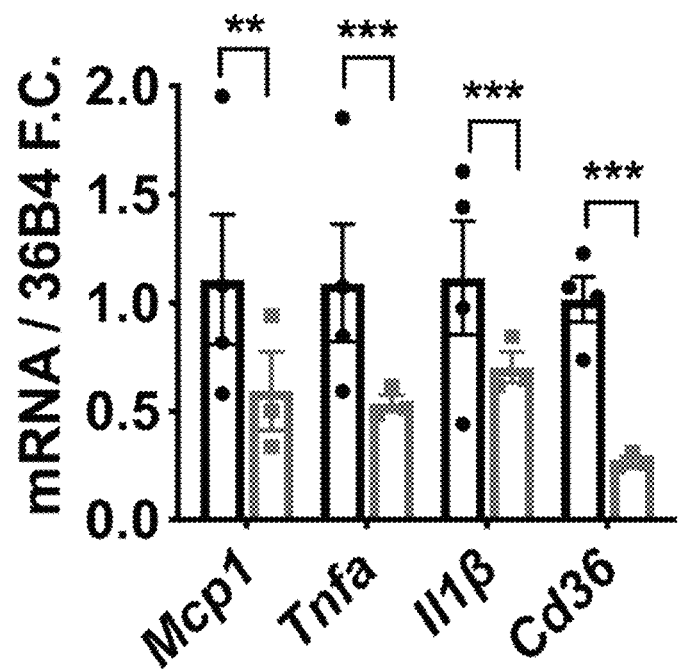
Figure 3J:
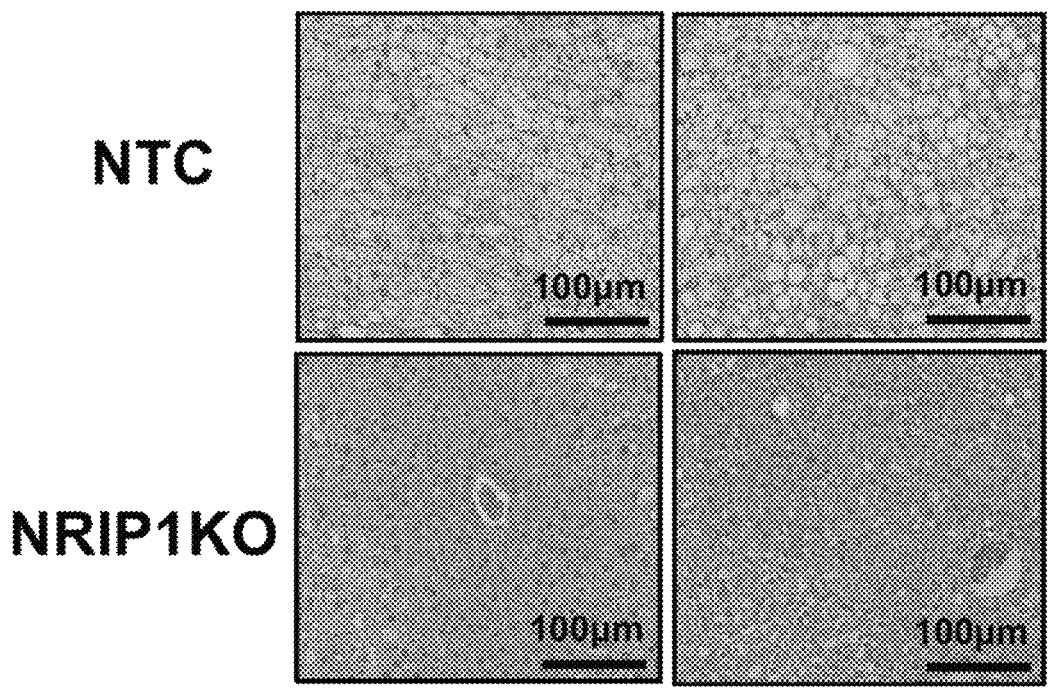
Figure 3K:
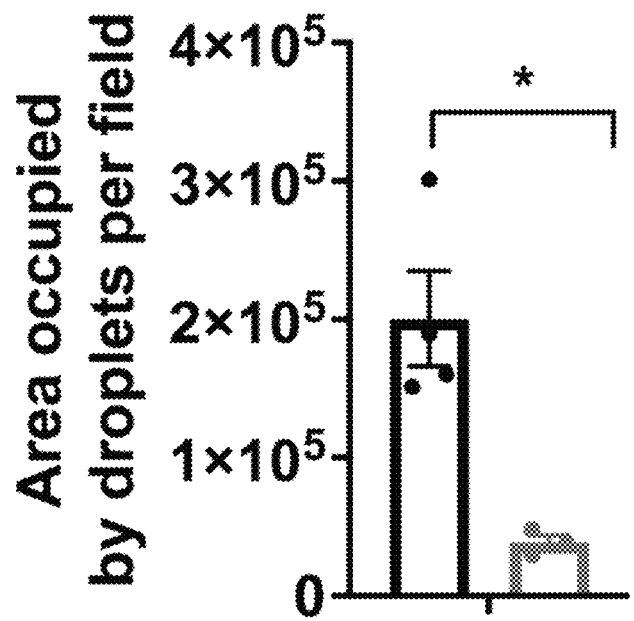
Figure 3L:
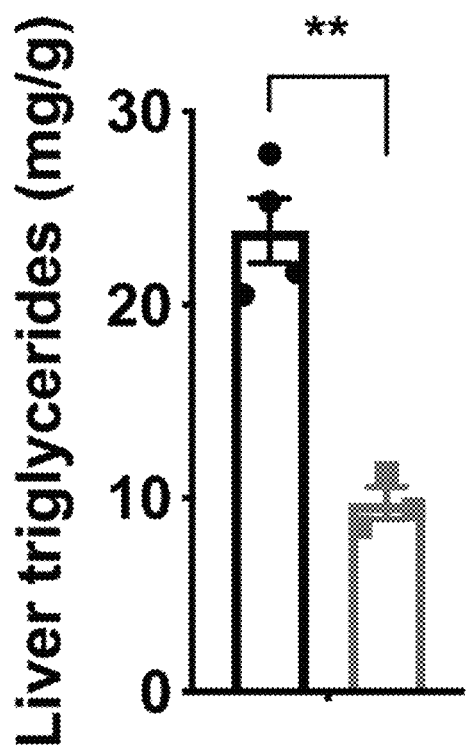

FIGS. 3a-3l: Implantation of NRIP1-depleted mouse adipocytes improves glucose tolerance and markedly decreases iWAT weight and liver triglyceride accumulation in recipient mice. Mice were implanted with either mouse adipocytes previously transfected with NTC sgRNA/Cas9 RNPs or with sgRNA-M6/Cas9 RNPs (NRIP1KO). FIG. 3a: Schematic protocol of implantation of murine NTC adipocytes or NRIP1KO adipocytes into C57BL/6 wild type mice followed by 60% kCal fat diet (HFD). FIG. 3b: Total body weights of recipients on chow before implantation and 6, 9, 12, 15 weeks after implantation on HFD. P values *9 weeks=0.034; **12 weeks=0.008; 15 weeks=0.058 FIG. 3c: Fasting blood glucose concentrations at baseline (p=0.626) and 12 weeks (p=0.005) post implantation (6 weeks on HFD). FIG. 3d: Glucose tolerance test (GTT) after 16-hour overnight fasting in implant recipients after 9 weeks on HFD. P values *45 min=0.015; *60 min=0.011; **90 min=0.004; *120 min=0.022 FIG. 3e: Bar graphs of areas under the curve from GTTs in implant recipient mice on chow and after 9, 12 and 15 weeks on HFD. P values *12 weeks=0.022; *15 weeks=0.016. FIG. 3f: Weight of total bilateral implants, whole BAT, total bilateral iWAT, epiWAT and total liver as measured after dissection. P values iWAT=0.004; Liver=0.005. FIG. 3g: Macroscopic images of the whole livers of the implant recipients after dissection (square=1 cm$^2$). FIG. 3h: Liver over whole body weight percentage. p value=0.008. FIG. 3i: Expression of genes related to inflammation and hepatic steatosis in the livers of implant recipients detected by RT-PCR. P values *Mcp1=0.047; *Tnfα=0.0001; Il1b=0.004; ****Cd36=0.0000320. FIG. 3j: Hematoxylin and eosin (H&E) stain on liver histology of the implant recipients at 20× magnification. FIG. 3k: Quantification of total H&E images of implant recipients' livers for total area occupied by lipid droplets per field (p value=0.011). FIG. 3l: Triglyceride measurements in pulverized liver extracts after dissection. (p value=0.001). black=NTC adipocyte implant recipients, gray=NRIP1KO adipocyte implant recipients; in FIGS. 3b-3e: NTC (n=13); NRIP1KO (n=14), in FIGS. 3f-3l: NTC (n=4); NRIP1KO (n=3). Bars represent the mean. Error bars denote mean±SEM. *p<0.05, p<0.01, *p<0.001 by unpaired two-tailed T-test.

Figure 4A:
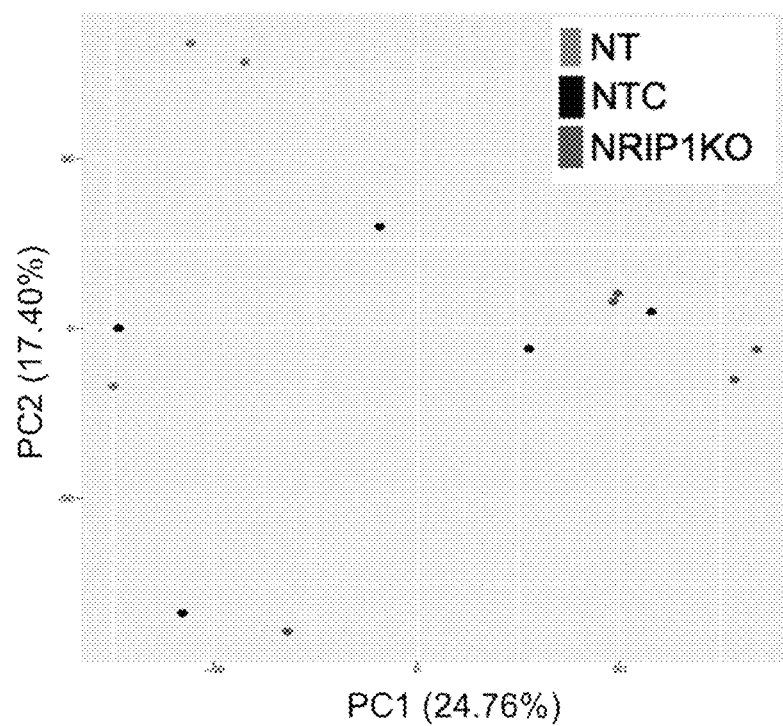
Figure 4B:
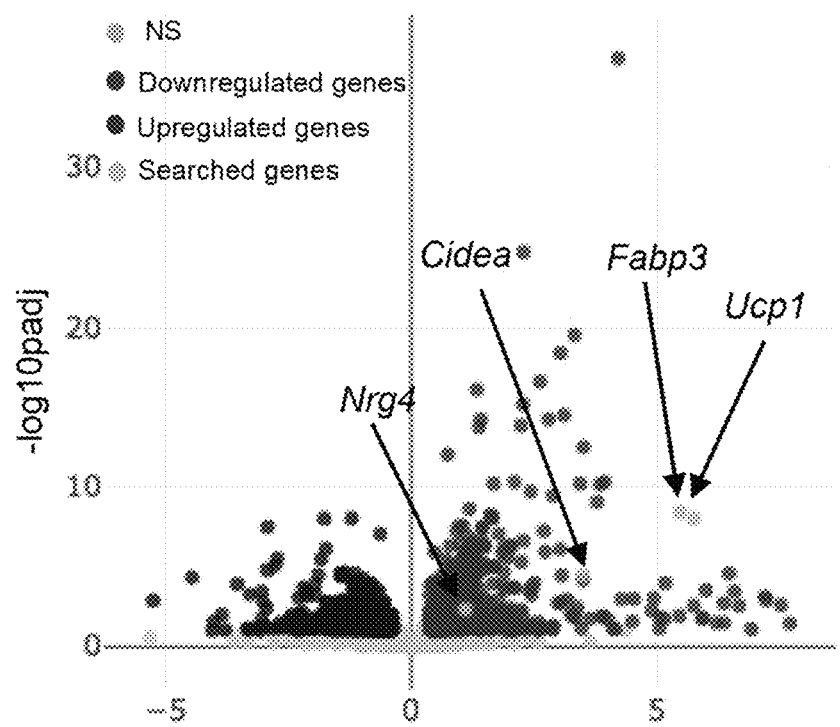
Figure 4C:
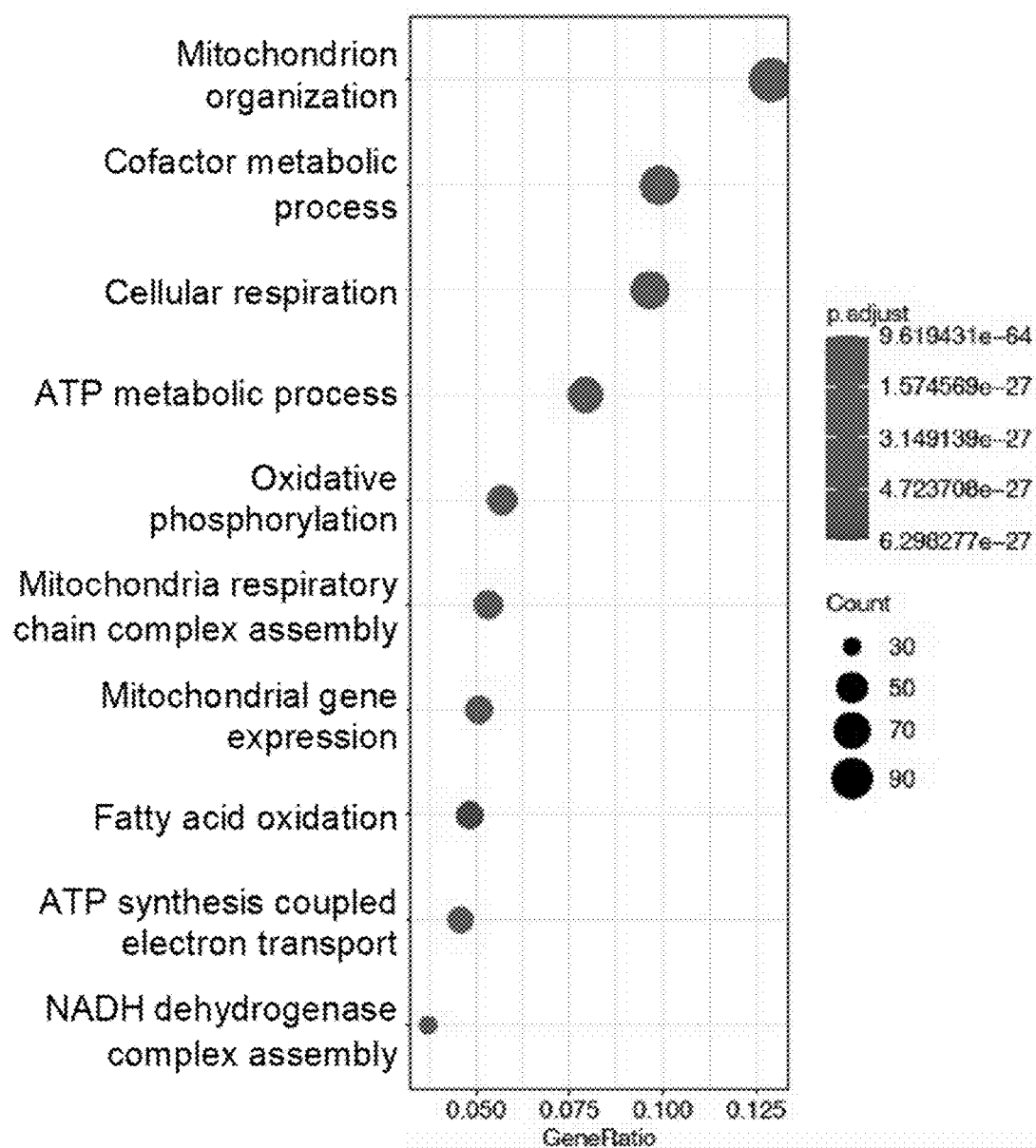
Figure 4D:
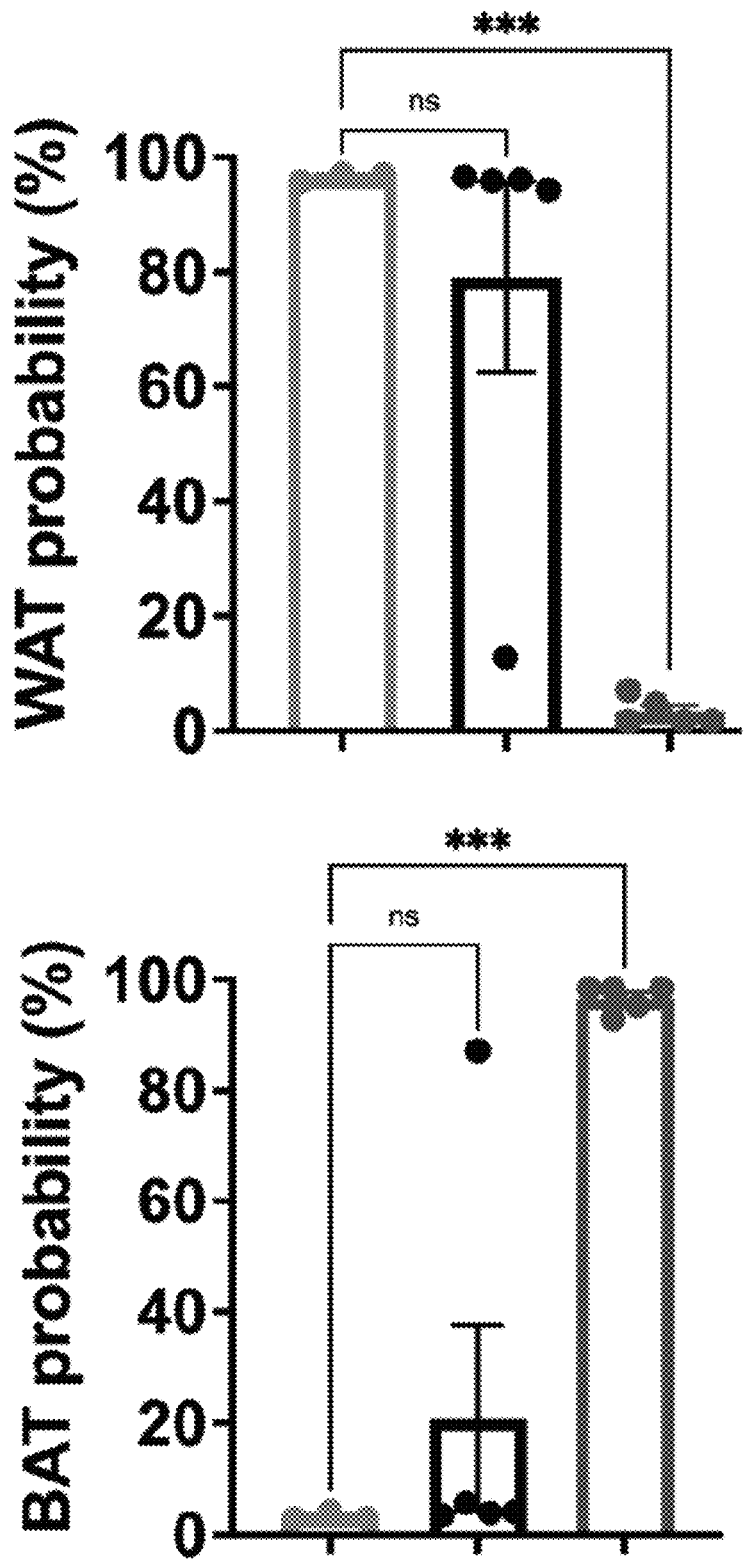
Figure 4E:
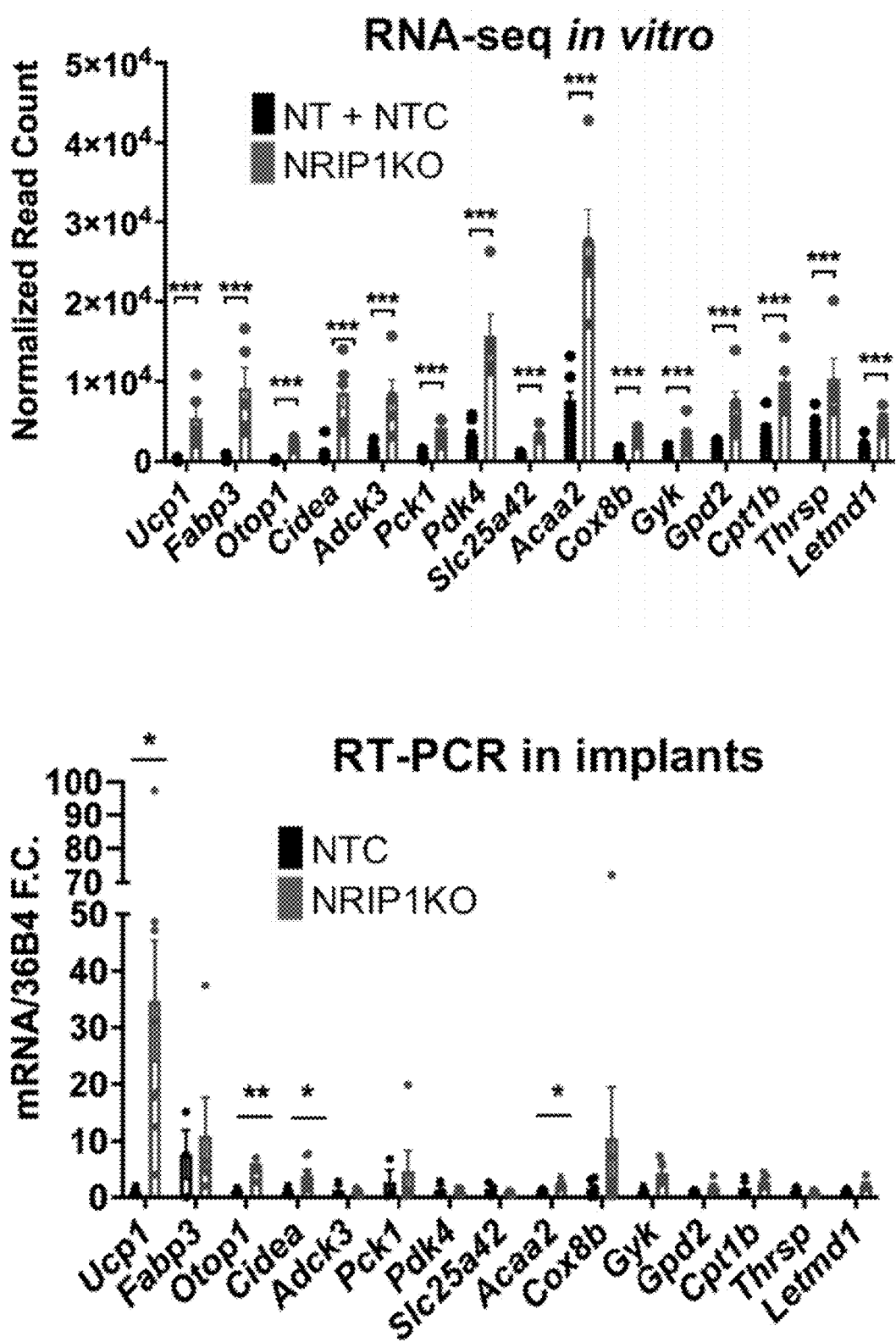

FIGS. 4a-4e: RNA sequencing on non-treated, NTC and NRIP1KO mature adipocytes on day 6 after differentiation. FIG. 4a: Principal component plot prior to DEseq analysis. FIG. 4b: Volcano plot of upregulated (gray) and downregulated (black) genes between control unedited adipocytes (NT and NTC) and NRIP1KO adipocytes with highlighted (light gray) Ucp1, Cidea, Fabp3, Nrg4. FIG. 4c: Top 10 pathways associated with all upregulated genes detected. FIG. 4d: Browning probability calculated using the ProFAT online tool. p=0.0004 by One-way ANOVA. FIG. 4e: Top: top 15 upregulated genes by RNA sequencing where all NRIP1KO samples have >1000 normalized reads and padj>0.1 (Black=NTC+NT) and NT, Gray=NRIP1KO). Bottom: Screening of these 15 genes in the excised implant NTC (black) or NRIP1KO (red) tissue by RT-PCR. P values *Ucp1=0.018; **Otop1=0.006; *Cidea=0.021; *Acaa2=0.041 by unpaired two-tailed T-test. Cut-offs were set at padj<0.1 and fold change>1.3. NT (n=3), NTC (n=5), NRIP1KO (n=5). NRIP1KO adipocytes were transfected with SpyCas9 and either Nrip1 sgRNA-M4 or sgRNA-M6.

Figure 5A:
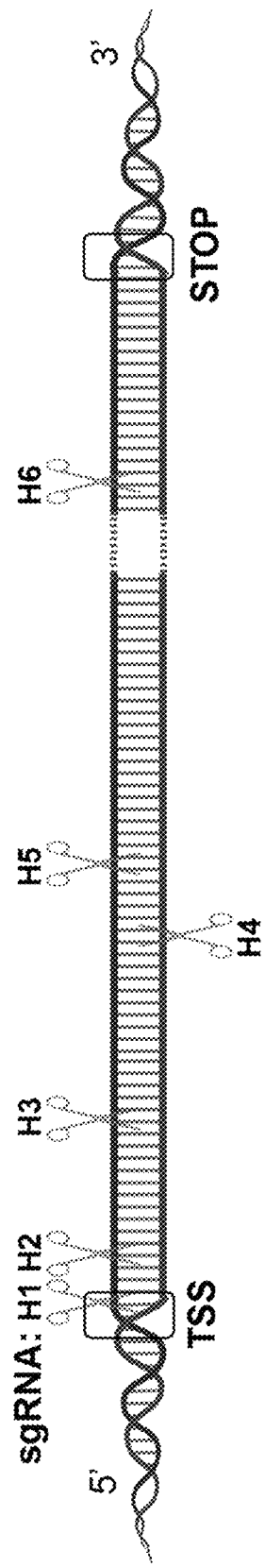
Figure 5B:
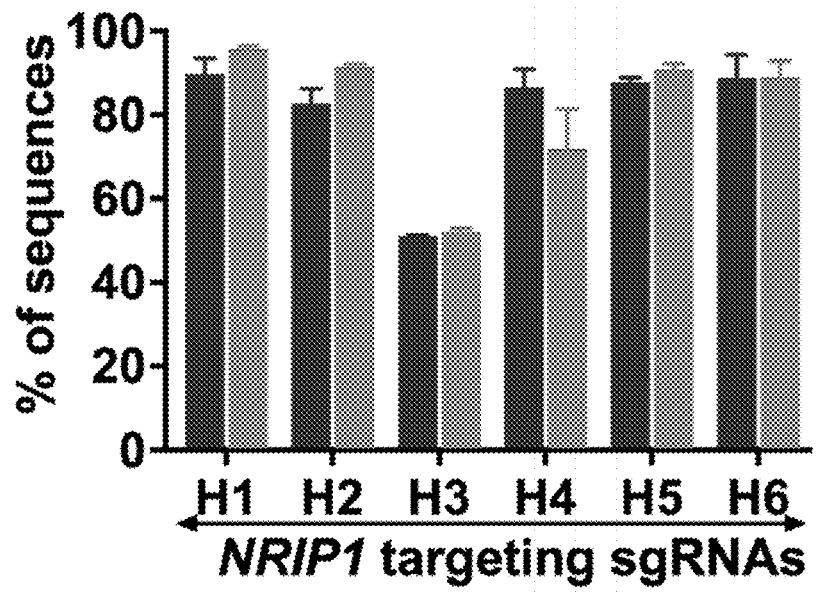
Figure 5C:
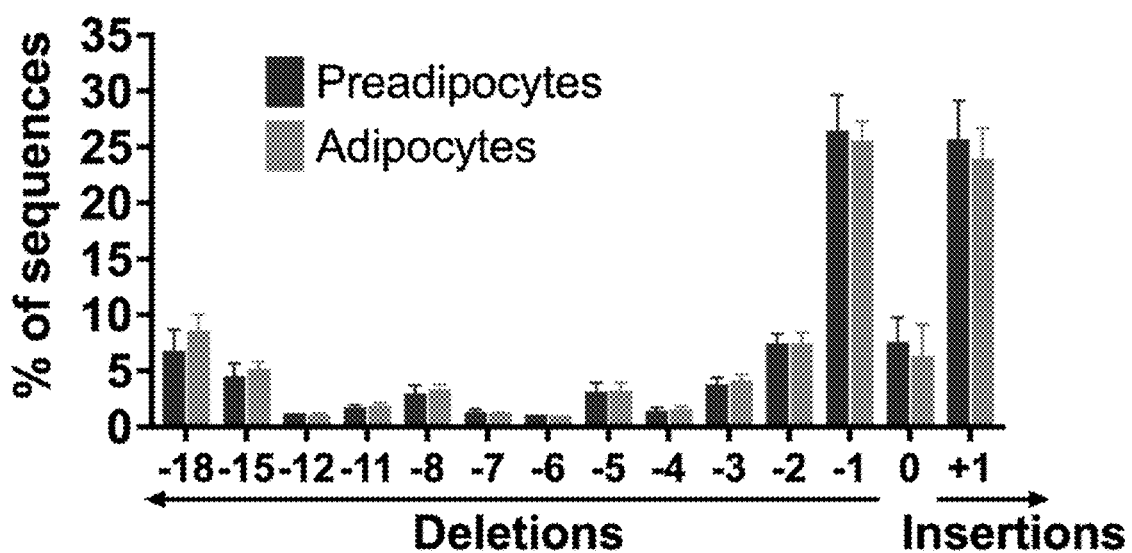
Figure 5D:
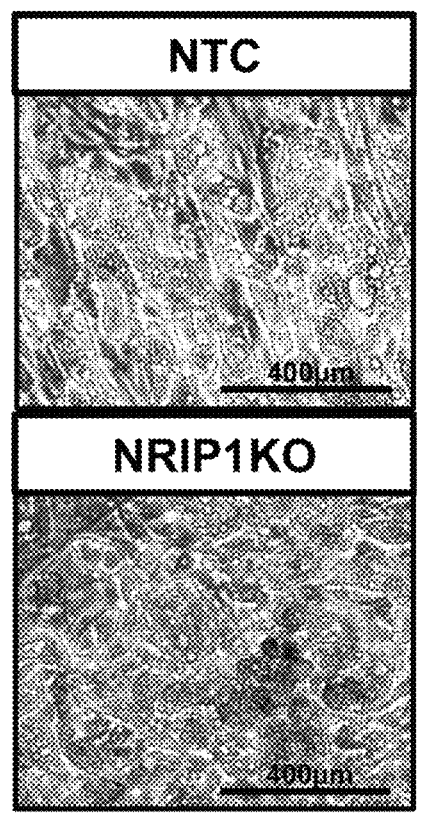
Figure 5E:
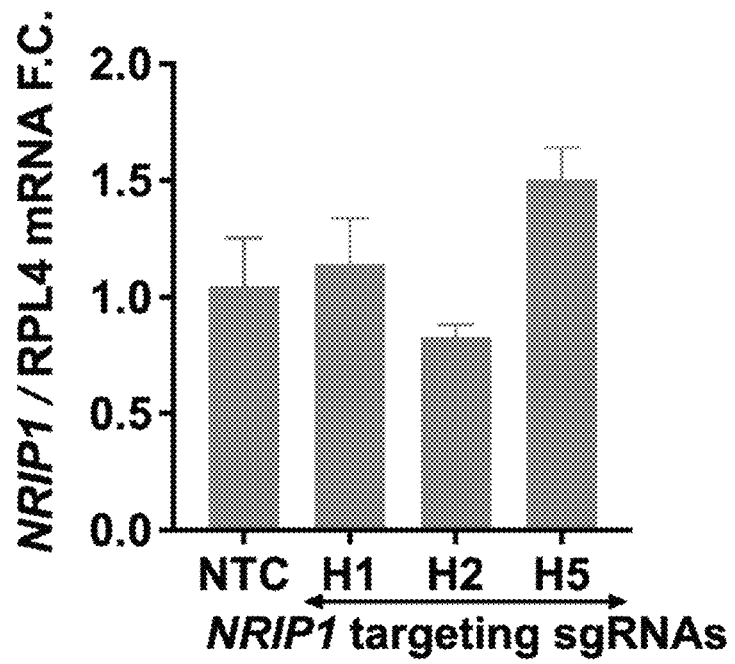
Figure 5F:
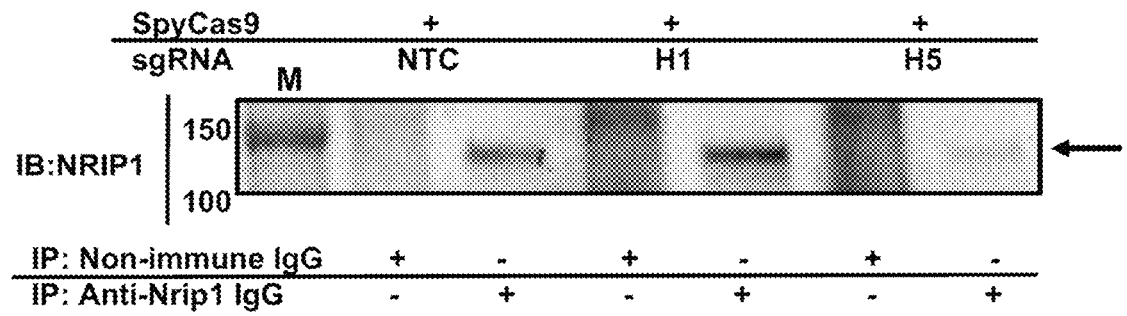
Figure 5G:
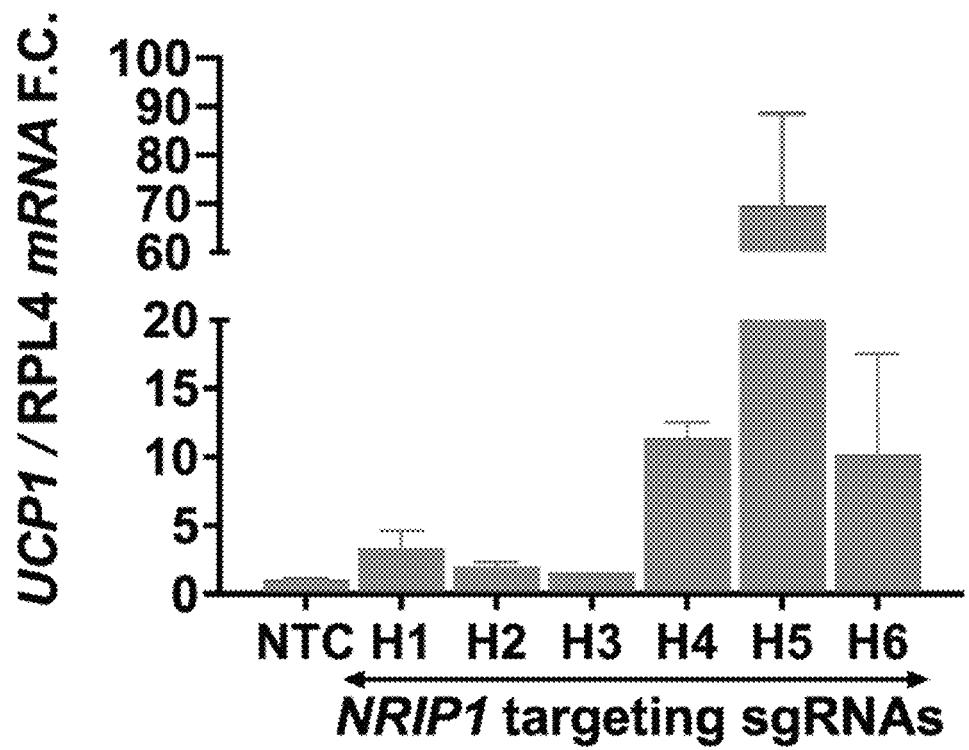
Figure 5H:
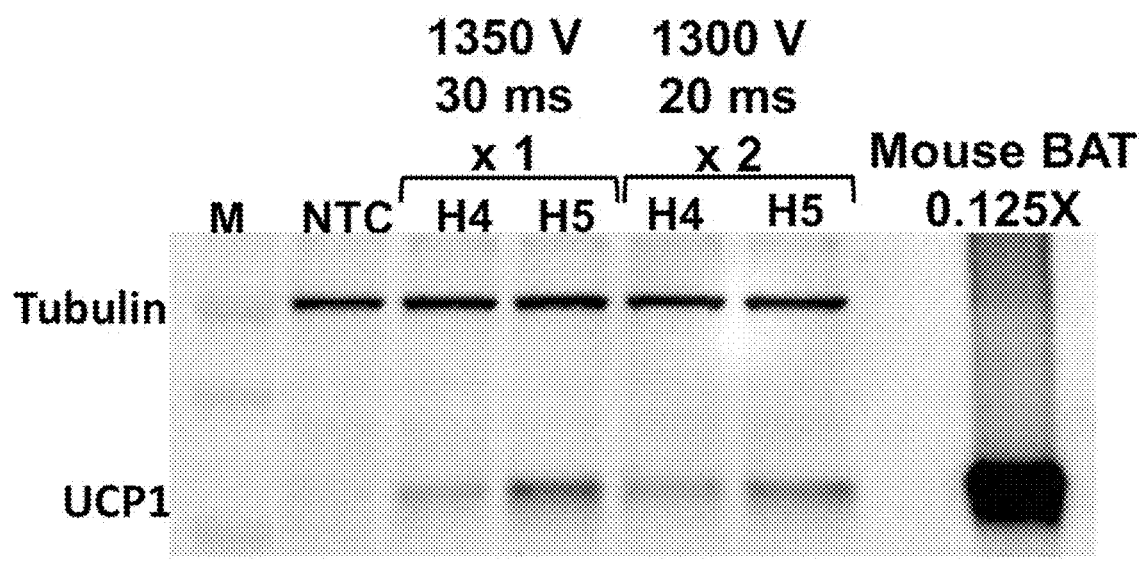
Figure 5I:
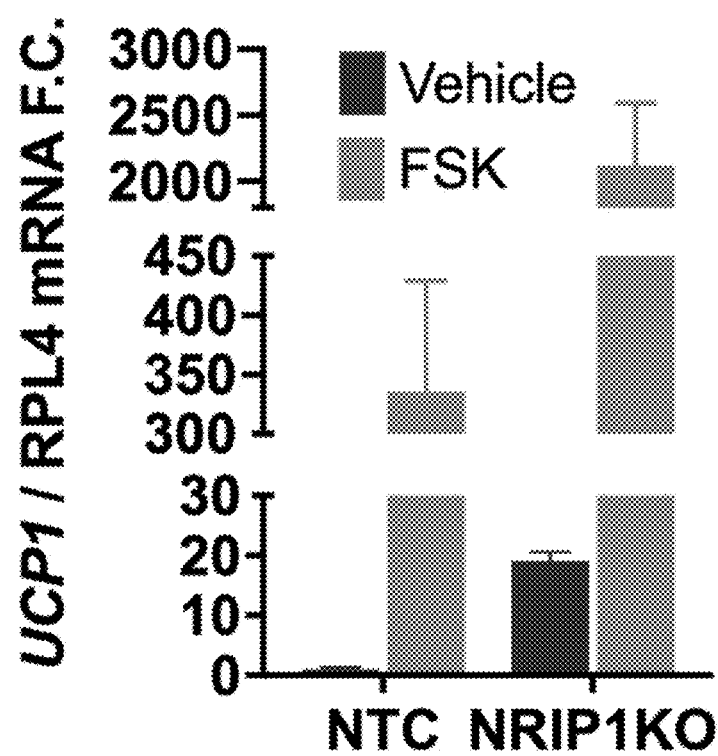

FIGS. 5a-5i: High efficiency NRIP1 disruption in human adipocytes by SpyCas9 reveals variable UCP1 upregulation in a screen of sgRNAs targeting different loci of NRIP1. FIG. 5a: Mapping of sgRNAs H1-H6 screened against human NRIP1 coding region entirely located in exon 4. FIG. 5b: Editing efficiency as evaluated with indel percentage 72 hours after the transfection of primary preadipocytes (black) and differentiation to mature primary adipocytes (gray). FIG. 5c: Indel distribution of NRIP1 sgRNA-H5 with frameshift indels that are sustained after differentiation. FIG. 5d: Microscopic image of cell culture of non-targeted control (top) and NRIP1 disrupted (bottom) mature adipocyte morphology in cell culture at 10× magnification and scale bar represents 400 μm. FIG. 5e: NRIP1 gene expression by RT-PCR in mature adipocytes on day 7 post differentiation targeted with the different sgRNAs. FIG. 5f: Immunoprecipitation assay for NRIP1 (140 kDa, arrows at right) in mature human adipocytes on day 7 post differentiation targeted with the different sgRNAs. The total protein lysate amount used in the assay was 250 μg per sample. M denotes molecular weight marker. FIG. 5g: UCP1 expression by RT-PCR in mature adipocytes on day 7 post differentiation targeted with the different sgRNAs compared to non-targeted control cells. FIG. 5h: Western blot for UCP1 protein (33 kDa) in mature adipocytes on day 7 post differentiation targeted by the sgRNAs-H4 and -H5 with two different electroporation optimization protocols. Lanes 2-6 were loaded with 20 μg of total protein while lane 9 was loaded with 2.5 μg of total protein isolated from mouse BAT. FIG. 5f: UCP1 gene expression by RT-PCR in non-targeted control or NRIP1 depleted adipocytes on day 7 post differentiation after a 7-hour stimulation of forskolin 10 μM or vehicle. NTC=Non-targeting control. Bars denote mean. Error bars denote Mean±S.E.M, n≥3 biological replicates. In FIG. 5f and FIG. 5h M denotes molecular weight marker.

Figure 6A:
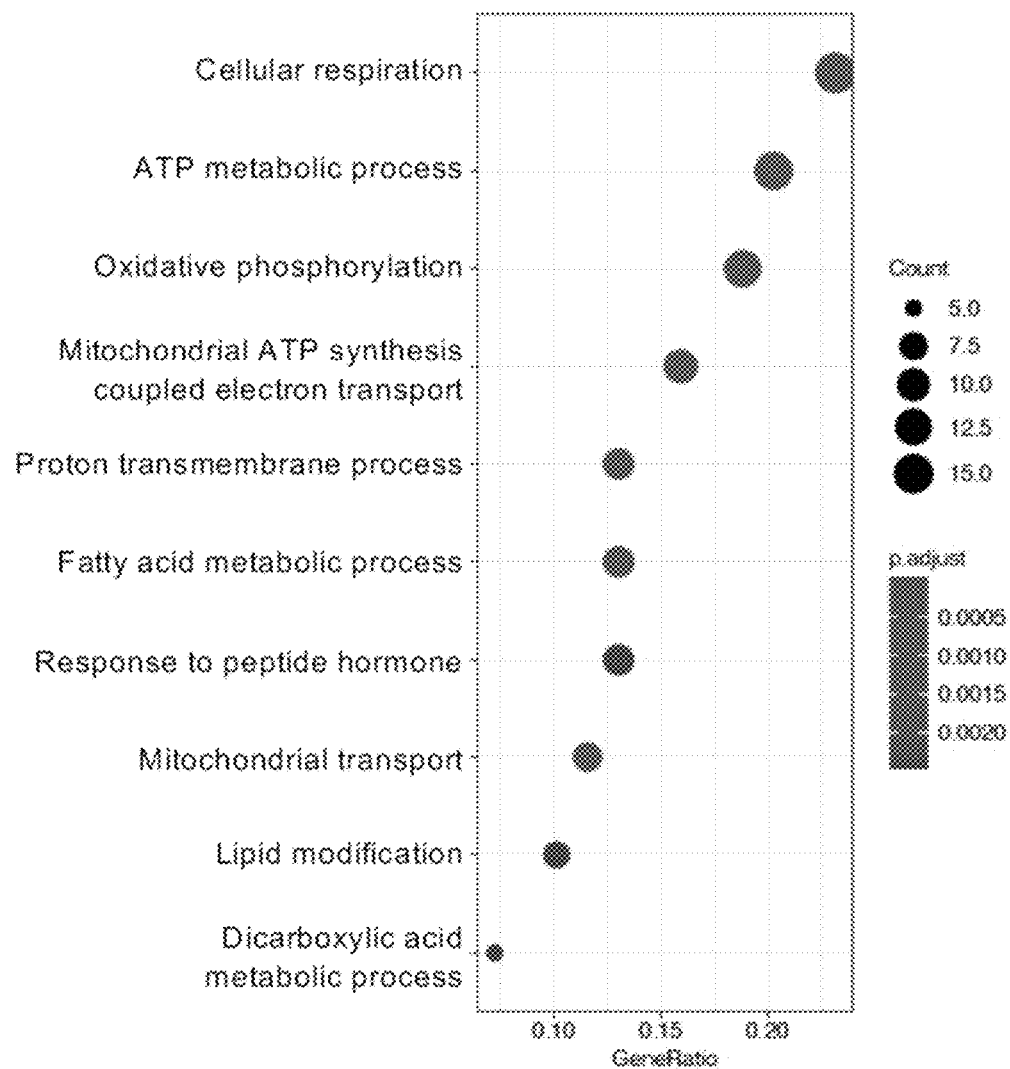
Figure 6B:
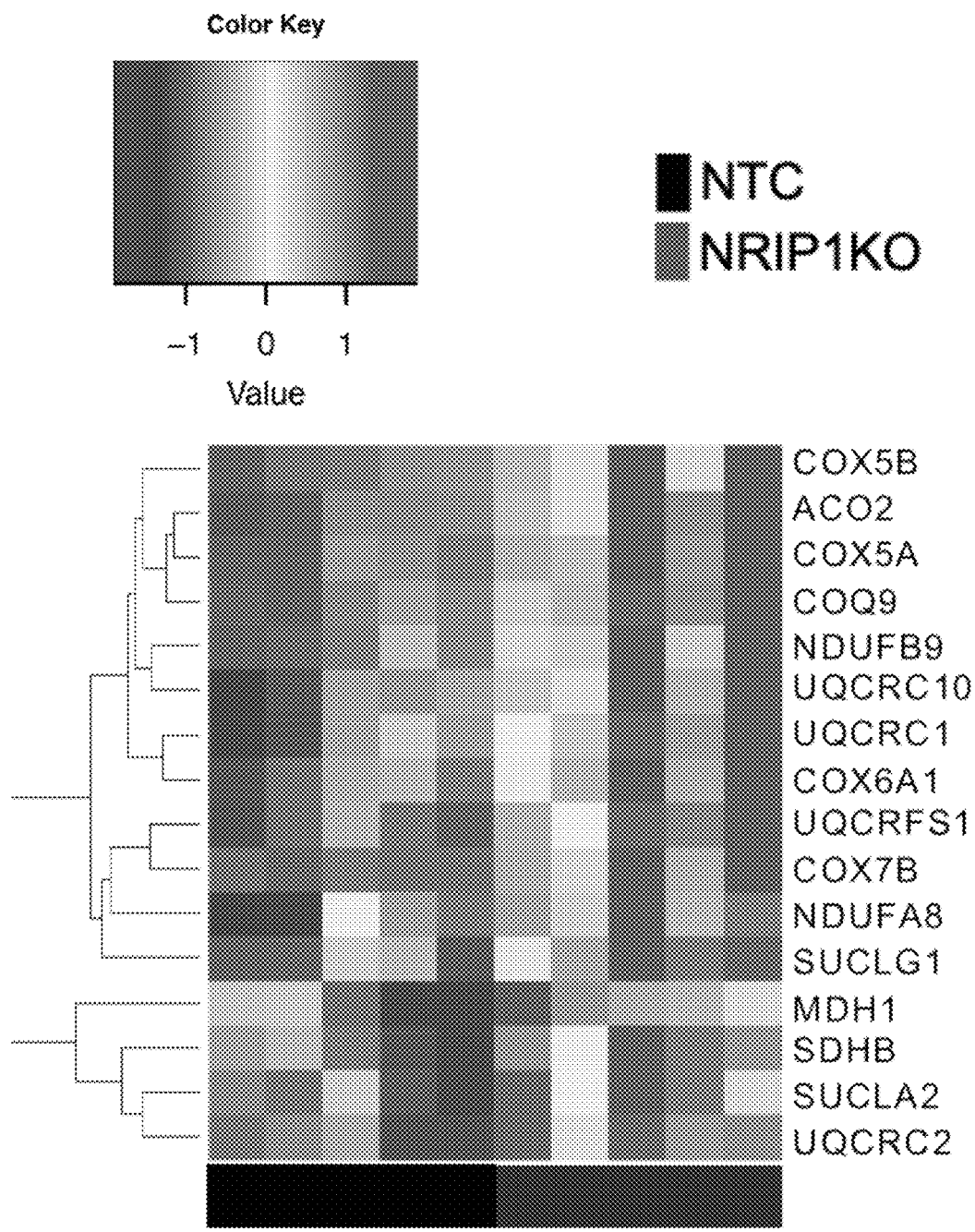
Figure 6C:
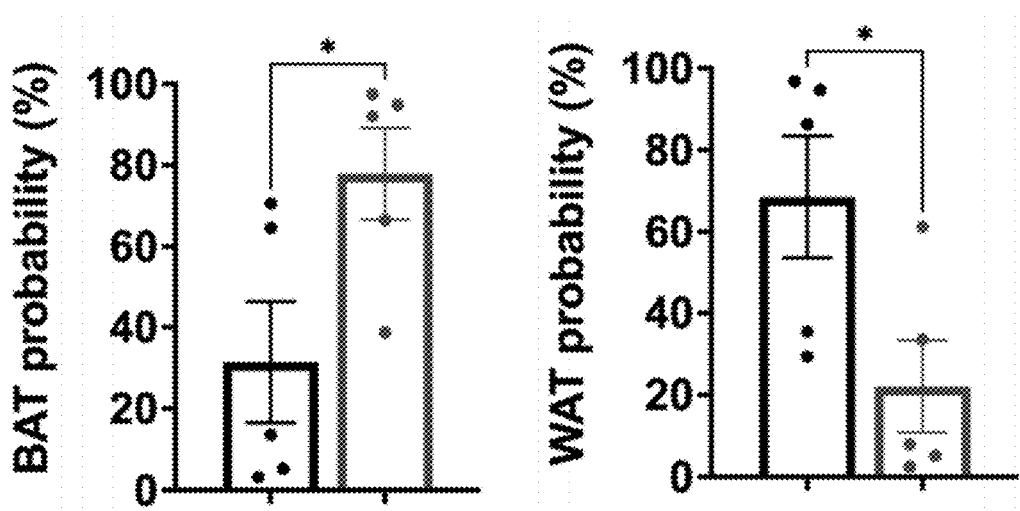
Figure 6D:
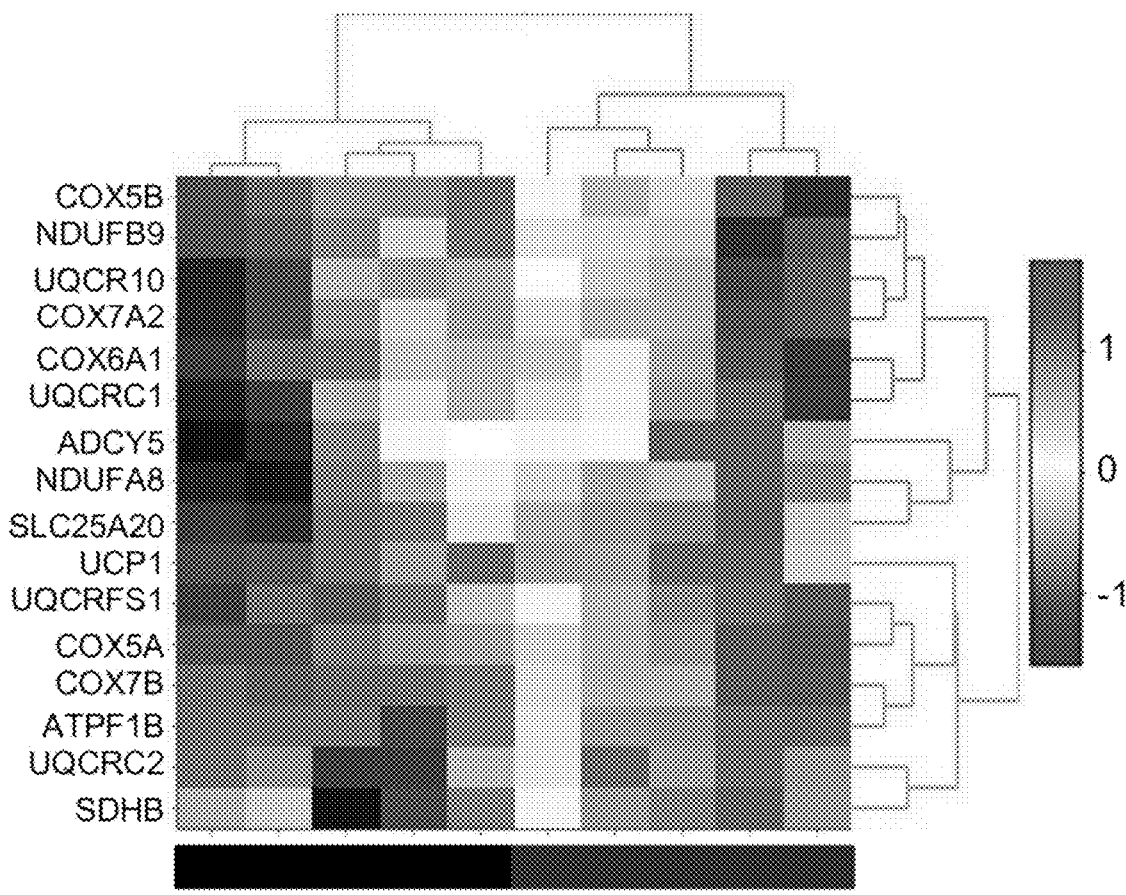

FIGS. 6a-6d: RNA sequencing on human NTC and NRIP1KO mature adipocytes on day 7 after differentiation. FIG. 6a: Top 10 pathways associated with all upregulated genes detected. FIG. 6b: Heatmap of genes associated with cellular respiration that were upregulated in NRIP1KO adipocytes. FIG. 6c: Browning probability calculated using the ProFAT online tool. *P value=0.037 by unpaired T-test. FIG. 6d: Heatmap of genes related to thermogenesis that were found highly expressed in the NRIP1KO samples compared to the NTC. Cut-offs were set at padj<0.1 and fold change>1.3. NTC (n=5), NRIP1KO (n=5). NRIP1KO adipocytes were transfected with SpyCas9 and NRIP1 sgRNA-H5.

Figure 7A:
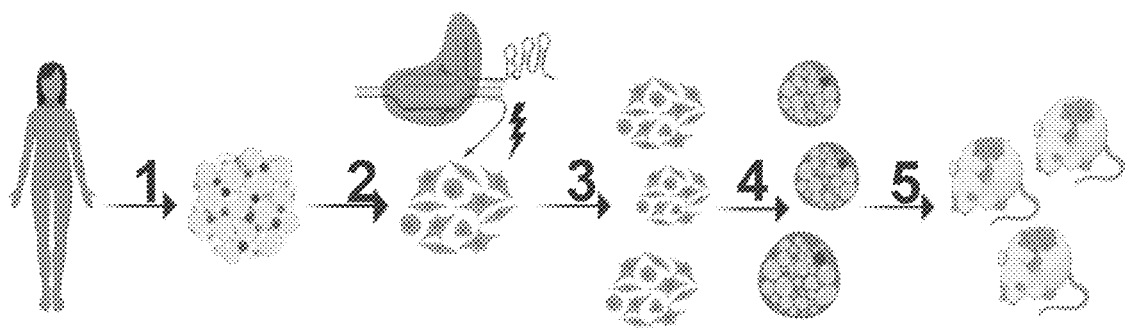
Figure 7B:
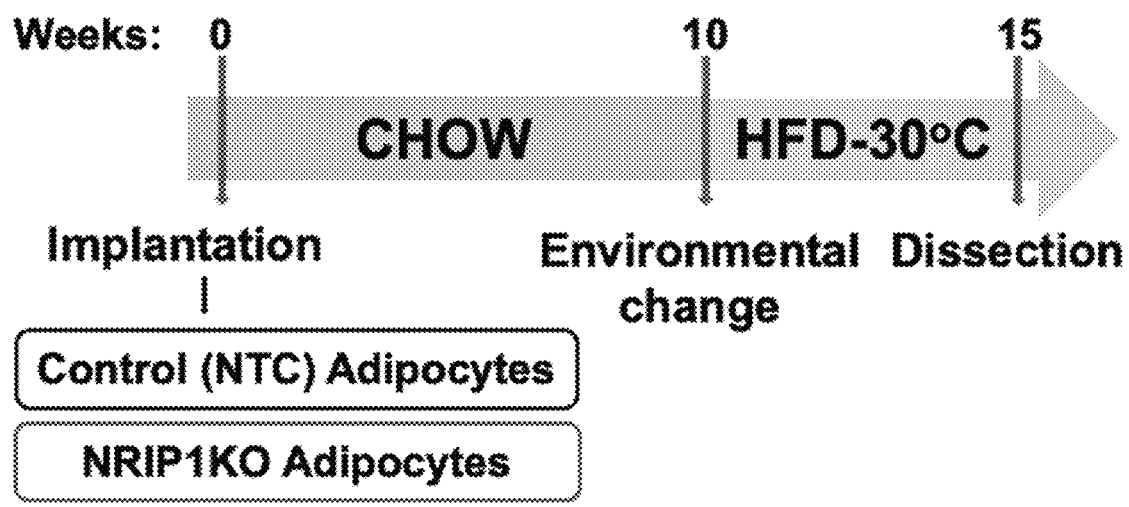
Figure 7C:
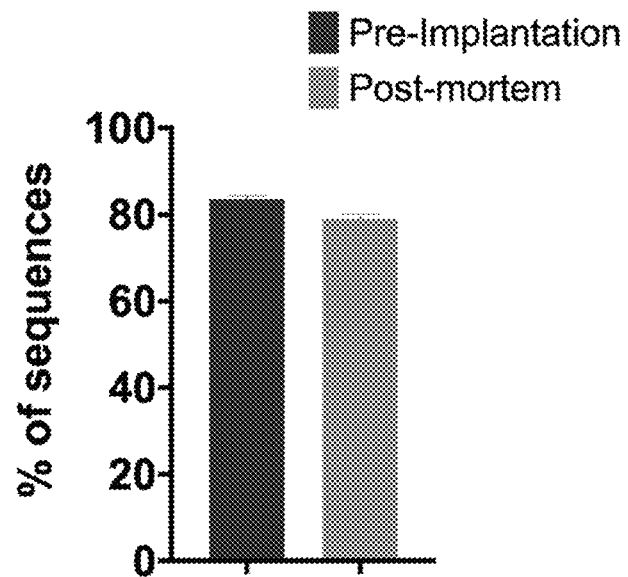
Figure 7D:
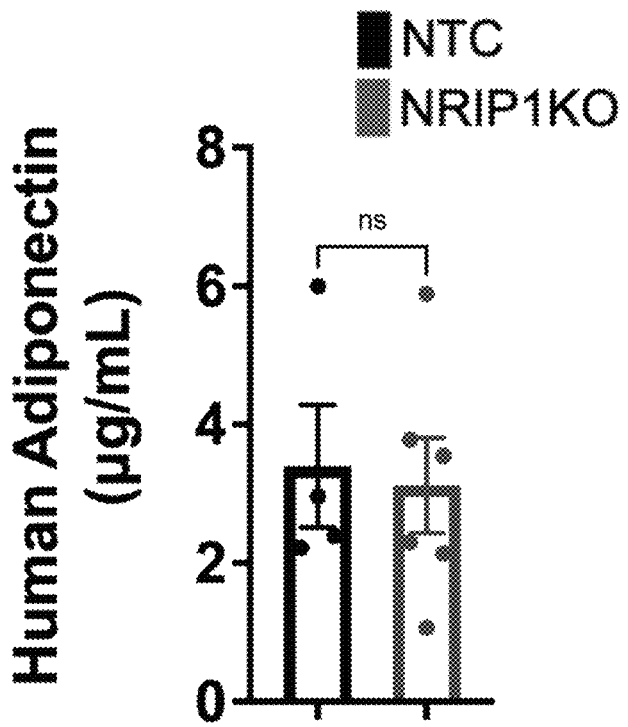
Figure 7E:
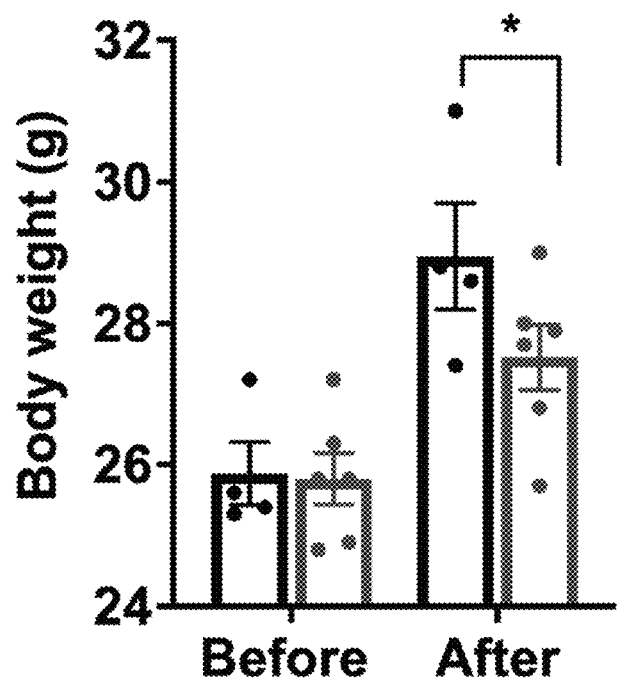
Figure 7F:
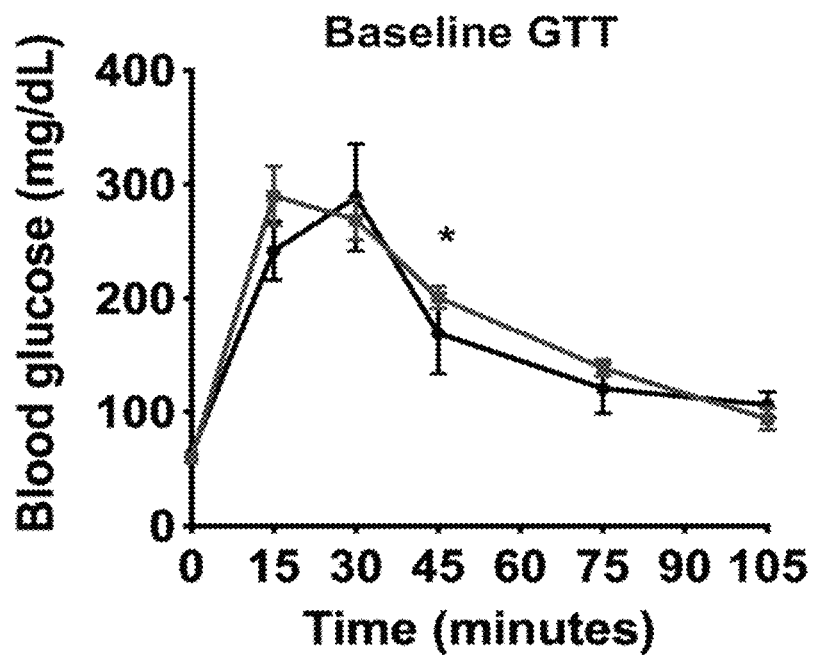
Figure 7G:
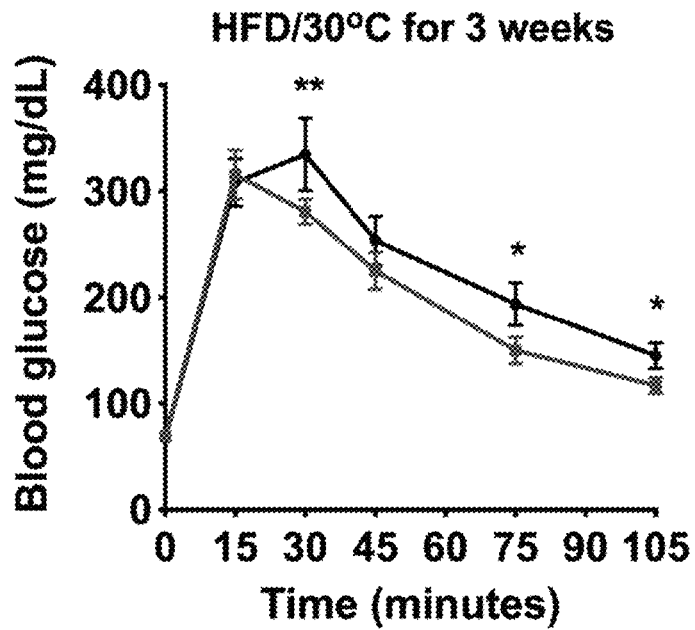
Figure 7H:
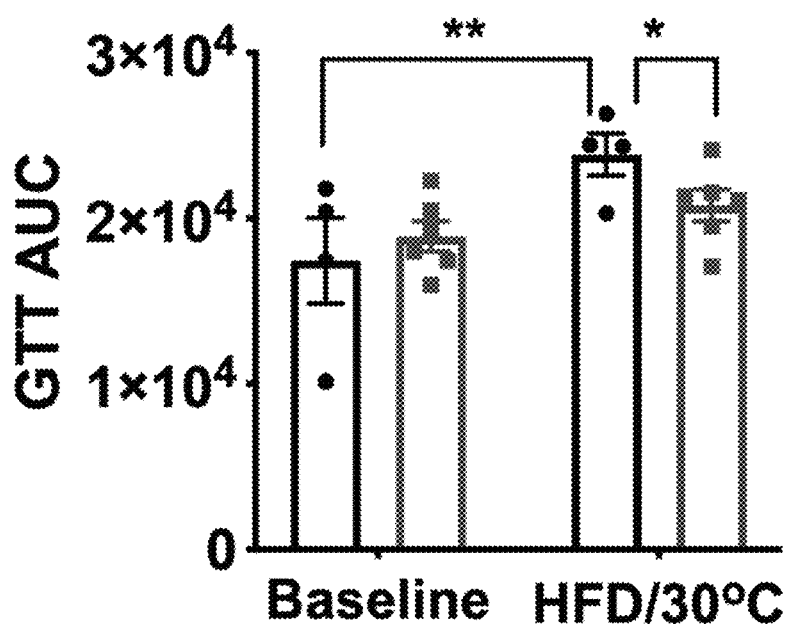
Figure 7I:
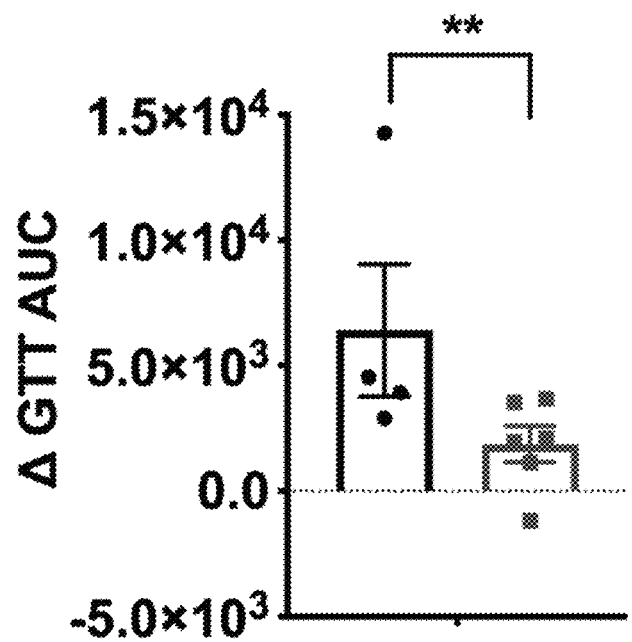
Figure 7J:
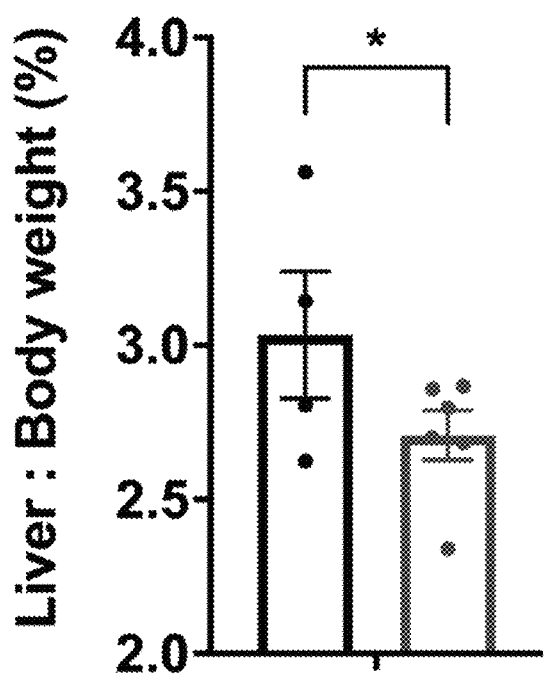
Figure 7K:
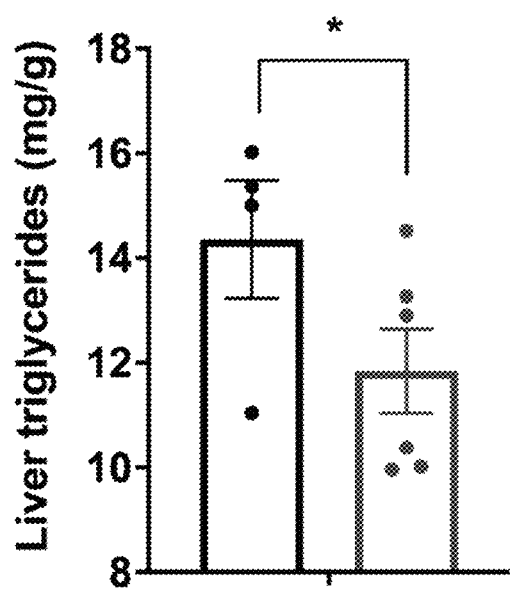

FIGS. 7a-7k: Implantation of NRIP1-targeted human adipocytes decreases body weight as well as liver triglyceride, and enhances glucose tolerance in recipient immunocompromised, HFD fed NSG mice. Mice were implanted with either human adipocytes previously treated with NTC sgRNA/Cas9 RNPs or with sgRNA-H5/Cas9 RNPs (NRIP1KO). FIG. 7a: Study description: 1) adipose tissue isolation from a human donor during panniculectomy, 2) harvesting of human primary preadipocytes after development Cas9/sgRNA RNPs were delivered into the human preadipocytes by electroporation followed by 3) expansion 1:6 of the genetically modified preadipocytes and 4) their differentiation into mature adipocytes; 5) Implantation of non-targeted control (NTC) sgRNA treated adipocytes versus the NRIP1 depleted adipocytes was performed in the dorsal area of NSG mice. FIG. 7b: Schematic protocol of implantation of human NTC adipocytes or NRIP1KO adipocytes into NSG mice followed by HFD feeding. FIG. 7c: Editing efficiency as evaluated with percentage of indels in the mature adipocytes transfected with NRIP1KO sgRNA-H5 before implantation (black) and indel percentage in the genomic DNA isolated from the NRIP1 depleted implants 15 weeks following transplantation. FIG. 7d: Human adiponectin levels detected in the plasma of NSG recipients 9 weeks following transplantation for the assessment of engraftment and functionality of the implants. P value=0.812 (ns). FIG. 7e: Total body weight of NSG mouse recipients before transplantation (left) and after 3 weeks on HFD and thermoneutrality (right). FIG. 7f: Baseline glucose tolerance test after 16 hr. fasting before transplantation. *p value=0.029. FIG. 7g: Glucose tolerance test after 3 weeks on HFD and thermoneutrality. P values **30 min=0.006; *75 min=0.023; *105 min=0.017. FIG. 7h: Glucose tolerance areas under the curve (GTT AUC) before transplantations (left) and 3 weeks after HFD under thermoneutrality (right). **p value=0.002; *p value=0.033. FIG. 7i: Matched difference of the GTT AUC before transplantations (left) and 3 weeks after HFD and thermoneutrality (right). P value=0.001. FIG. 7j: Liver over whole body weight percentage. P value=0.012. FIG. 7k: Triglyceride measurements in pulverized liver extracts after dissection. P value=0.036. Black=NTC cell implant recipients (n=4); gray=NRIP1KO cell implant recipients (n=6). Bars denote mean, error bars denote mean±SEM. * p<0.05, ** p<0.01 by unpaired T-test. NRIP1KO adipocytes were transfected with SpyCas9 and NRIP1 sgRNA-H5.

Figure 8A:
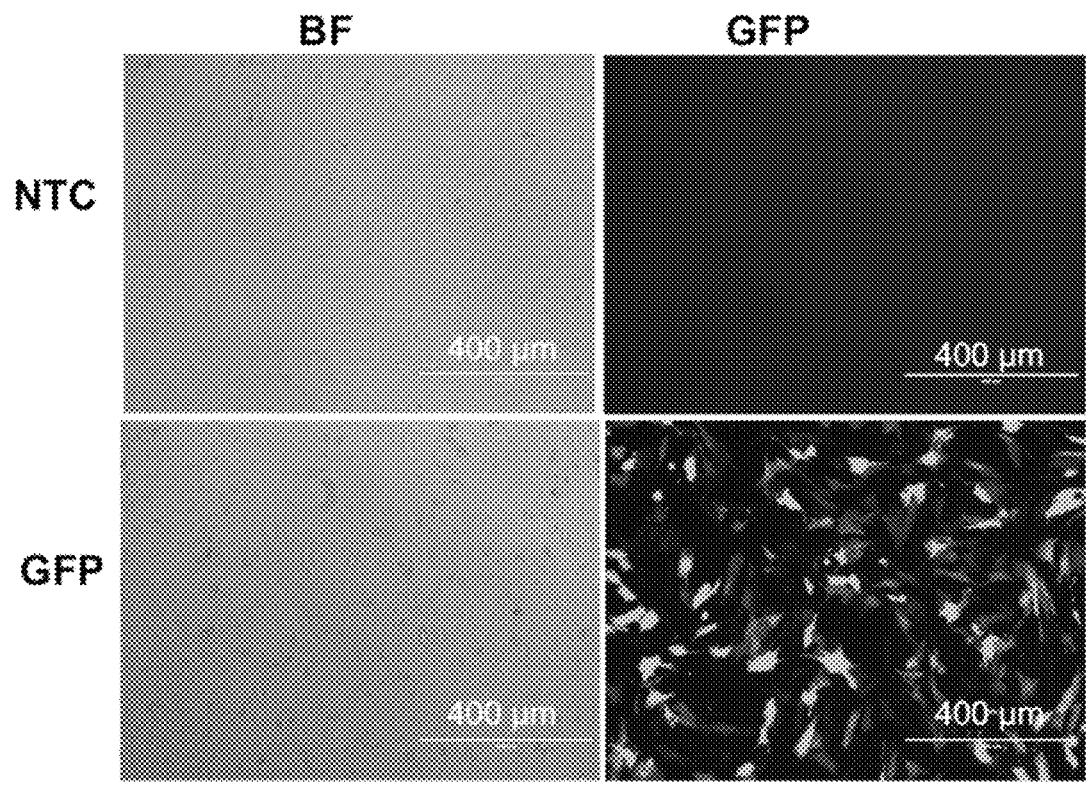
Figure 8B:
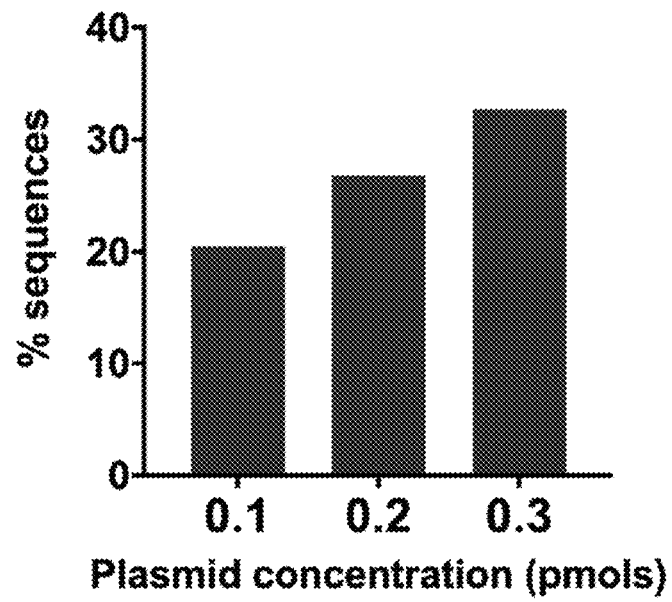
Figure 8C:
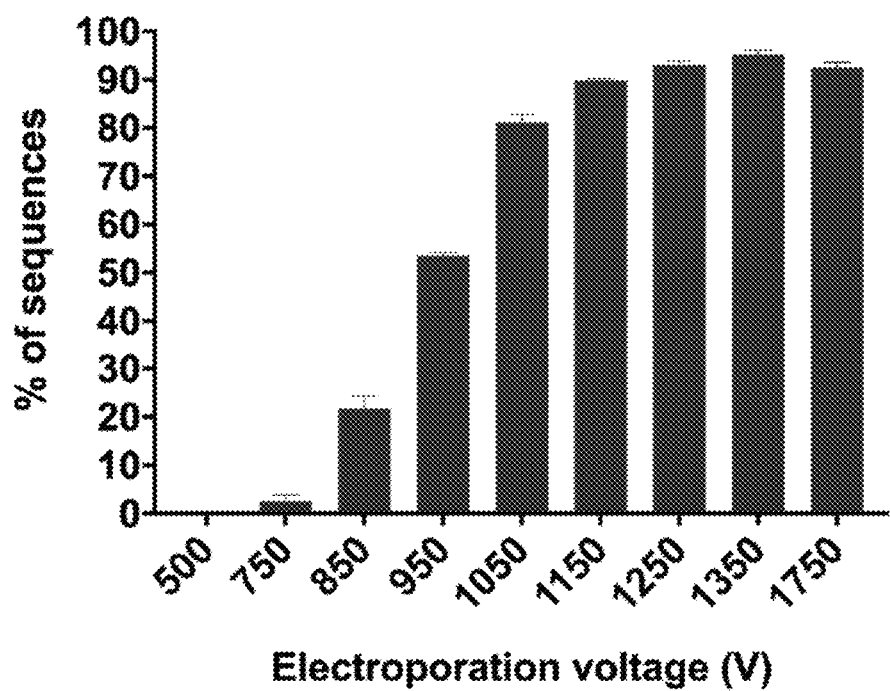
Figure 8D:
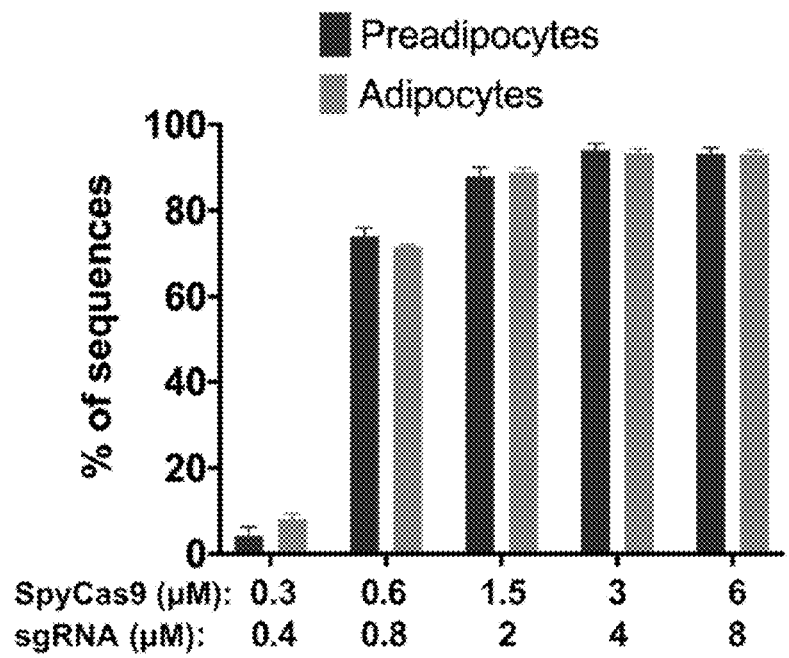
Figure 8E:
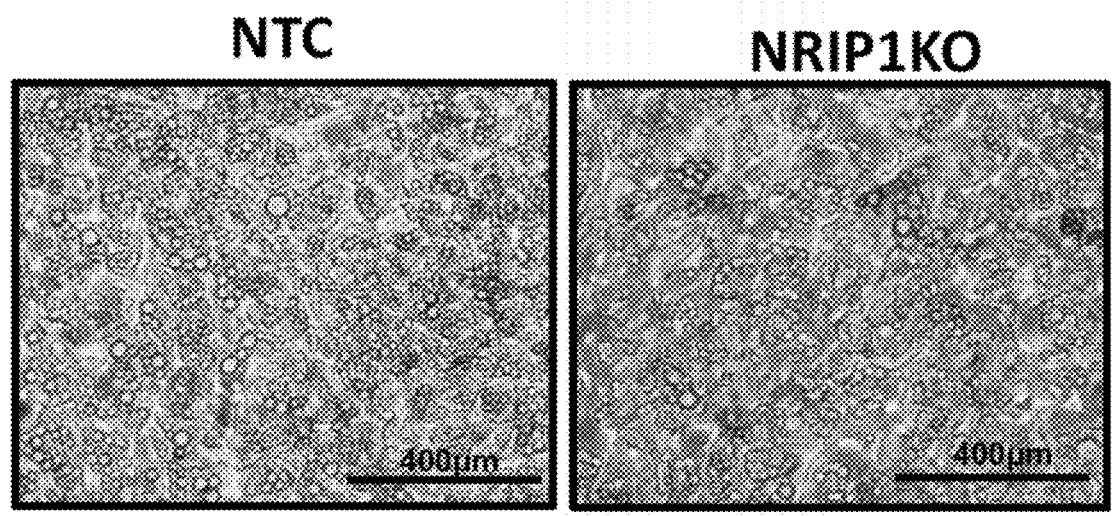
Figure 8F:
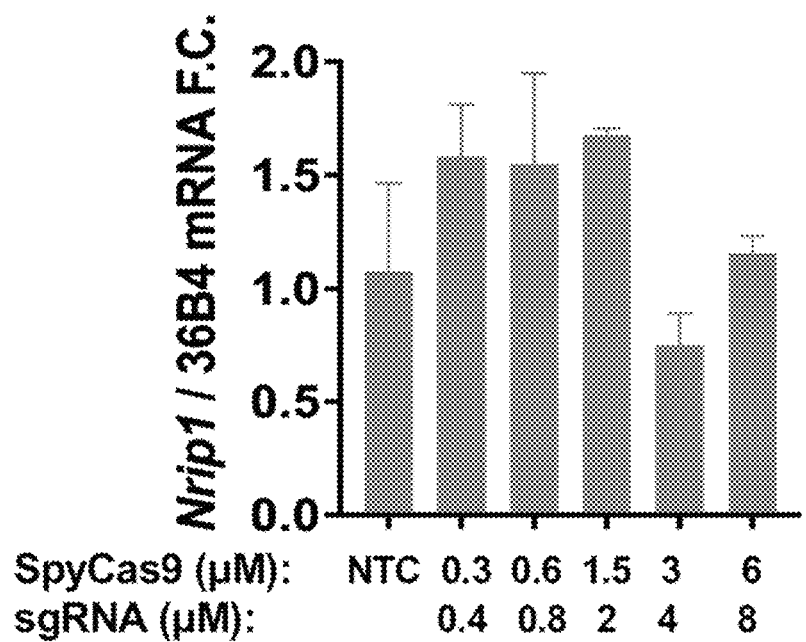
Figure 8G:
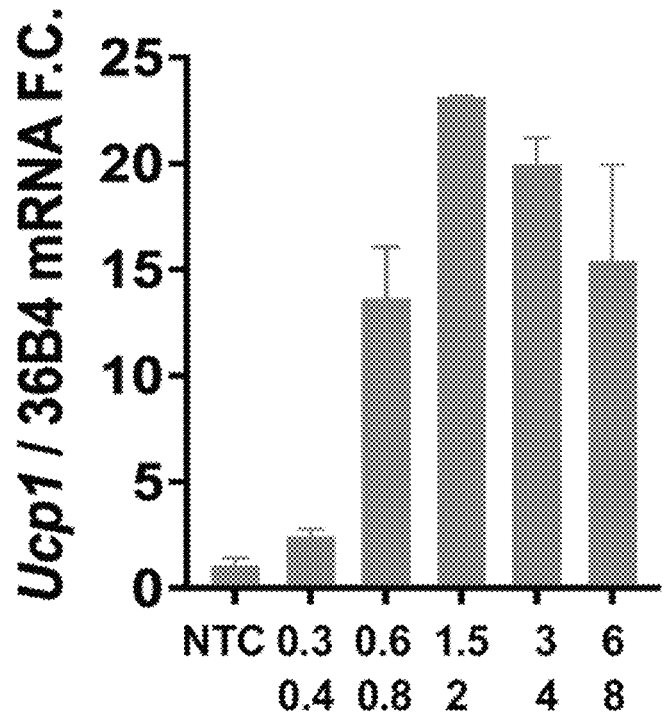

FIGS. 8a-8g: SpyCas9/sgRNA RNPs are more efficiently delivered into murine adipocytes by electroporation than plasmid expression. Delivery of SpyCas9/sgRNA RNPs versus plasmids encoding either GFP or Cas9 and sgRNA electroporated with preadipocytes were compared. FIG. 8a: GFP expression plasmid (Lonza pmaxGFP) was used in various concentrations for optimization of the plasmid delivery by electroporation in murine preadipocytes (data not shown) to determine the optimum range (0.1-0.2 pmols) that induces GFP expression by fluorescent microscopy (white line=400 µm). Top: Control preadipocytes Bottom: Preadipocytes transfected with 0.2 pmols at 72 hours after electroporation (1350 V, 30 ms, 1 pulse). FIG. 8b: Application of the optimized electroporation protocol to transfect preadipocytes with plasmids expressing SpyCas9 and sgRNA-M6 in three different concentrations within the range determined with the GFP plasmid titration: 0.1-0.3 pmols. FIG. 8c: Optimization of the electroporation protocol to deliver CRISPR RNPs in preadipocytes with 1 pulse and 30 ms width and increasing voltage. FIG. 8d: Titration of RNP concentrations in correlation with the editing efficiency with sgRNA-M6. FIG. 8e: Mature adipocytes transfected before differentiation with either NTC RNPs or sgRNA-M6 in cell culture and magnification 10x. FIG. 8f: Nrip1 gene expression by RT-PCR in mature adipocytes transfected with varying RNP concentrations. FIG. 8g: Ucp1 gene expression by RT-PCR in mature adipocytes transfected with varying RNP concentrations. NTC=Non-targeting control. Bars denote mean. Error bars denote Mean±S.E.M. n>3 biological replicates. Nrip1 sgRNA-M4 was used in the titration experiment.

Figure 9A:
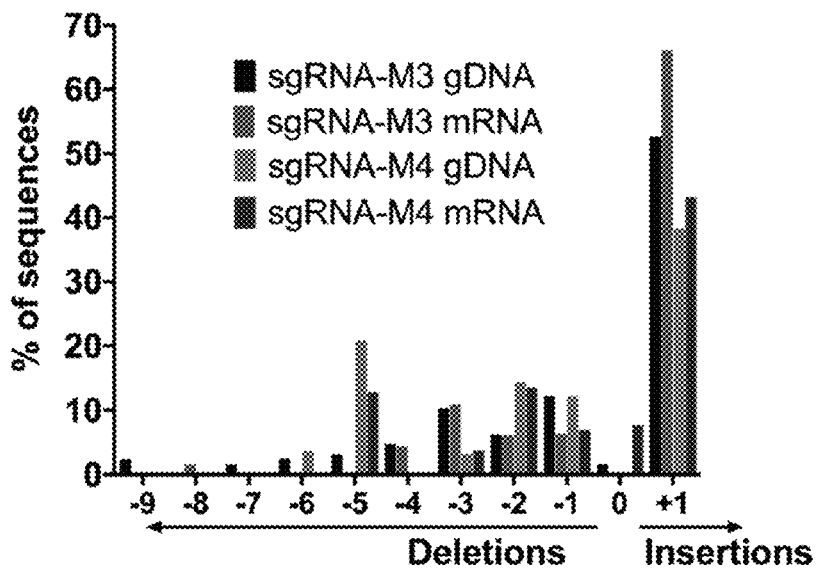
Figure 9B:
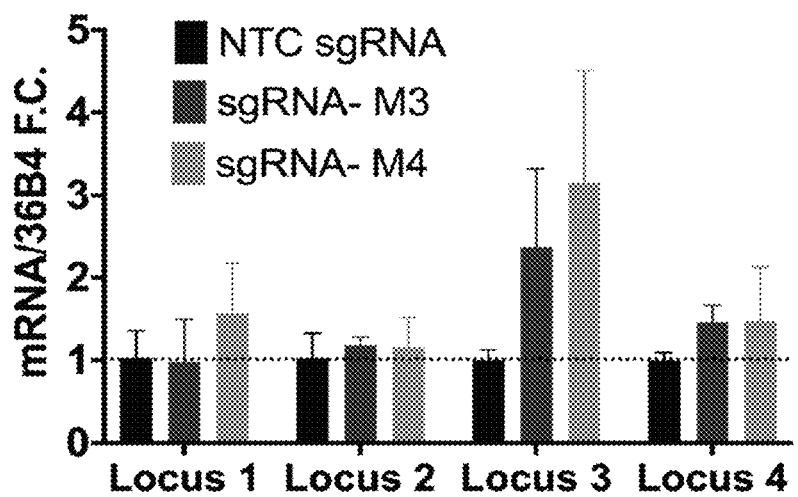
Figure 9B:
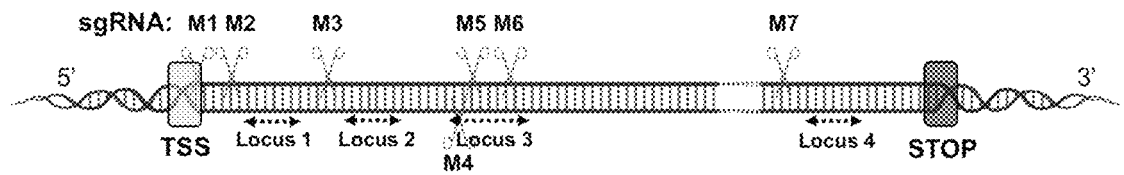
Figure 9C:
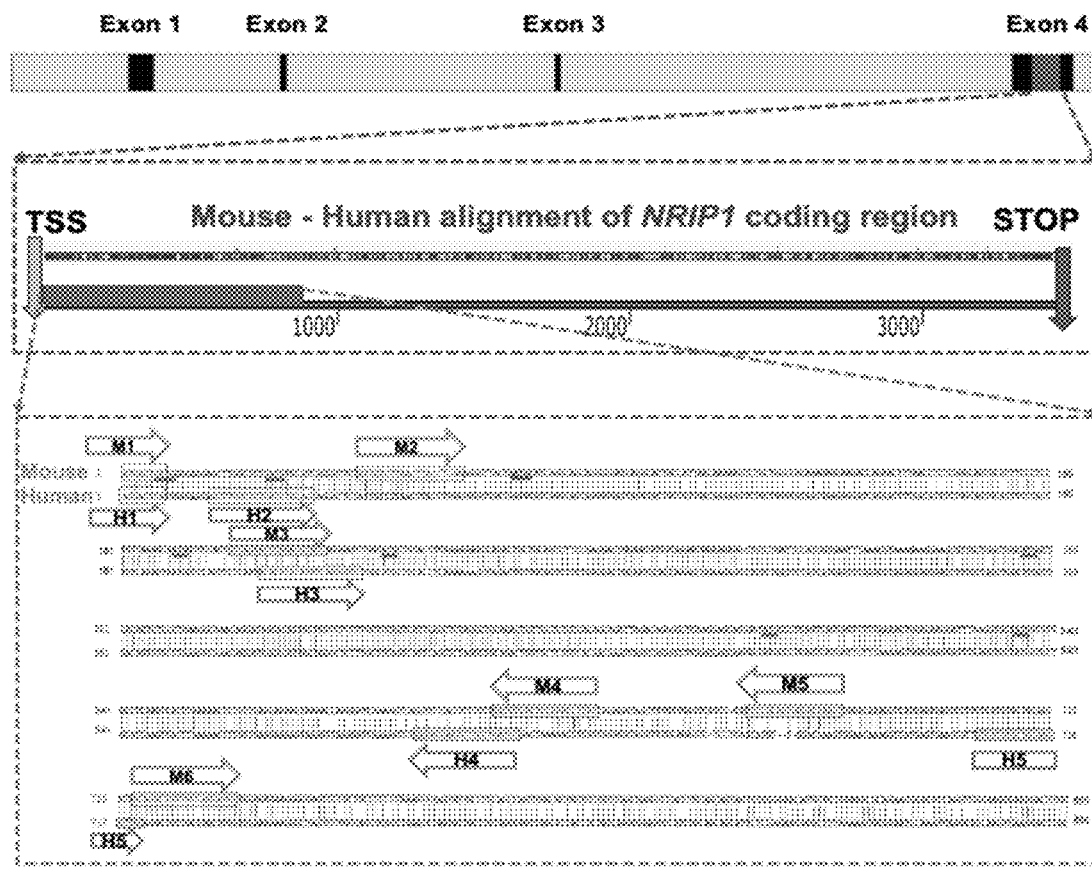

FIGS. 9a-9c: mRNA of Nrip1 harbors the indels created by the CRISPR-RNPs with little evidence of truncation or degradation of modified Nrip1 mRNAs. FIG. 9a: Comparison of the indel distribution of the genomic DNA and the cDNA after double rDNase treatment in the template RNA of cells transfected with sgRNA-M3 and sgRNA-M4. FIG. 9b: RT-PCR results of the expression of different loci across Nrip1 cDNA as shown in the map. FIG. 9c: Top: Nrip1 gene includes 4 exons (black) and the coding region (gray) is contained in exon 4. Middle: Alignment of the mouse and human coding regions of NRIP 1 that spans 3486 bp and 3477 bp respectively between the TSS and STOP codons, highlighting the site targeted with sgRNAs MI-6 and HI-5 (gray). Bottom: 5'→3' DNA sequence alignment of the mouse (top strand; nucleotides 348-1246 of SEQ ID NO: 20) and human (bottom strand; nucleotides 334-1229 of SEQ ID NO: 21) of the N-terminus area targeted with the sgRNAs M1-6 for the mouse (arrows) and H1-5 for the human (arrows). Underlined (gray) are the ATG sequences in frame or out of frame between the TSS and the first sgRNA that depletes NRIP1 which could potentially serve as alternative translation initiation sites. In FIG. 9b error bars denote mean±S.E.M. n>3 biological replicates.

Figure 10A:
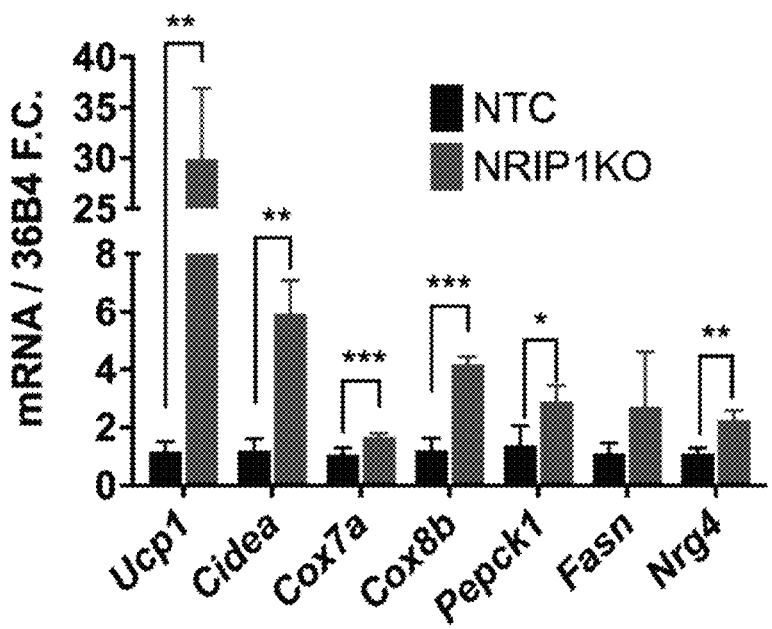
Figure 10B:
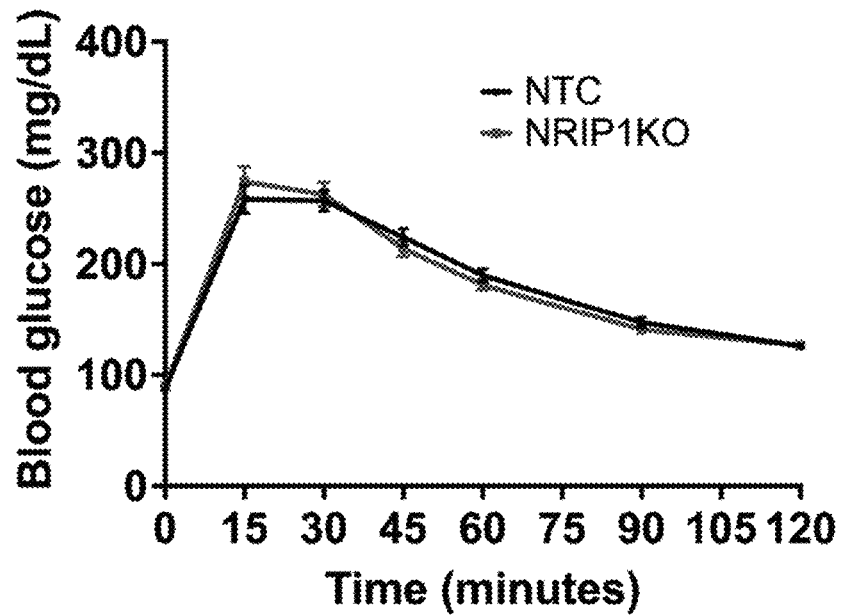
Figure 10C:
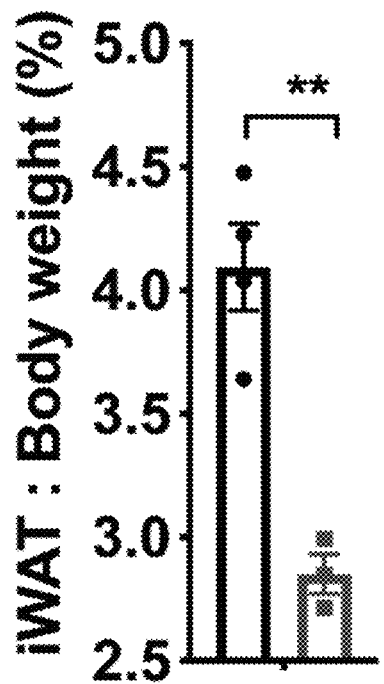
Figure 10D:
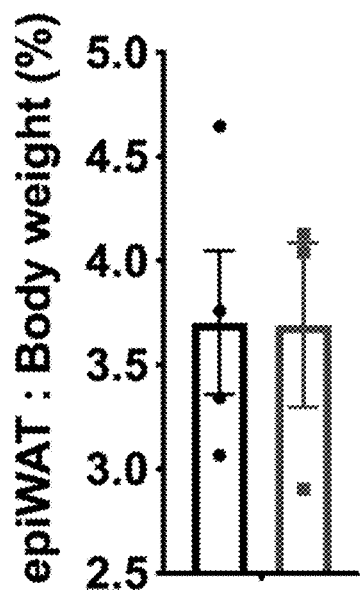
Figure 10E:
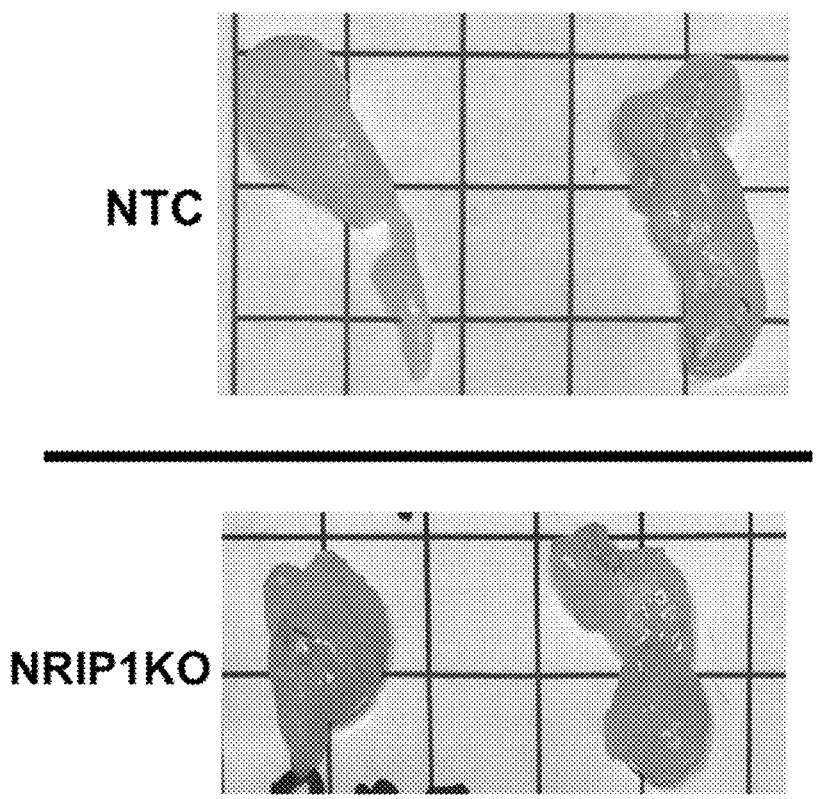
Figure 10F:
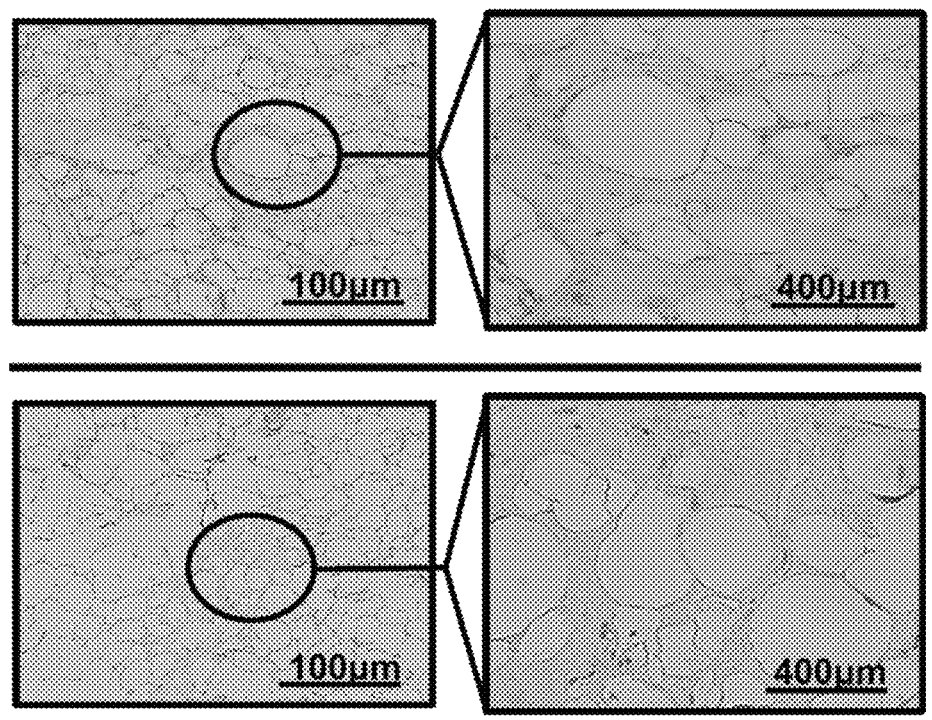
Figure 10G:
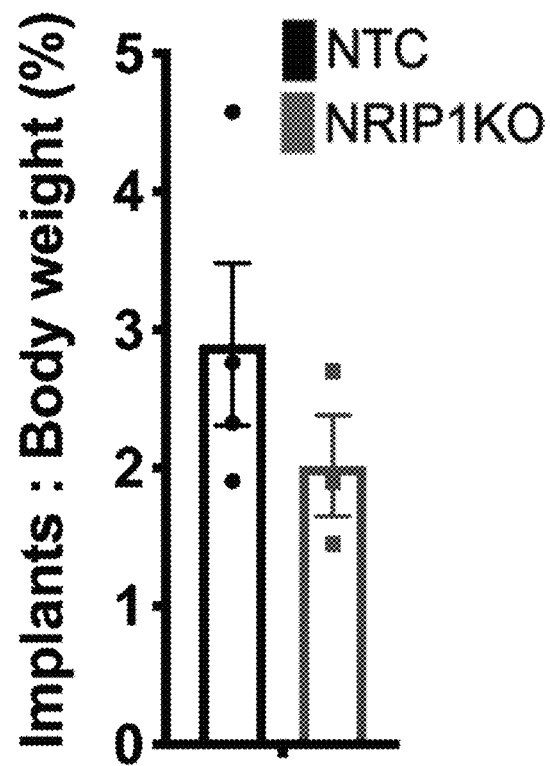
Figure 10H:
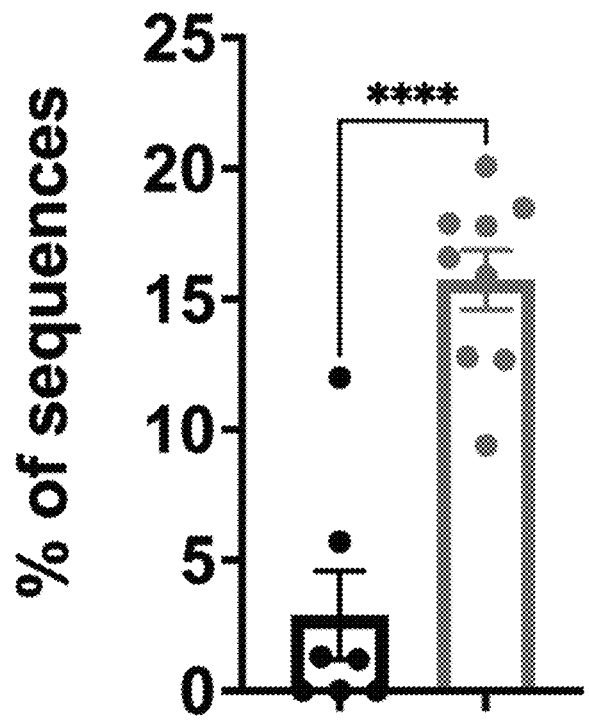
Figure 10I:
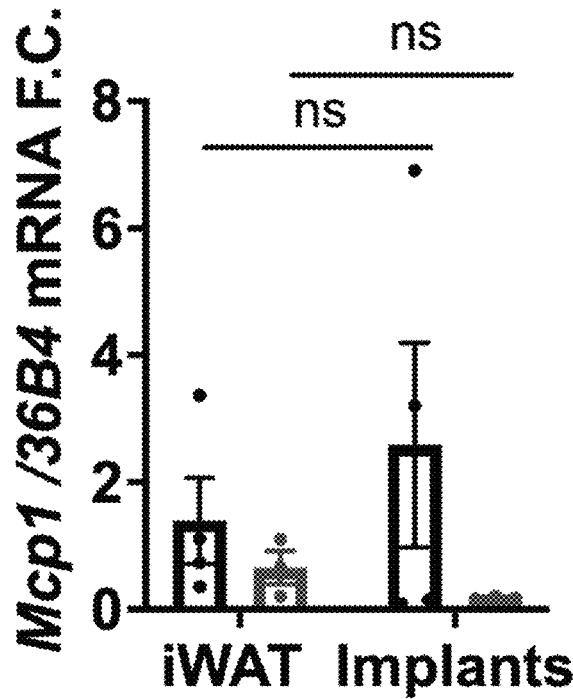
Figure 10J:
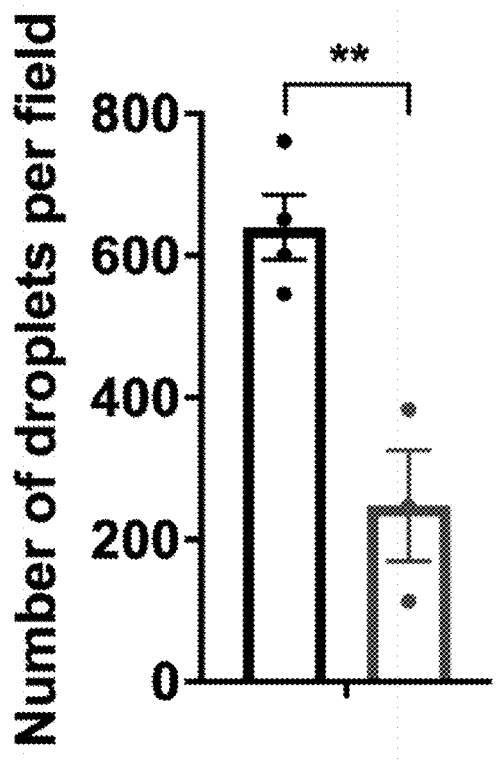
Figure 10K:
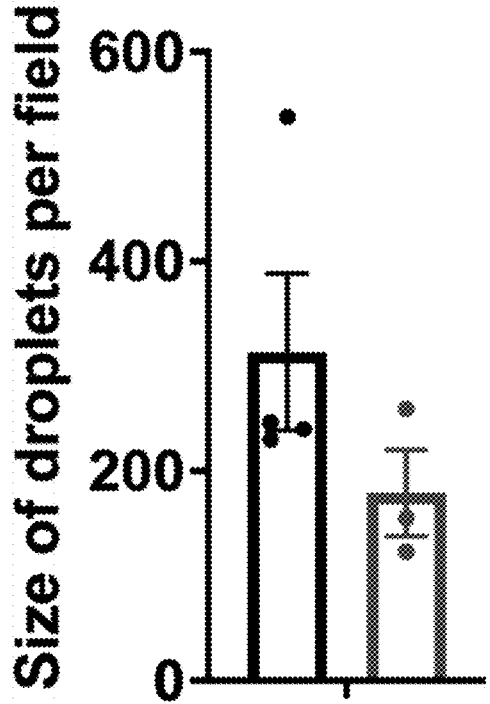
Figure 10I:
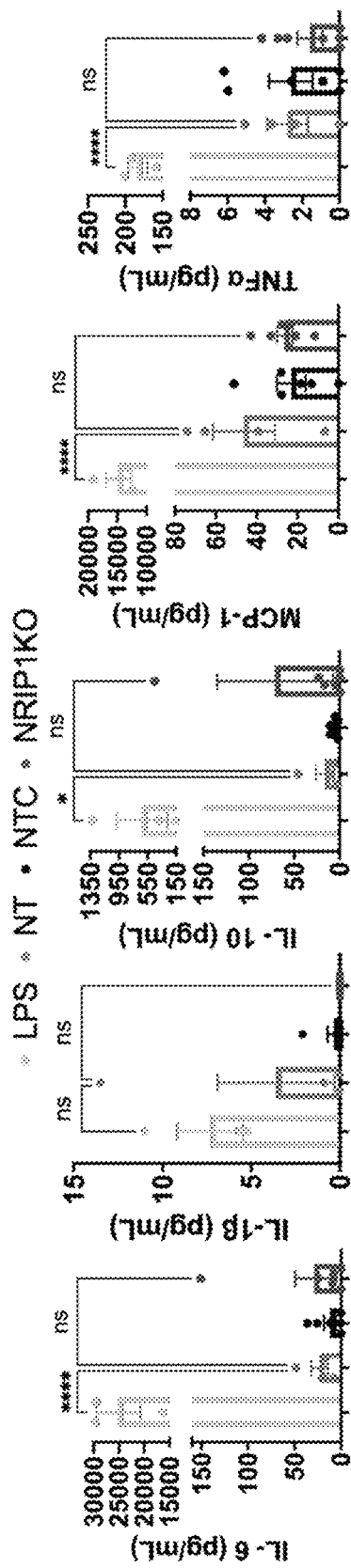

FIGS. 10a-10l: Characterization of mice implanted with Cas9/NTC sgRNA-versus Cas9/sgRNA-M6-treated adipocytes. FIG. 10a: RT-PCR results for expression of genes involved in thermogenesis, mitochondrial electron transport chain, lipid and glucose metabolism and the neurotrophic factor Nrg4 prior to implantation. P values: Ucp1=0.004; Cidea=0.003; *Cox7a=0.0005; *Cox8b=0.000005; *Pepckl=0.019; **Nrg4=0.006. FIG. 10b: Baseline GTT after 16-hour fasting in the chow-fed recipients before the implantation of adipocytes. FIG. 10c: iWAT over whole body weight percentage. P value=0.002. FIG. 10d: epiWAT over whole body weight percentage. P value=0.983. FIG. 10e: Macroscopic images of the whole implants of the recipients after dissection (square=1 cm²). f. Histology images stained with H&E of the implant in 5× magnification (left) and 20× magnification (right). FIG. 10g: Implants over whole body weight percentage. P value=0.0743. FIG. 10h: Editing evaluation of homogenized implant sample for each of the NRIP1KO adipocyte recipients by Sanger sequencing. Pvalue=0.00001. FIG. 10i: MCP-1 mRNA expression by RT-PCR in implants after dissection. FIGS. 10j-10k: Quantification of the number (FIG. 10j) (P value=0.006) and size (FIG. 10k) of lipid droplets (P value=0.216) in the histology of the livers of the mouse NRIP1KO adipocytes recipients. FIG. 10l: Measurement of cytokines/chemokines in the plasma of NTC and NRIP1KO implant recipients, non-treated controls on HFD and LPS injected mice (1 µg per mouse) for 2 hours. P values IL-1β=0.014; IL-6<0.0001; IL-10=0.0095; MCP1<0.0001 by one-way ANOVA. Black=NTC cell implant recipients; gray=NRIP1KO cell implant recipients, in FIGS. 10a-10b: NTC (n=13) ; NRIP1KO (n=14), FIG. 10g, FIG. 10j, FIG. 10k NTC (n=4) ; NRIP1KO (n=3) ; LPS (n=3) ; NT (n=4); NTC (n=6), NRIP1KO (n=7). Bars denote mean, error bars denote mean±SEM. *p<0.05, **p<0.01 by unpaired two-tailed T-test unless otherwise specified.

Figures 11A, 11B:
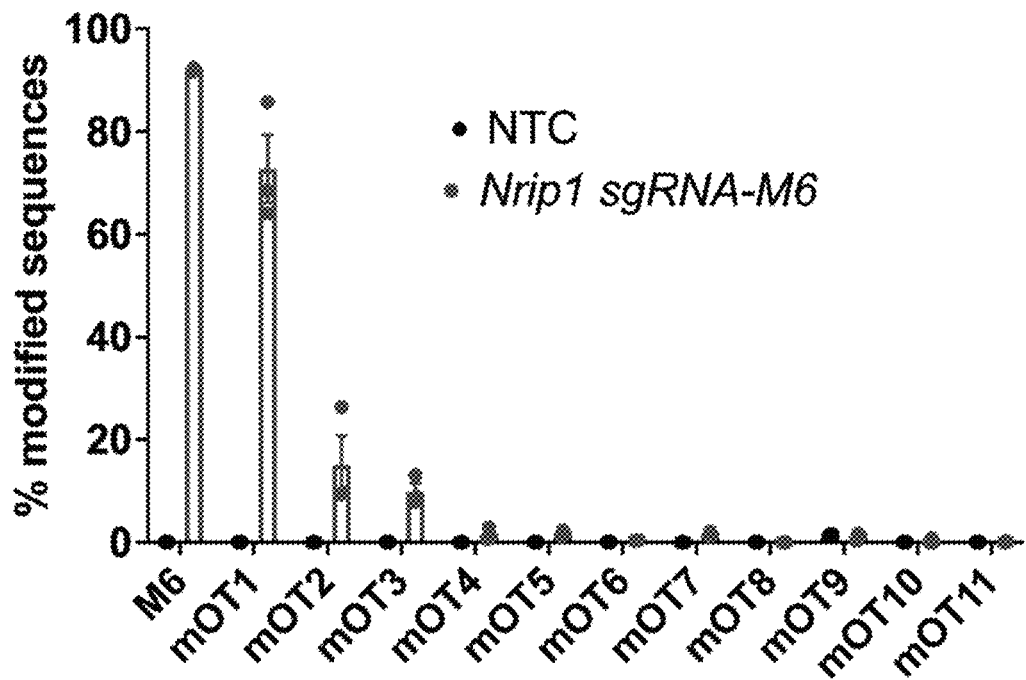
Figure 11F:
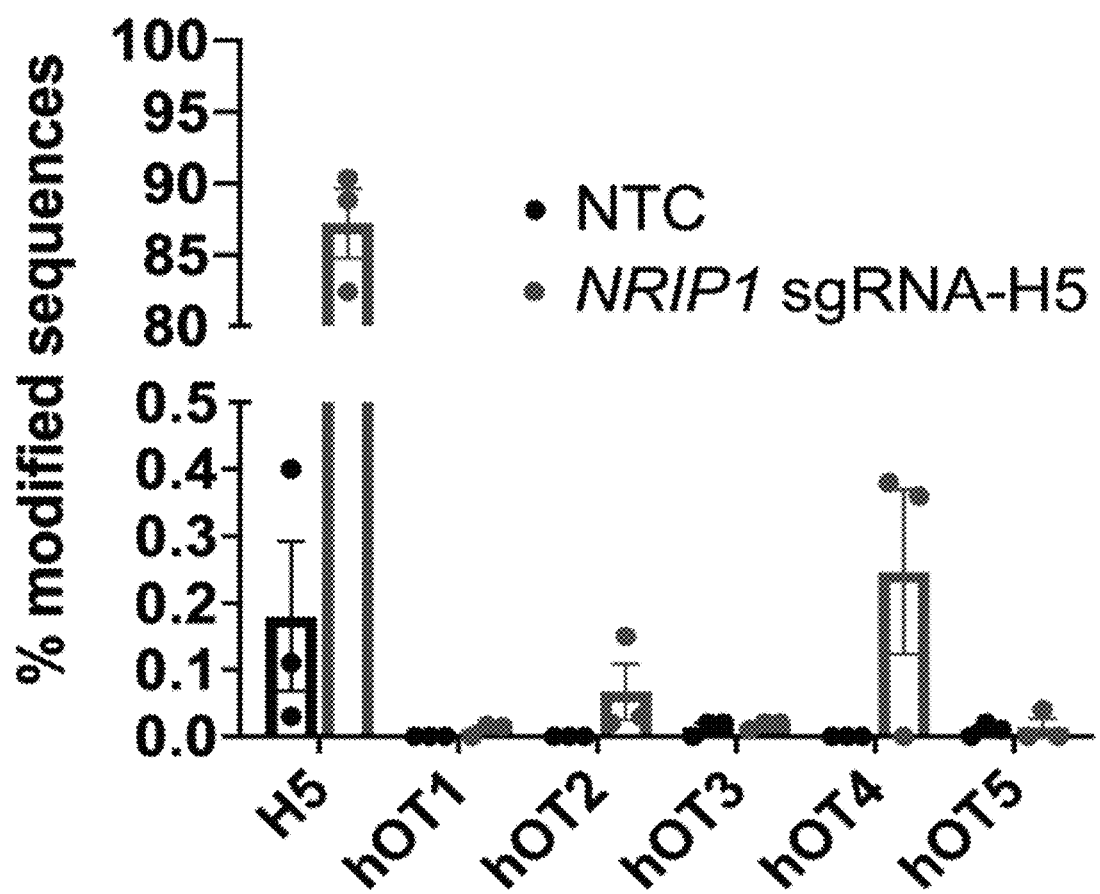

FIGS. 11a-11f: Off-target screen by GUIDE-seq and amplicon NGS sequencing in mouse and human adipocytes. FIG. 11a: Mouse predicted off-target sites detected by GUIDE-seq in NRIP1K0 mouse preadipocyte library (sgRNA-M6+SpyCas9+7.5 pmol of dsODN) with up to 6 sgRNA-M6 mismatches and up to 1 PAM mismatch ranked by number of reads. Gray triangle points the on-target site, and black triangles show the 11 top off-target sites ranked by number of mismatches and selected for Amplicon NGS screening. The sgRNA-M6 PAM sequence is provided as SEQ ID NO: 24. mOT1-mOT11 sequences are provided as SEQ ID NOs: 25-35, respectively. The remaining sequence is provided as SEQ ID NO: 36. FIG. 11b: Indel quantification by amplicon next generation sequencing on mouse mature adipocytes on-target (M6) and selected off-target loci (mOT1-11). FIG. 11c: Human predicted sites with DSB detected by GUIDE-seq in NRIP1KO human progenitor library (sgRNA-H5+SpyCas9+7.5 pmol of dsODN) with up to 6 sgRNA-H5 mismatches and up to 1 PAM mismatch ranked by number of reads. Gray triangle points the on-target site. The sgRNA-H5 PAM sequence is provided as SEQ ID NO: 37. FIG. 11d: Human predicted sites with DSB detected by GUIDE-seq in NRIP1KO human progenitor library (sgRNA-H5+SpyCas9+10 pmol of dsODN) with up to 6 sgRNA-H5 mismatches and allowed NGG, NAG, NGA PAM sequences. Gray triangle points the on-target site. The sgRNA-H5 PAM sequence is provided as SEQ ID NO: 37. FIG. 11e: Selected candidate off-target sites of sgRNA-H5 on human genome by Cas-offinder software. The sgRNA-H5 PAM sequence is provided as SEQ ID NO: 37. hOT1-5 sequences are provided as SEQ ID NOs: 38-42, respectively. FIG. 11f: Indel quantification by amplicon next generation sequencing on human mature adipocytes on-target (H5) and selected off-target loci (hOT1-5). In amplicon NGS, NTC (n=3), NRIP1KO (n=3). Error bars denote mean±S.E.M.

DETAILED DESCRIPTION

The present disclosure is based, at least in part, on the finding that high efficiency disruption of Nrip1 in mouse and human progenitor cells ex vivo by ribonucleoproteins (RNPs) of Cas9 protein and sgRNA prior to their differentiation into adipocytes enhanced their beige characteristics and improved their therapeutic activities following implantation into obese mice.

The use of human cells as therapeutics offers major advantages over small molecule drugs and biologics in treating certain diseases based on their abilities to home to specific organs or cell types, initiate cell-cell interactions and secrete multiple bioactive factors[1,2]. Although still in early stages of development, cellular therapies have already had major impact on treatment of certain forms of cancer such as leukemia, lymphoma, melanoma and small cell lung carcinoma[3,4]. This approach involves genetic modification ex vivo of immune cells taken from a human subject to enhance their ability to disrupt malignancies upon infusion back into the same subject. In theory, this strategy should be effective in diseases in which cells with relevant therapeutic potential can be genetically modified to enhance that potential. For example, obesity and type 2 diabetes (T2D) involve multiple cell types that are disrupted in metabolic pathways in which their repair would alleviate disease[5-7]. Adipocytes represent such cells in which some of the defects have been identified[8-10]. Studies described herein take advantage of recent discoveries revealing the utility of thermogenic adipocytes to function as major beneficial regulators of whole body metabolism in such metabolic diseases as T2D and obesityl[11-14]. Thermogenic adipocytes, denoted as brown[15], beige[16] or brite[15,17], are distinct from the more abundant lipid storing white adipocytes not only by their high oxidative capacity and expression of mitochondrial uncoupling protein (UCP1), but also by their secretion of factors that enhance energy metabolism and energy expenditure[11-14]. One example is the secretion from brown and beige adipose tissue of neuroregulin 4 (NRG4) which has been shown to decrease hepatic lipid accumulation and improve glucose homeostasis in mice[18,19].

Multiple studies have demonstrated that implantation of mouse brown adipose tissue into obese, glucose intolerant mice can improve glucose tolerance and insulin sensitivity[20-22]. However, a bottleneck in taking advantage of this approach for therapeutic strategies in humans has been the scarcity of human beige adipocytes. Recently, human white and beige adipocytes expanded ex vivo from small samples of subcutaneous adipose tissue were shown to form robust thermogenic adipose tissue depots upon implantation into immune-compromised obese mice and to lower blood glucose levels[23]. Collectively, these data provide the framework to now apply genetic modifications to human adipocytes to further improve their therapeutic potential. The advent of clustered regularly interspaced short palindromic repeats (CRISPR) methods have greatly advanced progress towards enhanced cell therapy approaches[24,25]. Such genetic modifications must be performed by methods that minimize off target effects and eliminate the presence of foreign reagent proteins in adipocytes prior to their implantation, which are major goals of studies descripted herein.

The Nrip1 gene is an attractive target to enhance the therapeutic potential of adipocytes in obesity and diabetes. NIRP1 protein (also denoted as RIP140) had been shown to strongly suppress glucose transport, fatty acid oxidation, mitochondrial respiration, UCP1 expression as well as secretion of such metabolically beneficial factors including neuroregulin 4[26-28]. NRIP1 protein functions as a transcriptional co-repressor that attenuates activity of multiple nuclear receptors involved in energy metabolism, including estrogen related receptor (ERRα), peroxisome proliferator activated receptor (PPARγ), and thyroid hormone receptor (TH)[29]. NRIP 1 knockout in white adipocytes upregulates genes that are highly expressed in brown adipocytes, enhancing glucose and fatty acid utilization and generating heat. Nrip1 ablation in mice elicits a lean phenotype under high fat diet conditions, and greatly enhances energy expenditure, glucose tolerance and insulin sensitivity[26]. However, NRIP 1 is not an attractive target for conventional pharmacological intervention as it is not an enzyme, and it also has a multiplicity of tissue specific roles such as regulating the estrogen receptor in the reproductive tract[29]. Thus, targeting NRIP 1 selectively within adipocytes ex vivo represents an ideal approach to capture its therapeutic potential without undesirable side effects.

A major goal of the studies described herein was to advance the application of CRISPR technology to metabolic disease in the context of a potential therapeutic strategy. The starting point of the experimental plan was the success of many laboratories in demonstrating the efficacy of implanting mouse or human brown/beige adipocytes into glucose intolerant mice to alleviate diabetes[21,23,40-42]. Five key criteria were incorporated into the approach described herein: 1. Generation of large numbers of adipocyte progenitors from small samples of human adipose tissue, 2. Identification of a strong suppressor of adipocyte beiging for targeting by CRISPR to optimize the therapeutic benefit of adipocyte implantation, 3. Stealth administration of SpyCas9/sgRNA to cells that would not expose recipient mice to immunogenic reagents, 4. Minimizing off target effects, and 5. High efficiency gene disruption in which most cells ex vivo are affected in a single step without a cell selection step. Taken together, the data presented herein show that the methods described herein using CRISPR-based RNPs targeting Nrip1 to a large extent satisfy the above criteria. These methods can indeed enhance browning of mouse or human adipocytes ex vivo at high efficiency without the use of expression vectors to improve glucose homeostasis in obese mice.

Targeting Nrip1 in these studies proved highly effective, consistent with previous studies by other laboratories[26,29] and ours[27,28] indicating that NRIP1 is one of the most powerful suppressors of adipocyte beiging. Importantly, NRIP1 deletion in preadipocytes does not diminish differentiation of these cells into adipocytes. Although CRISPR-based upregulation of UCP1 alone in implanted adipocytes can improve metabolism in mice[31], targeting NRIP1 has the advantage of upregulating expression of many genes that have favorable metabolic effects in addition to UCP1 as well as secreted factors such as NRG4. Moreover, NRIP1 disruption synergizes with the cAMP pathway (FIG. 5h), known in adipocytes to have broad effects on mitochondrial respiration and metabolism[43]. Since UCP1 expression in NRIP1KO adipocytes does not reach the level of mouse BAT, our approach can likely be improved by further enhancing adipocyte browning through disrupting combinations of targets in addition to NRIP1. Indeed, it was found that simultaneous delivery of multiple sgRNAs into preadipocytes each yield high efficiencies of indel formation, offering the potential for disrupting multiple thermogenic suppressor genes to achieve greater therapeutic potential.

The specific technical approach presented here also has several additional advantages, including the rapid electroporation procedure with minimal loss of viability of the transfected preadipocytes. Also, the brief exposure of cells to Cas9/sgRNA that we document here (FIGS. 10a-10l) reduces the potential for off target effects that are produced by long term expression of these reagents. The immunogenic SpyCas9 is readily degraded within the adipocytes prior to implantation (FIG. 1b), minimizing off target effects (FIGS. 11a-11f). Indeed, studies described herein showed that while significant off-target indels were observed in the mouse preadipocytes, no significant off-target gene disruptions in the human progenitors were observed over background in a rigorous application of GUIDEseq and deep sequencing (FIGS. 11a-11f). To further enhance the on-target effects and reduce off-target effects of the work described here, the use of high fidelity nucleases[44,45] can be explored and would further maximize cell viability and functionality. Altogether, the experiments reported herein advance a powerful strategy for cell therapy in metabolic disease that can serve as a framework for testing in larger animals towards the longer-term goal of clinical trials.

Accordingly, the present disclosure provides, in some aspects, therapeutic uses of engineered adipocytes for treating a condition associated with an elevated body mass index (BMI) such as metabolic syndrome, prediabetes, type 2 diabetes, lipodystrophy, cardiovascular disease, nephropathy, neuropathy, dyslipidemia, diabetic foot syndrome (DFS), leg or foot ulcers, impaired wound healing, fatty liver disease, or a combination thereof.

I. Methods of Making Engineered Adipocytes

Aspects of the present disclosure provide methods of making engineered adipocytes comprising a disrupted Nrip1 gene. In some examples, methods include making engineered adipocytes comprising more than one gene edit (e.g., in more than one gene). Any gene editing method suitable for disrupting a target gene can be used including engineered nucleases and inhibitory nucleic acids.

In general, methods of making engineered adipocytes can comprise obtaining a population of adipose progenitor cells and engineering the adipose progenitor cells to disrupt expression of Nrip1. In some examples, the adipose progenitor cells are differentiated to mature adipose cells prior to therapeutic use.

Obtaining Adipose Progenitor Cells

The present methods involve adipose progenitor cells (also referred to as preadipocytes) that can be genetically modified, expanded, and differentiated into mature adipose cells (also referred to as adipocytes) for use in treating subjects.

Adipose progenitor cells include primary adipose progenitor cells and Human Adipose Capillary Progenitor Cells (HACAPS), which are subcutaneous adipose tissue fragments cultured ex-vivo (e.g., embedded in MatriGel and incubated in the presence of angiogenic growth factor) to produce capillary networks that contain adipocyte progenitor cells. HACAPS are capable of giving rise to either white or "Brown-on-white" (Brite) adipose cells, and brite cells produced thereby, e.g., as described in U.S. Pat. Nos. 10,927,348 and 10,093,902, the relevant disclosures of which are incorporated by reference herein for the subject matter and purpose referenced herein.

Primary adipose cells can be obtained from tissue, e.g., by standard methods such a biopsy or other surgical methods. For example, panniculectomy surgery, liposuction, bariatric surgery, or needle biopsy can be is used to obtain tissue that is can be a source of primary adipose progenitor cells. A mixture of primary cells is typically obtained from tissue. Accordingly, in some examples, the tissue is then dissociated into cells, using known methods, such as mechanical disruption, trituration, or enzymatic digestion or explanting. If enzymatic digestion is used, enzymes such as collagenase, hyaluronidase, dispase, pronase, trypsin, elastase and chymotrypsin can be used. Any method can be used to obtain adipose progenitor cells so long as the cells thus obtained are viable.

In some embodiments, adipose progenitor cells can be sorted or immunoadsorbed based on the expression of one or more cell surface markers to produce enriched populations of cells. Methods for sorting cells are known in the art, and include flow cytometry, e.g., fluorescence activated cell sorting (FACS), using fluorescently labeled antibodies that recognize the cell surface markers. When fluorescence detection is used, the primary antibodies can be labeled, or can be detected using labeled secondary antibodies. Suitable antibodies are known in the art and commercially available.

In some embodiments, adipose progenitor cells are enriched (e.g., by cell sorting), the cells are plated and then maintained in culture to proliferate. For example, after enrichment, the adipose progenitor cells can be plated and expanded in culture. In some embodiments, the adipose progenitor cells are resuspended in media (the cells can be genetically modified at this time) and further cultured and passaged, and differentiated.

In some embodiments, the adipose progenitor cells are used to seed biocompatible hydrogel scaffolds, which may be implanted directly, or after the seeded cells within the scaffold have been induced to differentiate in vitro into adipocytes, e.g., by incubation in the presence of methyl-isobutil-xanthine, dexamethasone and insulin (MDI) (e.g., synthetic glucocorticoid dexamethasone, the cAMP elevating agent 1-methyl-3-isobutyl xanthine (MIX), and pharmacological doses of insulin; see Hwang et al., *Annu Rev Cell Dev Biol* 13: 231-259).

Differentiating Adipose Progenitor Cells

Adipose progenitor cells can be differentiated using any method known in the art. For example, to differentiate into brite fat cells, the HACAPS can be cultured, e.g., in proprietary media EGM2-MV (Lonza) or a formulation consisting of Media 199 supplemented with glucose (e.g., 10 mM), ascorbic acid (e.g., 500 mM), hydrocortisone (e.g., 1 µM) and human recombinant FGF-2 (e.g., 0.1 nM), until confluence is reached, and then exposed to adipogenic cocktail, e.g., comprising DMEM containing 10% (v/v) FBS, 3-isobutyl-1-methylxanthine (e.g., 500 µM), dexamethasone (e.g., 100 nM) and insulin (e.g., 1 µM) for 3 days. The cells are then cultured for an additional time, e.g., 5-10 days, e.g., 7 days in media, e.g., in DMEM containing 10% (v/v) FBS, and then in the same medium supplemented with adenylate cyclase activators such as forskolin (e.g., 1 µM) or adrenergic agonists such as isoproterenol (e.g., 10 µM), epinephrine (e.g., 10 µM), norepinephrine (e.g., 10 µM), terbutaline (e.g., 10 µM) or dobutamine (e.g., 10 µM) or to thyroid hormone (T3, e.g., 10 µM) for 1 week to induce differentiation of the HACAPS into brite cells. These methods are exemplary, and other methods can also be used.

The adipose progenitor cells (e.g., HACAPS) can be differentiated into adipocytes and cultured, e.g., in the presence of forskolin or adrenergic agonists such as isoproterenol, epinephrine, norepinephrine, terbutaline or dobutamine, or the thyroid hormone tri-iodo-thyronine (T3), to induce a brite adipocyte phenotype.

In some embodiments, the adipose progenitor cells are differentiated to mature adipocytes prior to transplantation into a subject. In some embodiments, the adipose progenitor cells are genetically engineered prior to differentiation. In some embodiments, the adipose progenitor cells are maintained in culture, differentiated into adipocytes (e.g., by incubation in the presence of MDI), and then used for treating a subject.

Populations of Adipose Progenitor Cells

The present disclosure also provides enriched populations of engineered adipose progenitor cells, i.e., populations of cells isolated and engineered by a method described herein. In some embodiments, the enriched populations comprise primary cells, i.e., cells that have never been plated but were obtained directly from an animal, e.g., a mammal, e.g., an experimental animal or a human or veterinary subject, or cells that are being plated for the first time.

Also within the scope of the present disclosure are populations of genetically engineered adipose cells (e.g., progenitor cells or mature cells) comprising a disrupted Nrip1 gene. In some embodiments, the population of genetically engineered adipose cells comprises a disrupted Nrip1 gene and an additional gene edit such as a disrupted gene involved in negative regulation of cAMP levels (e.g., a disrupted PDE gene, a disrupted $G_{ai}$ gene, a disrupted adenosine receptor gene, a disrupted PKA gene, or a combination thereof). In some embodiments, at least 50% (e.g., 60%, 70%, 80%, 90%, or 95%) of the population of engineered adipose cells produced by methods described herein do not express a detectable level of a disrupted gene (e.g., a detectable level of Nrip1).

Genetic Editing of Adipose Progenitor Cells

Genetic modification of adipose cells can be performed at any time in methods described herein, e.g., before enrichment for adipose progenitor cells, after enrichment but before expansion, after expansion but before differentiation, or after differentiation.

(a) Gene Edits

The present disclosure provide methods of making engineered adipocytes comprising one or more disrupted genes including a disrupted Nrip1 gene.

As used herein, the term "a disrupted gene" refers to a gene containing one or more mutations (e.g., insertion, deletion, substitution) relative to the wild-type counterparts so as to substantially reduce or completely eliminate the activity of the encoded gene product. The one or more mutations can be located in an non-coding region (e.g., a promoter region, a regulatory region, an intron). Alternatively, or in addition to, the one or more mutations can be located in a coding region (e.g., an exon). In some examples, the disrupted gene does not express or expresses a substantially reduced level of the encoded protein. In some examples, the disrupted gene expresses the encoded protein in a mutated form, which is either not functional or has substantially reduced activity. In some examples, a disrupted gene is a gene that does not encode a functional protein. In some examples, an engineered adipocyte comprising a disrupted gene (e.g., a disrupted Nrip1 gene) does not express a detectable level of the protein encoded by the gene.

In some embodiments, methods described herein comprise introducing a mutation into a target region of the Nrip1 gene. In some embodiments, the target region comprises nucleotides 596-3811, 596-3110, 665-3811, or 665-3110 of exon 4 of the Nrip1 gene as provided in SEQ ID NO: 21.

In some embodiments, the target region comprises a region between nucleotides 250, 300, 350, 400, 450, or 500 on the 5' end and nucleotides 2950, 3000, 3050, 3100, or 3110 on the 3' end (and all ranges with any of the foregoing values as endpoints) of exon 4 of the Nrip1 gene as provided in SEQ ID NO: 21.

In some embodiments, the target region comprises a region between nucleotides 250, 300, 350, 400, 450, 500, or 550 on the 5' end and nucleotides 750, 800, 850, or 100 on the 3' end (and all ranges with any of the foregoing values as endpoints) of exon 4 of the Nrip1 gene as provided in SEQ ID NO: 21.

In some embodiments, the target region comprises a region between nucleotides 2500, 2550, 2600, 2650, 2750, or 2800 on the 5' end and nucleotides 2950, 3000, 3050, 3100, or 3110 on the 3' end (and all ranges with any of the foregoing values as endpoints) of exon 4 of the Nrip1 gene as provided in SEQ ID NO: 21.

In some embodiments, the target region comprises a region comprising any of the target regions the human Nrip1 gene shown in Table 1 below, plus up to 50, 75, 100, 200, 300, 400, 500, 750, or 1000 nucleotides on either side.

TABLE 1

Target regions of the human Nrip1 gene.

| Region | Location/Size |
| --- | --- |
| Exon 4 | 0-7292 |
| 5'UTR | 0-334 |
| TSS | 335-337 |
| Coding region | 335-3811 |
| sgRNA-188 (H1) | 322-342 |
| sgRNA-159 (H2) | 351-371 |
| sgRNA-969 (H3) | 541-561 |
| sgRNA-593 (H4) | 931-951 |
| sgRNA-475 (H5) | 1035-1055 |
| sgRNA-622 (H6) | 2888-2908 |
| STOP codon | 3809-3811 |
| 3'UTR | 3812-7292 |

In some embodiments, the target region of the Nrip1 gene comprises the nucleic acid sequence of SEQ ID NO: 21 or a nucleic acid sequence that is at least 80%, 85%, 90%, 85%, 97%, 98%, 99%, or 100% identical to SEQ ID NO: 21.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 80% (in some embodiments, about 85%, 90%, 95%, or 100% of the length of the reference sequence) is aligned. The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch ((1970)*J. Mol. Biol.* 48:444-453) algorithm which has been incorporated into the GAP program in the GCG software package, using a Blossum 62 scoring matrix with a gap penalty of 12, a gap extend penalty of 4, and a frameshift gap penalty of 5.

In some embodiments, methods described herein comprise introducing a mutation into the Nrip1 gene and an additional gene. In some embodiments, the additional gene is involved in negative regulation of cAMP levels. Non-limiting examples of a gene involved in negative regulation of cAMP levels include a phosphodiesterase (PDE) gene, an inhibitory G protein ($G_{\alpha i}$) gene, an adenosine receptor gene, and a protein kinase A (PKA) gene.

Methods described herein encompass introducing a mutation into any isoform of a gene involved in negative regulation of cAMP levels. For example, when methods comprise introducing a mutation into a PDE gene, methods can comprise introducing a mutation into a PDE1 gene, a PDE2 gene, a PDE3 gene, a PDE4 gene, a PDE5 gene, a PDE6 gene, a PDE7 gene, a PDE8 gene, a PDE9 gene, a PDE10 gene, a PDE11 gene, or a combination thereof.

In another example, when methods comprise introducing a mutation into an adenosine receptor gene, methods can comprise introducing a mutation into an $A_1$ gene, an $A_{2A}$ gene, an $A_{2B}$ gene, an $A_3$ gene, or a combination thereof.

(b) Engineered Nucleases

The present methods can include engineering adipose cells using an engineered nuclease to disrupt a target gene such as Nrip1.

The engineered nuclease can be transiently or stably expressed in the adipose cell, using methods known in the art; typically, to obtain expression, a sequence encoding a protein is subcloned into an expression vector that contains a promoter to direct transcription. Suitable eukaryotic expression systems are well known in the art and described, e.g., in Sambrook et al., *Molecular Cloning, A Laboratory Manual* (4th ed. 2013); Kriegler, *Gene Transfer and Expression: A Laboratory Manual* (2006); and *Current Protocols in Molecular Biology* (Ausubel et al., eds., 2010). Transformation of adipose cells can be performed according to standard techniques (see, e.g., the reference above and Morrison, 1977, J. Bacteriol. 132:349-351; Clark-Curtiss & Curtiss, *Methods in Enzymology* 101:347-362 (Wu et al., eds, 1983).

Alternatively, the engineered nuclease can be expressed and purified and introduced into adipose cells as purified proteins or protein complexes.

There are presently four main classes of engineered nucleases: (1) meganucleases, (2) Clustered Regularly Interspaced Short Palindromic Repeats (CRISPR) Cas RNA-guided nucleases (RGN) (3) zinc-finger nucleases, and (4) transcription activator effector-like nucleases (TALEN). Each are described below. Also see, e.g., Gaj et al., *Trends Biotechnol.* 2013 July; 31(7):397-405.

(1) Meganucleases

Meganucleases are sequence-specific endonucleases originating from a variety of organisms such as bacteria, yeast, algae and plant organelles. Endogenous meganucleases have recognition sites of 12 to 30 base pairs; customized DNA binding sites with 18 bp and 24 bp-long meganuclease recognition sites have been described, and either can be used in the present methods and constructs. See, e.g., Silva, G., et al., *Current Gene Therapy*, 11:11-27, (2011); Arnould et al., *Journal of Molecular Biology*, 355:443-58 (2006); Arnould et al., *Protein Engineering Design & Selection*, 24:27-31 (2011); and Stoddard, Q. *Rev. Biophys.* 38, 49 (2005); Grizot et al., *Nucleic Acids Research*, 38:2006-18 (2010).

(2) RNA-Guided Nucleases (RGNs) and Guide RNAs

The present methods include the use of RNA-guided nucleases (RGNs) targeted to a target region of the Nrip1 gene as described herein, to engineer adipocytes to disrupt the expression of Nrip1 and increase expression of UCP1. The methods can include the use of RGNs including Cas9, Cpf1, and orthologs thereof.

The Cas9 nuclease from *S. pyogenes* can be guided via simple base pair complementarity between 17-20 nucleotides of an engineered guide RNA (gRNA), e.g., a single guide RNA or crRNA/tracrRNA pair, and the complementary strand of a target genomic DNA sequence of interest that lies next to a protospacer adjacent motif (PAM), e.g., a PAM matching the sequence NGG or NAG (Shen et al., *Cell Res* (2013); Dicarlo et al., Nucleic Acids Res (2013); Jiang et al., *Nat Biotechnol* 31, 233-239 (2013); Jinek et al., *Elife* 2, e00471 (2013); Hwang et al., *Nat Biotechnol* 31, 227-229 (2013); Cong et al., Science 339, 819-823 (2013); Mali et al., *Science* 339, 823-826 (2013c); Cho et al., *Nat Biotechnol* 31, 230-232 (2013); Jinek et al., *Science* 337, 816-821 (2012)). The engineered CRISPR from Prevotella and Francisella 1 (Cpf1, also known as Cas12a) nuclease can also be used, e.g., as described in Zetsche et al., *Cell* 163, 759-771 (2015); Schunder et al., *Int. J Med Microbiol* 303, 51-60 (2013); Makarova et al., *Nat Rev Microbiol* 13, 722-736 (2015); Fagerlund et al., *Genome Biol* 16, 251 (2015). Unlike SpCas9, Cpf1/Cas12a requires only a single 42-nt crRNA, which has 23 nt at its 3' end that are complementary to the protospacer of the target DNA sequence (Zetsche et al., 2015). Furthermore, whereas SpCas9 recognizes an NGG PAM sequence that is 3' of the protospacer, AsCpf1 and LbCp1 recognize TTTN PAMs that are found 5' of the protospacer (Zetsche et al., 2015).

In some embodiments, the present system utilizes a wild type or variant Cas9 protein from *S. pyogenes* or *Staphylococcus aureus*, or a wild type or variant Cpf1 protein from Acidaminococcus sp. BV3L6 or Lachnospiraceae bacterium ND2006 either as encoded in bacteria or codon-optimized for expression in mammalian cells and/or modified in its PAM recognition specificity and/or its genome-wide specificity. A number of variants have been described; see, e.g., WO 2016/141224, PCT/US2016/049147, Kleinstiver et al., *Nat Biotechnol.* 2016 August; 34(8):869-74; Tsai and Joung, *Nat Rev Genet.* 2016 May; 17(5):300-12; Kleinstiver et al., *Nature.* 2016 Jan. 28; 529(7587):490-5; Shmakov et al., *Mol Cell.* 2015 Nov. 5; 60(3):385-97; Kleinstiver et al., *Nat Biotechnol.* 2015 December; 33(12):1293-1298; Dahlman et al., *Nat Biotechnol.* 2015 November; 33(11):1159-61; Kleinstiver et al., *Nature.* 2015 Jul. 23; 523(7561):481-5; Wyvekens et al., *Hum Gene Ther.* 2015 July; 26(7):425-31; Hwang et al., *Methods Mol Biol.* 2015; 1311:317-34; Osborn et al., *Hum Gene Ther.* 2015 February; 26(2):114-26; Konermann et al., *Nature.* 2015 Jan. 29; 517(7536):583-8; Fu et al., *Methods Enzymol.* 2014; 546:21-45; and Tsai et al., *Nat Biotechnol.* 2014 June; 32(6):569-76, inter alia.

Cas9 and analogs are shown in Table 2, and engineered protospacer-adjacent motif (PAM) or high-fidelity variants are shown in Table 3.

TABLE 2

List of Exemplary Cas9 or Cas12a Orthologs.

| Ortholog | UniProt or GenBank Accession Number |
|---|---|
| *S. pyogenes* Cas9 (SpCas9) | Q99ZW2.1 |
| *S. aureus* Cas9 (SaCas9) | J7RUA5.1 |
| *S. thermophilus* Cas9 (St1Cas9) | G3ECR1.2 |
| *S. pasteurianus* Cas9 (SpaCas9) | BAK30384.1 |
| *C. jejuni* Cas9 (CjCas9) | Q0P897.1 |
| *F. novicida* Cas9 (FnCas9) | A0Q5Y3.1 |
| *P. lavamentivorans* Cas9 (PlCas9) | A7HP89.1 |
| *C. lari* Cas9 (ClCas9) | G1UFN3.1 |
| *Pasteurella multocida* Cas9 | Q9CLT2.1 |
| *F. novicida* Cpf1 (FnCpf1) | A0Q7Q2.1 |
| *M. bovoculi* Cpf1 (MbCpf1) | WP_052585281.1 |
| *A.* sp. BV3L6 Cpf1 (AsCpf1) | U2UMQ6.1 |
| *L. bacterium* N2006 (LbCpf1) | A0A182DWE3.1 |

TABLE 3

List of Exemplary High Fidelity and/or PAM-relaxed RGN Orthologs.

| Published HF/PAM-RGN variants | PMID/U.S. Ser. No. | Mutations* |
|---|---|---|
| *S. pyogenes* Cas9 (SpCas9) eSpCas9 | 26628643 | K810A/K1003A/R1060A (1.0); K848A/K1003A/R1060A(1.1) |
| *S. pyogenes* Cas9 (SpCas9) evoCas9 | 29431739 | M495V/Y515N/K526E/R661Q; (M495V/Y515N/K526E/R661S; M495V/Y515N/K526E/R661L) |
| *S. pyogenes* Cas9 (SpCas9) HF1 | 26735016 | N497A/R661A/Q695A/Q926A |
| *S. pyogenes* Cas9 (SpCas9) HiFi Cas9 | 30082871 | R691A |
| *S. pyogenes* Cas9 (SpCas9) HypaCas9 | 28931002 | N692A, M694A, Q695A, H698A |
| *S. pyogenes* Cas9 (SpCas9) Sniper-Cas9 | 30082838 | F539S, M763I, K890N |
| *S. pyogenes* Cas9 (SpCas9) xCas9 | 29512652 | A262T, R324L, S409I, E480K, E543D, M694I, E1219V |
| *S. pyogenes* Cas9 (SpCas9) SpCas9-NG | 30166441 | R1335V, L1111R, D1135V, G1218R, E1219F, A1322R, T1337R |
| *S. pyogenes* Cas9 (SpCas9) VQR/VRER | 26098369 | D1135V, R1335Q, T1337R; D1135V/G1218R/R1335E/T1337R |
| *S. aureus* Cas9 (SaCas9)-KKH | 26524662 | E782K/N968K/R1015H |
| enAsCas12a | U.S. Ser. No. 15/960,271 | One or more of: E174R, S170R, S542R, K548R, K548V, N551R, N552R, K607R, K607H, e.g., E174R/S542R/K548R, E174R/S542R/K607R, E174R/S542R/K548V/N552R, S170R/S542R/K548R, S170R/E174R, E174R/S542R, S170R/S542R, E174R/S542R/K548R/N551R, E174R/S542R/K607H, S170R/S542R/K607R, or S170R/S542R/K548V/N552R |
| enAsCas12a-HF | U.S. Ser. No. 15/960,271 | One or more of: E174R, S542R, K548R, e.g., E174R/S542R/K548R, E174R/S542R/K607R, E174R/S542R/K548V/N552R, S170R/S542R/K548R, S170R/E174R, E174R/S542R, S170R/S542R, E174R/S542R/K548R/N551R, E174R/S542R/K607H, S170R/S542R/K607R, or S170R/S542R/K548V/N552R, with the addition of one or more of: N282A, T315A, N515A and K949A |
| enLbCas12a(HF) | U.S. Ser. No. 15/960,271 | One or more of T152R, T152K, D156R, D156K, Q529K, G532R, G532K, G532Q, K538R, K538V, |

TABLE 3-continued

List of Exemplary High Fidelity and/or PAM-relaxed RGN Orthologs.

| Published HF/PAM-RGN variants | PMID/U.S. Ser. No. | Mutations* |
|---|---|---|
| | | D541R, Y542R, M592A, K595R, K595H, K595S or K595Q, e.g., D156R/G532R/K538R, D156R/G532R/K595R, D156R/G532R/K538V/Y542R, T152R/G532R/K538R, T152R/D156R, D156R/G532R, T152R/G532R, D156R/G532R/K538R/D541R, D156R/G532R/K595H, T152R/G532R/K595R, T152R/G532R/K538V/Y542R, optionally with the addition of one or more of: N260A, N256A, K514A, D505A, K881A, S286A, K272A, K897A |
| enFnCas12a(HF) | U.S. Ser. No. 15/960,271 | One or more of T177A, K180R, K180K, E184R, E184K, T604K, N607R, N607K, N607Q, K613R, K613V, D616R, N617R, M668A, K671R, K671H, K671S, or K671Q, e.g., E184R/N607R/K613R, E184R/N607R/K671R, E184R/N607R/K613V/N617R, K180R/N607R/K613R, K180R/E184R, E184R/N607R, K180R/N607R, E184R/N607R/K613R/D616R, E184R/N607R/K671H, K180R/N607R/K671R, K180R/N607R/K613V/N617R, optionally with the addition of one or more of: N305A, N301A, K589A, N580A, K962A, S334A, K320A, K978A |

*predicted based on UniRule annotation on the UniProt database.

In some embodiments an RGN sequence is modified to include one or more nuclear localization sequences (NLSs), e.g., at the C- and/or N-terminus of the RGN protein, and a mini-polyadenylation signal (or Poly-A sequence). Exemplary NLSs include SV40 large T antigen NLS (PKKKRRV (SEQ ID NO: 1)); PKKKRKV (SEQ ID NO: 2); KRTADGSEFESPKKKRKV (SEQ ID NO: 3)); and nucleoplasmin NLS KRPAATKKAGQAKKKK (SEQ ID NO: 4)). Other NLSs are known in the art; see, e.g., Cokol et al., EMBO Rep. 2000 Nov. 15; 1(5):411-415; Freitas and Cunha, Curr Genomics. 2009 December; 10(8): 550-557. An exemplary polyadenylation signal is

```
                                  (SEQ ID NO: 5)
TAGCAATAAAGGATCGTTTATTTTCATTGGAA

GCGTGTGTTGGTTTTTTGATCAGGCGCG.
```

Guide RNAs appropriate for the RGN and the target gene should be used. In some embodiments, the gRNAs used in the present disclosure can be unimolecular (also referred to as single-molecule guide RNA (sgRNA)) or modular, as known in the art. Exemplary sgRNAs targeting a Nrip1 gene are provided below in Table 1.

TABLE 1

Sequences of sgRNAs.

| Mouse Nrip1 sgRNA sequences (5'→3') | | Human NRIP1 sgRNA sequences (5'→3') | |
|---|---|---|---|
| sgRNA-M1 | CUUGUAUUGA ACAUGACUCA (SEQ ID NO: 6) | sgRNA-H1 | CUUCUAUUGA ACAUGACUCA (SEQ ID NO: 13) |
| sgRNA-M2 | AUUGUCUUAAC UUACCUCGA (SEQ ID NO: 7) | sgRNA-H2 | GCUUGGCUCU GAUGUGCACC (SEQ ID NO: 14) |
| sgRNA-M3 | GUCAGUACCCA GACGUACCA (SEQ ID NO: 8) | sgRNA-H3 | ACACAUACAU AUCAGGGGUC (SEQ ID NO: 15) |
| sgRNA-M4 | AUAAGGUUUG GAGUCACGUC (SEQ ID NO: 9) | sgRNA-H4 | ACAUCAGGAA GAUUCGUAUC (SEQ ID NO: 16) |
| sgRNA-M5 | CACUUUGUCC CACUGCGGGA (SEQ ID NO: 10) | sgRNA-H5 | GUCAUGUGCU GCAAGAUUAC (SEQ ID NO: 17) |
| sgRNA-M6 | ACAGGCUGUU GCCAGCAUGG (SEQ ID NO: 11) | sgRNA-H6 | UUUGCAUGGU CCCUAAGAAA (SEQ ID NO: 18) |
| sgRNA-M7 | GGAGUCGAAG AACAUCUGCA (SEQ ID NO: 12) | | |

Human and Mouse Non-Targeting control sgRNA (NUC):
GCACUACCAGAGCUAACUCA (SEQ ID NO: 19)

The gRNA targets a "target sequence" in a target gene. The target sequence is adjacent to a PAM sequence and is the sequence to be modified by Cas9. The target sequence is on the so-called PAM-strand in a target gene or a target nucleic acid, which is a double-stranded molecule containing the PAM-strand and a complementary non-PAM strand. One of skill in the art recognizes that the gRNA sequence hybridizes to the complementary sequence located in the non-PAM strand of the target nucleic acid. Thus, the gRNA sequence is the RNA equivalent of the target sequence.

For example, if the Nrip1 target sequence is TTTG-CATGGTCCCTAAGAAA (SEQ ID NO: 22), then the gRNA sequence is UUUGCAUGGUCCCUAAGAAA (SEQ ID NO: 18). It should be understood that when the gRNA sequence is described in terms of its target sequence, the target sequence can contain T and the gRNA sequence can contain U.

In some embodiments, the gRNA comprises a sequence of at least 10 contiguous nucleotides of a target sequence within exon 4 of the Nrip1 gene (e.g., SEQ ID NO: 21). In some embodiments, the guide RNA comprises a sequence of 15, 16, 17, 18, 19, 20, 21, 22, 23, 24, 25, 26, 27, 28, 29, 30, 31, 32, 33, 34, 35, 36, 37, 38, 39, or 40 contiguous nucleotides of a target sequence within exon 4 of the Nrip1 gene (e.g., SEQ ID NO: 21).

In some embodiments, the target sequence comprises nucleotides 596-3811, 596-3110, 665-3811, or 665-3110 within exon 4 of the Nrip1 gene (e.g., SEQ ID NO: 21).

In some embodiments, the target sequence comprises nucleotides 250, 300, 350, 400, 450, or 500 on the 5' end and nucleotides 2950, 3000, 3050, 3100, or 3110 on the 3' end (and all ranges with any of the foregoing values as endpoints) within exon 4 of the Nrip1 gene (e.g., SEQ ID NO: 21).

In some embodiments, the target sequence comprises nucleotides 250, 300, 350, 400, 450, 500, or 550 on the 5' end and nucleotides 750, 800, 850, or 100 on the 3' end (and all ranges with any of the foregoing values as endpoints) within exon 4 of the Nrip1 gene (e.g., SEQ ID NO: 21).

In some embodiments, the target sequence comprises nucleotides 2500, 2550, 2600, 2650, 2750, or 2800 on the 5' end and nucleotides 2950, 3000, 3050, 3100, or 3110 on the 3' end (and all ranges with any of the foregoing values as endpoints) within exon 4 of the Nrip1 gene (e.g., SEQ ID NO: 21).

In some embodiments, the target sequence comprises any of the target regions of the human Nrip1 gene shown in Table 1, plus up to 50, 75, 100, 200, 300, 400, 500, 750, or 1000 nucleotides on either side.

In some embodiments, the degree of complementarity between the gRNA sequence and the target sequence in the target gene (e.g., the Nrip1 gene) can be about 60%, about 65%, about 70%, about 75%, about 80%, about 85%, about 90%, about 95%, about 96%, about 97%, about 98%, about 99%, or 100%. In some embodiments, the gRNA sequence and the target sequence in the target gene is 100%. In some embodiments, the gRNA sequence and the target sequence in the target gene can contain up to 10 mismatches, e.g., up to 9, up to 8, up to 7, up to 6, up to 5, up to 4, up to 3, up to 2, or up to 1 mismatch.

In some embodiments, the gRNA (e.g., sgRNA) is from 15-100 nucleotides long (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides long).

Any of the gRNAs disclosed herein, including any of the sgRNAs, can be modified or unmodified. In some embodiments, the gRNA can include one or more modified nucleotides and/or modified backbones. In some embodiments, a modified gRNA such as an sgRNA can comprise one or more 2'-O-methyl phosphorothioate nucleotides, which can be located at either the 5' end, the 3' end, or both.

(3) Zinc Finger Nucleases (ZFNs)

ZFNs are enzymes generated by fusing a zinc finger DNA-binding domain to a DNA-cleavage domain, thereby enabling ZFNs to recognize and target highly specific chromosomal sequences to facilitate disruption of a target gene (e.g., the Nrip1 gene). These nucleases exploit endogenous cellular mechanisms for homologous recombination and repair of double stranded breaks in genetic material. ZFNs can be used to target a wide variety of endogenous nucleic acid sequences in a cell or organism.

The ZFN can include multiple (e.g., at least 3, at least 4, at least 5, at least 6, at least 7, at least 8, at least 9 or more)) zinc fingers in order to improve its target specificity. The zinc finger domain can be derived from any class or type of zinc finger. For example, the zinc finger domain can include the Cys2His2 type of zinc finger that is very generally represented, for example, by the zinc finger transcription factors TFIIIA or Sp1. In a preferred embodiment, the zinc finger domain comprises three Cys2His2 type zinc fingers.

The DNA-cleavage domain of the ZFN can be derived from a class of non-specific DNA cleavage domains, for example the DNA-cleavage domain of a Type II restriction enzyme such as FokI. Thus, a ZFN useful in the present methods can include three Cys2His2 type zinc fingers and a DNA-cleavage domain derived from the Type II restriction enzyme FokI. In this event, each zinc finger contacts three consecutive base pairs of DNA creating a 9 bp recognition sequence for the ZFN DNA binding domain. The DNA-cleavage domain of the embodiment requires dimerization of two ZFN DNA-cleavage domains for effective cleavage of double-stranded DNA. This imposes a requirement for two inverted recognition (target DNA) sites within close proximity for effective targeted genetic recombination. If all positions in the target sites are contacted specifically, these requirements enforce recognition of a total of 18 base pairs of DNA. There may be a space between the two sites. The space between recognition sites for ZFNs may be equivalent to 6 to 35 bp of DNA. The region of DNA between the two recognitions sites may be referred to as the "spacer."

A linker, if present, between the cleavage and recognition domains of the ZFN can be a sequence of amino acid residues that result in a flexible linker, although linkerless constructs tend to improve target site specificity. A linkerless construct has a strong preference for binding to and then cleaving between recognition sites that are 6 bp apart. However, with linker lengths of between 0 and about 18 amino acids in length, ZFN-mediated cleavage occurs between recognition sites that are between 5 and 35 bp apart. For a given linker length, there will be a limit to the distance between recognition sites that is consistent with both binding and dimerization. As noted, there may be no linker between the cleavage and recognition domains, and the target locus can include two nine nucleotide recognition sites in inverted orientation with respect to one another, separated by a six nucleotide spacer.

To target genetic recombination or mutation, two 9 bp zinc finger DNA recognition sequences are identified in the host DNA. These recognition sites will be in an inverted orientation with respect to one another and separated by about 6 bp of DNA. ZFNs are then generated by designing and producing zinc finger combinations that bind DNA specifically at the target locus, and then linking the zinc fingers to a DNA-cleavage domain.

(4) Transcription Activator-Like Effector Nulceases (TALENs)

TALENs function in a manner somewhat similar to ZFNs, in that they can be used to induce sequence-specific cleavage; see, e.g., Hockemeyer et al., *Nat Biotechnol.* 29(8): 731-4 (2011); Moscou et al., 2009, *Science* 326:1501; Boch et al., 2009, *Science* 326:1509-1512. Methods are known in the art for designing TALENs, see, e.g., Rayon et al., *Nature Biotechnology* 30:460-465 (2012).

Methods for generating engineered TALE arrays are known in the art, see, e.g., the fast ligation-based automatable solid-phase high-throughput (FLASH) system described in U.S. Ser. No. 61/610,212, and Reyon et al., *Nature Biotechnology* 30, 460-465 (2012); as well as the methods described in Bogdanove & Voytas, *Science* 333, 1843-1846 (2011); Bogdanove et al., *Curr Opin Plant Biol* 13, 394-401 (2010); Scholze & Boch, *J Curr Opin Microbiol* (2011); Boch et al., *Science* 326, 1509-1512 (2009); Moscou & Bogdanove, *Science* 326, 1501 (2009); Miller et al., *Nat Biotechnol* 29, 143-148 (2011); Morbitzer et al., *T. Proc Natl Acad Sci USA* 107, 21617-21622 (2010); Morbitzer et al., *Nucleic Acids Res* 39, 5790-5799 (2011); Zhang et al., *Nat Biotechnol* 29, 149-153 (2011); Geissler et al., *PLoS ONE* 6, e19509 (2011); Weber et al., *PLoS ONE* 6, e19722 (2011); Christian et al., *Genetics* 186, 757-761 (2010); Li et al., *Nucleic Acids Res* 39, 359-372 (2011); Mahfouz et al., *Proc Natl Acad Sci USA* 108, 2623-2628 (2011); Mussolino et al., *Nucleic Acids Res* (2011); Li et al., *Nucleic Acids Res* 39, 6315-6325 (2011); Cermak et al., *Nucleic Acids Res* 39, e82 (2011); Wood et al., *Science* 333, 307 (2011); Hockemeye et al. *Nat Biotechnol* 29, 731-734 (2011); Tesson et al., *Nat Biotechnol* 29, 695-696 (2011); Sander et al., *Nat Biotechnol* 29, 697-698 (2011); Huang et al., *Nat Biotechnol* 29, 699-700 (2011); and Zhang et al., *Nat Biotechnol* 29, 149-153 (2011); all of which are incorporated herein by reference in their entirety.

Also suitable for use in the present methods are Mega-TALs, which are a fusion of a meganuclease with a TAL effector; see, e.g., Boissel et al., *Nucl. Acids Res.* 42(4): 2591-2601 (2014); Boissel and Scharenberg, *Methods Mol Biol.* 2015; 1239:171-96.

(c) Inhibitory Nucleic Acids

Alternatively, the present methods can include the use of inhibitory nucleic acids that are directed to the target region of Nrip1. Inhibitory nucleic acids useful in the present methods and compositions include antisense oligonucleotides, ribozymes, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics that hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112.

(d) Delivery to Adipose Cells

Nucleic acids and proteins involved in gene editing can be delivered to adipose cells using any method suitable for delivery of such into the adipose cells. For example, sequences encoding an inhibitory nucleic acid or an engineered nuclease (e.g., meganuclease, ZFN, TALEN, or RGN and guide RNA) can be delivered to the cells using a viral vector. Described herein are targeted expression vectors for in vivo transfection and expression of a polynucleotide that encodes a engineered nuclease, e.g., RGN and guide RNA, as described herein in adipocytes. Expression constructs of such components can be administered in any effective carrier, e.g., any formulation or composition capable of effectively delivering the component gene to the cells. Approaches include insertion of the gene in viral vectors, including recombinant retroviruses, adenovirus, adeno-associated virus, lentivirus, and herpes simplex virus-1, alphavirus, vaccinia virus, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), cationic dendrimers, inorganic vectors (e.g., iron oxide magnetofection), lipidoids, cell-penetrating peptides, cyclodextrin polymer (CDP), polylysine conjugates, gramacidin S, artificial viral envelopes or other such intracellular carriers, as well as direct injection of the gene construct or $CaPO_4$ precipitation carried out in vivo.

An exemplary approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Viral vectors can be used as a recombinant gene delivery system for the transfer of exogenous genes in vivo, particularly into humans. These vectors provide efficient delivery of genes into cells, and in some cases the transferred nucleic acids are stably integrated into the chromosomal DNA of the host. Protocols for producing recombinant viruses and for infecting cells in vitro or in vivo with such viruses can be found in Ausubel, et al., eds., *Gene Therapy Protocols Volume* 1: *Production and In Vivo Applications of Gene Transfer Vectors*, Humana Press, (2008), pp. 1-32 and other standard laboratory manuals.

A preferred viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., *Curr. Topics in Micro and Immunol.* 158:97-129 (1992); see also Domenger and Grimm, *Human Molecular Genetics,* 28(R1): R3-R14 (October 2019)). AAV vectors efficiently transduce various cell types and can produce long-term expression of transgenes in vivo. Although AAV vector genomes can persist within cells as episomes, vector integration has been observed (see for example Deyle and Russell, *Curr Opin Mol Ther.* 2009 August; 11(4): 442-447; Asokan et al., *Mol Ther.* 2012 April; 20(4): 699-708; Flotte et al., *Am. J. Respir. Cell. Mol. Biol.* 7:349-356 (1992); Samulski et al., *J. Virol.* 63:3822-3828 (1989); and McLaughlin et al., *J. Virol.* 62:1963-1973 (1989)). AAV vectors, particularly AAV2, have been extensively used for gene augmentation or replacement and have shown therapeutic efficacy in a range of animal models as well as in the clinic; see, e.g., Mingozzi and High, *Nature Reviews Genetics* 12, 341-355 (2011); Deyle and Russell, *Curr Opin Mol Ther.* 2009 August; 11(4): 442-447; Asokan et al., *Mol Ther.* 2012 April; 20(4): 699-708. AAV vectors containing as little as 300 base pairs of AAV can be packaged and can produce recombinant protein expression. Space for exogenous DNA is limited to about 4.5 kb.

A variety of nucleic acids have been introduced into different cell types using AAV vectors (see for example the references cited above and those cited in Asokan et al., *Molecular Therapy* (2012); 20 4, 699-708; and Hermonat et al., *Proc. Natl. Acad. Sci. USA* 81:6466-6470 (1984); Tratschin et al., *Mol. Cell. Biol.* 4:2072-2081 (1985); Wondisford et al., *Mol. Endocrinol* 2:32-39 (1988); Tratschin et al., *J. Virol.* 51:611-619 (1984); and Flotte et al., *J. Biol. Chem.* 268:3781-3790 (1993).

In some embodiments, a self-complementary AAV is used, which contains an inverted repeat genome that folds to make double-stranded DNA.

In some embodiments, preferred viral vectors are adeno-associated virus type 5 (AAV5), see, e.g., Sharma et al., *Hum Gene Ther Methods.* 2016 December; 27(6):219-227, or AAV8, see Jimenez et al., *EMBO Mol Med.* 2018 August; 10(8): e8791

Retroviruses can also be used. The development of specialized cell lines (termed "packaging cells") which produce only replication-defective retroviruses has increased the utility of retroviruses for gene therapy, and defective retroviruses are characterized for use in gene transfer for gene therapy purposes (for a review see Katz et al., *Human Gene Therapy* 24:914 (2013)). A replication defective retrovirus can be packaged into virions, which can be used to infect a target cell through the use of a helper virus by standard techniques. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993)*J. Immunol.* 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., *BioTechniques* 6:616 (1988); Rosenfeld et al., *Science* 252:431-434 (1991); and Rosenfeld et al., *Cell* 68:143-155 (1992). Suitable adenoviral vectors derived from the adenovirus strain Ad type 5 d1324 or other strains of adenovirus (e.g., Ad2, Ad3, Ad7, etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, *J. Virol.* 57:267 (1986).

In some embodiments, sequences encoding an engineered nuclease, e.g., TALE, ZFN, or RGN and guide RNAs, are entrapped in liposomes bearing positive charges on their surface (e.g., lipofectins), which can be tagged with antibodies against cell surface antigens of the target tissue (Mizuno et al., No Shinkei Geka 20:547-551 (1992); PCT publication WO91/06309; Japanese patent application 1047381; and European patent publication EP-A-43075).

The vectors can also include promoters, enhancers (e.g., CMV enhancer), other cis-regulatory elements, and/or capsid serotype variants. With regard to promoters, vectors can include promoters that drive expression in many cell types (e.g., CAG or CASI) or specifically in adipocytes (e.g., adiponectin or adipocyte P2 (aP2) promoter). Other cis-regulatory elements can include woodchuck hepatitis virus post-transcriptional regulatory element (WPRE), adipocyte P2 enhancer, or minute virus of mice (MVM) intron (see Domenger and Grimm, *Human Molecular Genetics*, 28(R1): R3-R14 (October 2019)).

Alternatively, the methods can include delivering an RGN and guide RNA together, e.g., as a complex. For example, the RGN and gRNA can be overexpressed in a host cell and purified, then complexed with the guide RNA (e.g., in a test tube) to form a ribonucleoprotein (RNP), and delivered to cells. In some embodiments, the RGN can be expressed in and purified from bacteria through the use of bacterial expression plasmids. For example, His-tagged deaminase fusion protein can be expressed in bacterial cells and then purified using nickel affinity chromatography. The use of RNPs circumvents the necessity of delivering plasmid DNAs encoding the nuclease or the guide, or encoding the nuclease as an mRNA. RNP delivery may also improve specificity, presumably because the half-life of the RNP is shorter and there's no persistent expression of the nuclease and guide (as you'd get from a plasmid). The RNPs can be delivered to the cells in vivo or in vitro, e.g., using lipid-mediated transfection or electroporation. See, e.g., Liang et al. "Rapid and highly efficient mammalian cell engineering via Cas9 protein transfection." *Journal of biotechnology* 208 (2015): 44-53; Zuris, John A., et al. "Cationic lipid-mediated delivery of proteins enables efficient protein-based genome editing in vitro and in vivo." *Nature biotechnology* 33.1 (2015): 73-80; Kim et al. "Highly efficient RNA-guided genome editing in human cells via delivery of purified Cas9 ribonucleoproteins." Genome research 24.6 (2014): 1012-1019. Other engineered nuclease proteins, e.g., Meganucleases, TALEs, or ZFNs, can also be produced and delivered in this manner.

II. Methods of Treatment

Provided herein are methods of treating subjects (e.g., mammalian subjects, e.g., human or non-human veterinary subjects) who are overweight (BMI 25-29.9) or who have obesity (BMI>30).

Methods described herein also encompass treating subjects having a condition associated with an elevated BMI (e.g., BMI>25) including, but are not limited to, metabolic syndrome, prediabetes, type 2 diabetes, lipodystrophy, cardiovascular disease (e.g., coronary artery disease (CAD), atherosclerosis, stroke), nephropathy, neuropathy, dyslipidemia, diabetic foot syndrome (DFS), leg or foot ulcers, impaired wound healing, fatty liver disease (e.g., nonalcoholic fatty liver disease (NAFLD), nonalcoholic steatohepatitis (NASH)), or a combination thereof. Lipodystrophy includes lipodystrophies associated with genetic mutations (e.g., congenital generalized lipodystrophy (CGL), familial partial lipodystrophy (FPLD)) and/or viral infections (e.g., HIV infection).

In some instances, a subject who is not overweight or obese (e.g., a subject having a BMI<25) can have a condition associated with an elevated BMI. Accordingly, methods described herein encompass treating a subject who is not overweight or obese and who has a condition associated with an elevated BMI. For example, methods described herein include treating a subject who is not overweight or obese (e.g., BMI<24.9) and who has lipodystropy.

Suitable subjects can be identified by one of skill in the art. For example, a subject who is overweight or obese and/or who has a condition associated with an elevated BMI can be identified by routine medical examination, e.g., laboratory tests, organ functional tests, physical examination, genetic testing, metabolic profiling, and combinations thereof.

Methods described herein can be used to treat, or to reduce the risk of developing or worsening, of any of the conditions described herein including conditions associated with being overweight or obese such as metabolic syndrome and type 2 diabetes. The methods can result in improvement in one or more symptoms or clinical parameters of the condition, e.g., reduction in weight, reduction in insulin resistance, improved glucose tolerance (routinely measured by the fasting glucose test), reduction in need for insulin, and/or a reduction in symptoms, severity, or risk of developing cardiovascular disease, diabetic retinopathy, diabetic kidney failure, diabetic neuropathy, periodontal disease, and non-alcoholic fatty liver disease. In some embodiments, the subject has prediabetes, i.e., a precursor stage prior to the onset of diabetes mellitus in which not all of the symptoms required to diagnose diabetes are present, but blood sugar is abnormally high. Impaired fasting glycemia and impaired glucose tolerance are two forms of prediabetes that are similar in clinical definition (glucose levels that too high for their context) but are physiologically distinct (Disse, E; et al. (2013), *Diabetes Metab.*, 39 (2): 132-138). Insulin resistance, the insulin resistance syndrome (metabolic syndrome or syndrome X), and prediabetes are closely related to one another and have overlapping aspects.

Methods described herein include administering an effective amount of engineered adipocytes, i.e., adipocytes that have been treated using a method described herein to disrupt the expression of Nrip1. Methods known in the art can be used to administer the engineered adipocytes, e.g., as described in Tran and Kahn, *Nature Reviews Endocrinology* 6, 195-213 (2010); Yoshimura et al., *Breast J.* 16(2):169-75 (2010); Yoshimura et al., *Dermatol Surg.* 34(9):1178-85 (2008); and Yoshimura et al., *Regen Med.* 4(2):265-73 (2009). For example, the engineered adipocytes can be administered by subcutaneous injection, site-specific transplantation, injection into a specific tissue, or intravenous injection, e.g., wherein the ASCs home to the injured tissue (see, e.g., Lee et al., *J. Orthop. Res.* 27, 295-302 (2009); Kim et al., *Int. J. Cardiol.* 146(3):371-8 (2011)). In some examples, the engineered adipocytes can be administered an adenylate cyclase activator (e.g., forskolin, catecholamine).

Any of the engineered adipocytes described herein can be administered alone or in combination with another therapy. For example, when a subject has type 2 diabetes, the subject can be treated with engineered adipocytes or with engineered adipocytes and insulin therapy.

Methods described herein encompass administering a single dose or multiple doses of engineered adipocytes to a subject. For example, a subject can be administered a single dose of engineered adipocytes. Alternatively, or in addition to, a subject can be administered multiple doses of engineered adipocytes (e.g., 2, 3, 4, 5, 6, 7, 8 or more doses).

For clinical use, engineered adipocytes are preferably autologous, i.e., obtained from the same individual to whom the engineered cells are to be administered. Alternatively, or in addition to, engineered adipocytes for clinical use are allogeneic, i.e., obtained from a different individual than the individual to whom the engineered cells are to be administered. In some examples, when administering allogeneic engineered adipocytes, methods described herein can further comprise administering an immunosuppressive agent to the subject.

EXAMPLES

In order that the invention described may be more fully understood, the following examples are set forth. The examples described in this application are offered to illustrate the methods and compositions provided herein and are not to be construed in any way as limiting their scope.

Materials and Methods

The following materials and methods were used in the Examples set forth herein.

Animals and Diets

All animal work was approved by the University of Massachusetts Medical School Institutional Animal Care Use Committee with adherence to the laws of the United States and regulations of the Department of Agriculture. Mice were housed at 20-22° C. on a 12-hour light/12-hour dark cycle with ad libitum access to food and water. C57BL/6J male mice were purchased from Jackson Laboratory for implant studies. C57BL/6J (Jackson Laboratory) male mice were bred for primary preadipocyte cultures. Briefly, 10-week old male mice arrived and were allowed to acclimate for a week prior to any procedures. Baseline glucose tolerance tests were performed three days before implanting edited cells. Mice were implanted with edited primary mouse adipocytes at 11 weeks of age by anesthetizing prior to the implantation procedure using an anesthesia vaporizer chamber with a continuous flow 500 cc/minute of $O_2$ with 3% (v/v) isoflurane for induction and 1.5% (v/v) for maintenance. After the cell injections, animals were allowed to wake up and were placed back in clean cages. Mice were maintained on a chow diet for the first 6 weeks, followed by a 60 kcal % fat diet (Research Diets, D12492i) for the remainder of the experiment from 6 to 16 weeks post implant. Glucose tolerance tests were performed after 16-hour overnight fasting with intraperitoneal injection of 1 g/kg D(+) glucose. Insulin tolerance tests were performed with 0.75 IU/kg after 6-hour daytime fasting. Male NOD.Cg-Prkdc$^{scid}$ Il2rg$^{tm1Wjl}$/SzJ (denoted as NSG) mice were kindly donated by Taconic Biosciences, Inc. At 11 weeks of age NSG mice received implants with edited primary human adipocytes. Mice were maintained on a chow diet for the first 10 weeks, followed by placing them at thermoneutral environment with a 60 kcal % high fat diet (Research Diets, D12492i) for the remainder of the experiment from 10 to 15 weeks post implant. Housing under thermoneutrality was achieved by placing the NSG mice at 30° C. on a 12-hour light/12-hour dark cycle. Glucose tolerance tests with NSG mice were performed after a 16-hour fast with intraperitoneal injection 2 g/kg D(+) glucose. Whole blood was drawn and placed in EDTA-containing tubes from living mice with submandibular vein punctures under anesthesia as described above and in the end of the study with cardiac puncture. Plasma was extracted with centrifugation of whole blood for 15 minutes at 300 rcf at 4° C.

Human Subjects

Abdominal subcutaneous adipose tissue was obtained from discarded tissue following panniculectomy. All subjects consented to the use of tissue and all procedures were approved by the University of Massachusetts Institutional Review Board.

Primary Mouse Preadipocyte Isolation, Culture and Differentiation to Primary Adipocytes 2 to 3 week old C57BL/6J male mice were euthanized and inguinal fat tissue was harvested (including lymph node) and placed in HBSS buffer (Gibco #14025) plus 3% (w/v) bovine serum albumin (BSA) (American Bioanalytical). The protocol was carried out as described previously[34] with the following modifications: cells were incubated in 2 mg/mL collagenase (Sigma #C6885) in HBSS BSA 3% (w/v) for 20 minutes to digest the tissue. Cells were cultured to sub-confluence in complete media containing DMEM/F12 media (Gibco #11330), 1% (v/v) Penicillin/streptomycin, 10% (v/v) Fetal bovine serum (FBS) (Atlanta Biologicals #S11550), 100 µg/mL Normocin (Invivogen #Ant-nr-1) at which time they were transfected with RNPs by electroporation and re-plated. Adipocyte differentiation was induced in the edited cells 24 hours post confluence previously described[28]. Briefly, adipogenic differentiation was initiated on day 0 with the addition of 5 µg/mL insulin, 1 µM dexamethasone, 0.5 mM 3-isobutyl-1-methylxanthine, 60 µM indomethacin and 1 µM rosiglitazone in the complete media. On day 2 (48 hours later), the media was changed with complete media enriched with 5 µg/mL insulin and 1 µM rosiglitazone and on day 4 the media was changed with complete media enriched with 5 µg/mL insulin. By day six after differentiation the cells are considered fully differentiated and may continue to be cultured in complete media.

Primary Human Preadipocyte Isolation, Culture and Differentiation to Primary Adipocytes Explants from human abdominal subcutaneous adipose tissue from individuals undergoing panniculectomy surgery were embedded in matrigel and cultured as previously described[23,46]. This method was demonstrated to provide a large expansion of adipocyte progenitors from the growing vascular-like projections out of small pieces of human adipose tissue[23]. Human adipocyte progenitors were transfected with RNPs by electroporation and plated at a density greater than 70% confluence to allow for further expansion. Cells were grown to confluence, then adipogenic differentiation media was added to induce adipogenesis[23,46]. On day 10 post differentiation, cells were harvested for implantation in NSG mice by treating with 0.5 mg/mL collagenase in 1× Trypsin to detach from culture plates.

Transfection of Primary Preadipocytes (Mouse and Human) with RNPs

For ribonucleoprotein (RNP) transfection, we used the Neon Transfection System 100 µL Kit (ThermoFisher, #MPK10096) and we prepared a mix consisting unless otherwise specified of sgRNA 4 µM (Synthego or IDT DNA) purified SpyCas9 protein 3 µM (PNA Bio, #CP02 or 3×NLS-SpCas9[47] (prepared by the Scot Wolfe laboratory) in Buffer R provided in the Neon Transfection System Kit. The cells were resuspended in Resuspension Buffer R for a final number of 0.5-6×10$^6$ cells per electroporation. For delivering the RNP complex into primary pre-adipocytes the electroporation parameters used were voltage 1350 V, width of pulse 30 ms; number of pulses 1 unless otherwise specified. The electroporated cells were placed in complete media immediately following transfection, expanded, grown to confluence and differentiated into mature adipocytes for downstream applications. We found these methods improved the viability of preadipocytes and adipocytes and their ability to differentiate over methods reported while our manuscript was in preparation[48]. The sequences for the sgRNAs used are provided in Table 1.

Implantation of Primary Mouse and Human Adipocytes

Primary mouse and human mature adipocytes on day 6 and 10 post differentiation respectively were washed twice with 1×PBS. 0.5 mg/mL collagenase in 1×trypsin was used to dissociate the cells from the plate. The detached cells are pelleted at 300 rcf for 10 minutes at room temperature. The cells were washed with 1×PBS, pelleted, and the PBS was removed. Cell pellets were kept on ice for a brief time until implantation. Each mouse adipocyte pellet deriving from 1×150 mm fully confluent plate was mixed with matrigel (Corning® Matrigel® Growth Factor Reduced Basement Membrane Matrix, Phenol Red-free, LDEV-free #356231) up to a total volume of 500 µL on ice and the cell and matrigel suspension (500±20 µL) was drawn into a 1 mL syringe without the needle. The cell and Matrigel mixture was injected into the anesthetized mouse recipient with a 20G needle by tenting the subcutaneous subscapular area, inserting the needle into the tented space and injecting at a slow but continuous rate to avoid cell rupture and solidification of the matrigel. The injection site was pinched gently for 1 minute to allow the implant to solidify, followed by withdrawing the needle with a twisting motion. Each C57BL/6J mouse recipient was injected with 2×150 mm plates of fully confluent murine adipocytes split into two bilateral injections in the subscapular area. Each NSG mouse recipient received 1×150 mm plate split into two 500 µL bilateral subcutaneous injections in the dorsal area as described above.

DNA Harvest from Cells and Tissue

At two distinct time-points, 72 hours following transfection and after primary adipocyte differentiation between day 6-10 post differentiation, genomic DNA was isolated from the transfected cells using DNA QuickExtract™ Buffer (Lucigen) in adherence to the manufacturer's instructions.

Indel Analysis by TIDE and ICE

Genomic DNA was PCR amplified for downstream analysis using locus specific primers designed with MacVector 17.0 and purchased from IDT DNA and Genewiz, spanning the region 800 bp around the expected DSB. For the PCR, Kappa 2× Hot start HiFi mix was used and PCR products were purified using the QIAgen DNA purification kit following the manufacturer's instructions and submitted to Genewiz for Sanger Sequencing. Sanger sequencing trace data were analyzed with TIDE and ICE webtools (shinyapps.datacurators.n1/tide/; ice.synthego.com/#/) that decipher the composition of indels created at the sites of DSBs[49,50].

RNA Isolation

Transfected cells were harvested for RNA between day 6-10, post-differentiation depending on the experiment by removing media and washing once with 1×PBS, and adding Trizol reagent to lyse the cells. The protocol for RNA isolation was performed according to manufacturer's instruction with the following modifications: 1 μL of Glycol blue (Invitrogen #AM9516) was added to the isopropanol to precipitate the RNA and was either stored overnight at −20° C. or placed on dry ice for 2 hours. The isolated RNA was resuspended in RNase free water, then treated with recombinant DNase I (DNA-free DNA removal kit, Ambion) according to the manufacturer's instructions. RNA concentrations were determined by Nanodrop 2000.

RNA Isolation of Pulverized Tissue/Tissue Piece

Tissue was isolated from the mice and frozen in liquid N2. For RNA isolation, tissue was pulverized in liquid N2, or a piece approx. 100 mg in size was put in a 2 mL tube with screw cap and 1 mL of Trizol. Tissue was placed in the Qiagen TissueLyser and homogenized for 3 cycles of 3 minutes at 30 Hz. The Trizol and tissue lysate were placed in a new tube, and centrifuged for 10 minutes at 4° C. to separate any lipid from the homogenate. Once the homogenate is separated from the lipid, the remaining isolation is carried out according to manufacturer's instructions.

RT-PCR 0.5-1 μg of RNA was used in 20 μL reaction with Bio-Rad iScript cDNA kit according to manufacturer's protocol to synthesize cDNA. cDNA was diluted by adding 80 μL of water to the reaction and 5 μL of cDNA template was used for RT-PCR with Bio-Rad Sybr Green Mix and gene specific primers for a final concentration of 0.3 μM primers. Expression of genes was determined by comparing gene expression levels of target gene compared to housekeeping gene 36B4 and RPL4 for murine and human samples respectively. mRNA expression was analyzed with the ΔΔCT method.

Protein Isolation

Cells grown in culture dishes were washed once with 1×PBS at room temperature, followed by adding boiling 2% SDS (w/v) with 1×HALT protease inhibitors and scraping to lyse the cells. Tissue pieces were prepared for western blots by homogenizing a piece approximately 100 mg in Radio-immunoprecipitation Assay (RIPA) buffer with 1×HALT protease inhibitors in the Qiagen TissueLyser and homogenized for 3 cycles of 3 minutes at 30 Hz. Tissue and cell lysates prepared with 2% SDS (w/v) buffer or RIPA buffer were sonicated at 60% amplitude with a probe sonicator tip for 30 seconds at room temperature. In FIG. 1b, mouse cells were lysed as described above at different time-points after transfection and for timepoint 0 hours, after the electroporation the transfection mix consisting of cells and RNPs in Buffer R was centrifuged at 300 rcf. The cell pellet was lysed as described above while the supernatant (sup) was also collected for use as positive control (SpyCas9 3 μM) in the western blot. Protein concentration determination of the tissue and cell lysates was performed using a bicinchoninic acid kit (BCA Protein Assay Kit, Pierce). Cell lysates used in immunoprecipitation reaction were prepared in non-denaturing NP-40 buffer (20 mM Tris HCl pH 8.0, 137 mM NaCl, 1% (v/v) Nonident P-40 (NP_40), 2 mM EDT) containing 1× HALT protease inhibitors by washing once with 1×PBS, adding NP-40 buffer and scraping, followed by a 4° C. incubation for 30 minutes to 1 hour with gentle agitation. Cell lysates were centrifuged at 4° C. for 10 minutes at 16,100 rcf and the infranatant was collected and used. Protein concentrations were determined on the lysates using Pierce BCA Kit. Protein samples were prepared for running on 7.5-12% SDS-PAGE mini gels at a final concentration of 1 mg/mL protein, 1×Laemmli loading buffer (BioRad) with 2.5% (v/v) β-Mercaptoethanol, followed by placing in a heat block at 95° C. for 10 minutes.

Oxygen Consumption Rate Assay

Oxygen consumption assay was performed using the Cayman Oxygen Consumption Rate Assay Kit (Cayman Chemical #600800) and measured using a Tecan Saffire II. Briefly, primary pre-adipocytes (male or female) were plated in 96-well flat bottom plates after transfection with NTC- or NRIP1 sgRNA-M6-RNPs. Cells were grown to confluence, followed by differentiating as previously described. On day 7 post differentiation, oxygen consumption assays were performed. All chemicals used in the assay were diluted in OCR media consisting of DMEM/F12 media (Gibco #11330), 10% (v/v) Fetal bovine serum (FBS) (Atlanta Biologicals #S11550), 2% (w/v) Fatty Acid Free BSA (Sigma #8806) and prepared as batch-working solutions to reduce pipetting error. The contribution of mitochondrial oxygen consumption was determined by subtracting values obtained in the presence of antimycin A (1:29 final dilution, Cayman Chemical kit). Oligomycin was used at 2.5 μM final concentration, FCCP at 5 μM and 10 μM L-(−)-Norepinephrine (+)-bitartrate salt (Sigma #N5785) was added where indicated. Each well was covered with 100 μL of mineral oil to seal the wells from ambient oxygen. Kinetic measurements were carried out with the fluorescent excitation/emission wavelengths of 380/650 nm, and readings taken every 2 minutes for 120 minutes. This assay was performed in both male and female primary adipocytes multiple times and the data shown here is representative of the assays performed. The final data shown is the average of 3 technical replicates at each time point with the corresponding average 3 technical replicates of the antimycin A sample subtracted to reflect only mitochondrial respiration values.

Triglyceride Assay

For the liver triglyceride assay, we used the Triglyceride Colorimetric assay kit (Cayman Chemical, #10010303). The lysate was prepared by mixing 50 mg of pulverized whole liver with 1.5 mL of the NP-40 lysis buffer and homogenized in the Qiagen TissueLyser with 3 cycles 3 minutes at 30 Hz. The assay ran according to manufacturer instructions with a sample dilution of 1:5.

Histology

Approximately 0.5 cm² of the implant tissue and two 0.5 cm² liver pieces from two different lobes per recipient were randomly selected and fixed, followed by processing at the UMass Medical School Morphology Core. Photos of the tissues were taken with an LEICA DM 2500 LED inverted microscope at indicated magnification. Fiji/ImageJ was used to quantify lipid content in H&E images. 4 images per section, 2 sections per liver, were projected into a single montage. The montage was converted from RGB to 8 bit, contrast enhanced, thresholded and binarized. The processed montage was reconverted into individual images and lipid droplets quantified for each image using the particle analysis function (number, size, % of area covered).

Western Blotting and Immunoprecipitation

Protein lysates were run on 7.5 and 12% SDS-PAGE or Mini-Protean TGX stain-free pre-cast protein gels, followed by transferring the proteins to Nitrocellulose. Unless otherwise stated, a total of 20 μg of protein lysate was loaded per well. Nitrocellulose membranes were blocked using 5% (w/v) Non-fat milk in Tris buffered saline with 0.1% (v/v) Tween-20 (TBST) for 1 hour at room temperature. Primary antibody incubations were carried out in 5% (w/v) BSA in TBST at the following antibody concentrations: UCP1-Abcam #10983, 1:700; Rip140-Millipore #MABS1917, 1:1000, Tubulin-Sigma #T5168, 1:4000; GAPDH-Cell Signaling #21185, 1:1000; SpyCas9-Cell Signaling #19526S 1:5000, OXPHOS Abcam #110413, 1:1000. Blots and primary antibodies were incubated overnight with a roller mixer at 4° C. Membranes were washed with TBST prior to secondary antibody incubations. HRP-conjugated secondary antibodies were diluted with 5% BSA (w/v) in TBST at 1:5,000-10,000 for 45 minutes at room temperature with constant shaking. Membranes were washed in TBST, followed by incubating with Perkin Elmer Western Lightning Enhance ECL. The Bio-Rad Chemi-Doc XRS was used to image the chemiluminescence and quantifications were performed using the system software, or Image J. Immunoprecipitation was performed with NP-40/Halt protein lysates. Briefly, 250 μg of protein lysates were pre-cleared using 50:50 Protein-A Sepharose/NP-40 buffer/1× HALT protease inhibitors for 2 hours at 4° C. with end over end mixing. After 2 hours, the lysate/Protein A Sepharose was centrifuged for 5 seconds to pellet the Sepharose, and the lysate was transferred to a new tube. 5 μg of Antibody (Rabbit Non-Immune IgG, Millipore #12-370, or Rabbit anti-Nrip1, Abcam #Ab42126) was added to the lysates and they were incubated overnight at 4° C. with end over end mixing. Antibody/antigen was pulled down by adding 50:50 Protein A Sepharose/NP-40 buffer/1× HALT protease inhibitors for an additional 2 hours at 4° C. with end over end mixing. Protein/Antibody/Protein A Sepharose complexes were washed by centrifuging briefly, removing the supernatant and washing the pellet with NP-40 buffer containing protease inhibitors. The captured proteins were eluted from the Sepharose by adding 40 μL of 1×Laemmli buffer containing 2.5% (v/v) β-Mercaptoethanol, vortexing the Sepharose mixture, followed by boiling at 95° C. for 10 minutes. All eluted proteins were run on the gel, transferred to nitrocellulose, and immunoblotted as described above.

RNA-Sequencing

RNA was isolated on day 6 post differentiation and treated with DNase treatment as described, and 2 μg of total RNA was submitted to GENEWIZ for standard RNA sequencing (Illumina HiSeq). The data were acquired demultiplexed in the form of FASTQ files. Alignment and quantification of gene expression levels were performed using the Dolphin-Next RNA-seq pipeline (revision 3)[51]. Parameters for the pipeline were set to remove Illumina 3' adapter sequences using trimmomatic software (v0.39) with seed mismatches set to 2, a palindrome clip threshold of 30 and a simple clip threshold of 5[52]. The DolphinNext pipeline used RSEM (v1.3.1) to align RNA-Seq reads to a mouse reference transcript (using the RSEM reference STAR and and Bowtie genomes) to estimate gene expression levels[53]. DESeq2 software (v 1.28.1) was then used on these expression levels to find differentially expressed (DE) genes between two groups of samples. We set the parameters test="LRT" (Likelihood Ratio Test), fitType="parametric", betaPrior=FALSE, and reduced=~1 (to compare to the control group). Alpha (padj) was set to 0.1 and a minFC=1.3 was specified'. Once DE genes were found, enriched pathways were identified using the biomaRt (v 2.44.2) enrichGO routine. Parameters for this routine were set to orgDb="org.Mm.eg.db", pAdjustMethod="fdr", pvalueCutoff=0.05, ont="BP", and minGSSize=10[55]. The "universe" was set to all the genes found by RSEM. Similar pathways were combined using clusterProfiler's (v 3.16.1) simplify( ) function. The top 10 pathways were then displayed using the dotplot routine from the enrichplot package (version 1.8.1, loaded by clusterProfiler)[56]. Pathways where further culled or merged based on pathway names specified manually. Heatmaps of selected genes were generated using the normalized (for sample depth) values returned by the DESeq2 counts(ddsRES, normalized=TRUE) function. Prior to display values were standardized (each gene had its mean expression level subtracted and was then divided by the gene's standard deviation). The gplots package (v 3.1.0) was then used, via the heatmap.2 function, to display the heatmap. Custom software was written to combine lists of genes from many pathways to create the gene list used in the "stacked pathway heatmap", which was then displayed using heatmap.2. Principal component analysis was applied to the normalized data (DESeq2 getNormalizedMatrix( ) with method="MRN"). The debrowser package's (v 1.16.3) run_pca( ) routine was used to calculate the principal components; it centers and scales the data prior to calculating the principal components[57-59].

Human Adiponectin

Human adiponectin was measured in the plasma of NSG mice was measured using a human-specific adiponectin ELISA from Invitrogen (KHP0041).

Plasmid Construction

The pCS2-Dest plasmid with CMV promoter expressing SpyCas9 (Addgene #69220), and sgRNA expressing plasmid (Addgene #52628) were a gift from Dr. Scot Wolfe lab. To clone NRIP1 targeting and non-targeting sgRNAs, oligo spacers with BfuAI overhangs (purchased from IDT) were annealed and cloned into the BfuAI-digested sgRNA plasmid. Lonza pmaxGFP LOT 2-00096 was used to test transfection of these plasmids in various concentrations to determine the efficient dosage range (0.5-1.5 μg) and the electroporation conditions (1350 V, 30 ms, 1 pulse) for the delivery and GFP expression was evaluated with EVOS FL fluorescent microscope (Thermo Fisher Scientific).

Plasma Cytokine and Chemokine Analysis

Whole blood was collected from the mouse recipients with cardiac puncture at the end of the studies and placed in EDTA containing tubes. The plasma was collected after a 15 minute centrifugation at 2,000 rcf and 4° C. Multiplex analysis of plasma cytokines and chemokines was performed by the Luminex system. For positive controls, 4 C57BL6/J mice age and gender-matched to the recipients with body weights ranging from 34 to 40 g were injected with 1 µg LPS diluted in PBS and their plasma was collected as described above 2 hours after injections. For the data analysis, the measurements found to be below the detectable cut-off were considered as 0 as a lowest value of 0.4 pg/mL was measured.

GUIDE-seq

In order to obtain results that correspond to our CRISPR delivery method and cell-type, we modified the GUIDE-seq transfection protocol using our standard RNP concentration and electroporation method combined with the dsODN in various amounts (7.5, 10, 20, 30, 50, 80, 100 pmols) to achieve optimal on-target editing and dsODN integration. Three days after transfection, genomic DNA was isolated using the DNeasy Blood and Tissue kit (Qiagen) according to manufacturer's instructions. GUIDE-seq libraries were prepared using the custom oligos and adapters previously described described'. The barcoded libraries were sequenced on a MiniSeq platform in a paired end "147|8|16|147" run. Sequencer output was demultiplexed, trimmed and aligned according to a published workflow[60]. Positive- and negative-strand BAM files, along with a UMI reference, were processed as GUIDEseq[61] inputs with parameters allowing for an NGG PAM and 10 or fewer mismatches.

Amplicon Sequencing Analysis of On- and Off-Target Editing

Genomic DNA was isolated from both human and mouse NTC or NRIP1KO adipocytes after day 6 post differentiation n [NTC]=3; n [NRIP1KO]=3 per amplicon. Illumina amplicon sequencing library was prepared using a two-step PCR protocol. During PCR1, regions of interest (around 290 bp) were amplified as follows: 98° C. for 2 minutes, 24 cycles of 98° C. for 15 sec—64° C. for 20 sec—72° C. for 15 sec, and 72° C. for 5 min, in a reaction mix of 50 ng genomic DNA, 10 µM forward and reverse primers that contain Illumina adapter sequences 1 µL each, 12.5 µL NEBNext UltraII Q5 Master Mix, and water to bring the total volume to 25 µL. Then, PCR2 was performed as follows: 98° C. for 2 minutes, 10 cycles of 98° C. for 15 sec—64° C. for 20 sec—72° C. for 15 sec, and 72° C. for 5 min, in a reaction mix of 5 µL of total PCR1 product, 10 µM forward and reverse primers that contain unique barcode sequences 2 µL each, 25 µL NEBNext UltraII Q5 Master Mix, and water to bring the total volume to 50 µt. PCR2 products were first purified (Zymo PCR purification kit), visualized using 1.5% agarose gel electrophoresis, and pooled together for similar amounts based on the band intensities. Pooled PCR2 products ran on 2% agarose gel electrophoresis and cut for desired bands (around 400 bp) for gel extraction (Zymoclean DNA Gel recovery kit). Concentration of the final purified library was determined using Qubit (High Sensitivity DNA assay). The integrity of the library was confirmed by Agilent Tapestation using Agilent High Sensitivity D1000 ScreenTape kit. The library was sequenced on an Illumina Miniseq platform according to the manufacturer's instructions using Miniseq Mid Output Kit (300-cycles) in a paired end "151|6|8|151" run. CRISPResso2 was used to align the reads and quantify the editing[62].

Statistical Analysis

All comparisons between two groups were performed with student unpaired two-tailed T-Test with the following demonstration ofp values in the panels: *p<0.05, p<0.01, * p<0.001. In data that Gaussian distribution cannot be assumed, normalization to equal standard distributions preceded the statistical analysis. All p values, t values and degrees of freedom are reported in the raw data file. All comparisons between more than two groups (FIG. 4, Extended data FIG. 3k) were performed with one-way ANOVA and multiple comparison's in those were performed with Dunnett's multiple comparisons test. P value, F value are provided in the raw data file. Statistics used in the oxygen consumption analysis (FIGS. 2e-2f and FIGS. 2h-2i) were One-way ANOVA with Sidak's multiple comparison test and two-way ANOVA for the 40 minute timepoint summary (FIGS. 2g-2h) with Sidak's multiple comparison test.

Additional Online Tools and Software

For the mapping of exons on the Nrip1 gene we used IGV_2.5.3. For the Design of sgRNAs we used a combination of the Broad Institute sgRNA designer, CHOPCHOP and the online sgRNA checkers by Synthego and IDT. For the design of genomic DNA primers we used MacVector 17.0. For the alignment of the Sanger Sequencing traces and the human and mouse coding region we used SnapGene Viewer 5.1.6 and NCBI nucleotide blast. For the design of RT-PCR primers we used Primer Bank (pga.mgh.harvard.edu/primerbank/). For the browning probability potential, the unnormalized mapped read counts were applied in the ProFAT online tool[37]. Off-target diagrams were generated from GUIDEseq output using a freely available visualization tool (mismatch.netlify.app). For the data graphing, we used Prism GraphPad 9 unless otherwise specified.

Example 1: SpyCas9/sgRNA RNPs for Ex Vivo Gene Editing

In order to define optimal sites for disruption of the Nrip1 gene in mouse preadipocytes, we designed 7 sgRNAs targeting various locations of the mouse genomic DNA in exon 4, which contains the entire open reading frame (FIG. 1a). A key aspect of our strategy in targeting the Nrip1 gene was to employ methods that would ablate its expression in adipocytes but not cause immune responses upon implantation of the cells. CRISPR-based methods eliciting continuous expression of Cas9/sgRNA to modify adipocytes that function in vivo have been reported[30,31], but they expose recipients to Cas9 and delivery agents that cause immune responses[32]. Direct administration of Cas9/sgRNA complexes in mice have not been adipocyte-specific and could cause undesirable effects in other tissues[30,33]. Ribonucleoprotein complexes of SpyCas9/sgRNA are desirable vehicles for such modifications since they are rapidly degraded following DNA disruption[34]. A previous attempt at delivery of such CRISPR-based complexes to adipocytes were suboptimal as efficiencies of delivery of RNPs to these cells was only modest[28]. We overcame these deficiencies by disrupting Nrip1 in mouse preadipocytes with ribonucleoprotein (RNP) complexes of Cas9 and sgRNA by modifying electroporation methods' described for other cell types (FIGS. 8a-8g) and confirmed Cas9 protein is rapidly degraded following indel formation in preadipocytes using RNPs containing sgRNA M6 (FIG. 1b). Electroporation conditions were developed to optimize the efficiency of Nrip1 gene targeting in mouse preadipocytes by Cas9/sgRNA RNPs without perturbing their differentiation into adipocytes (FIG. 1d and FIGS. 8a-8g). Thus, the efficiencies of indel formation by the 7 different sgRNAs against various regions of Nrip1 gene exon 4 (FIG. 1a) were uniformly sustained in the 90% range in preadipocytes and upon their differentiation into adipocytes (FIG. 1d). Indels were quantified by Sanger sequencing data analysis of PCR fragments spanning the upstream and downstream double stranded breaks of the Nrip1 genomic DNA (FIG. 1c and FIG. 1e) with little change in the total Nrip1 mRNAs (FIG. 1f). High frequencies of frameshift mutations in Nrip1 by all 7 sgRNAs were observed and similar indels were found in the corresponding Nrip1 mRNA species, as exemplified by sgRNA M3 and M4 (FIG. 1e and FIGS. 9a-9b).

While the mRNA of Nrip1 was equally abundant in all groups, indicating little or no increased degradation due to disruption (FIG. 1f), surprisingly, not all of the sgRNAs were effective in eliciting loss of the NRIP1 protein (FIG. 1g). Consistent with these data, thermogenic responses to the various sgRNAs as reflected by elevated expression of UCP1 mRNA (FIG. 1h) and protein (FIG. 1i) correlated with the loss of native full length NRIP1 protein. Taken together, these data show that sgRNAs targeting the regions of Nrip1 DNA that encode the N-terminal region of the NRIP1 protein are not effective in eliminating synthesis of functional NRIP1 protein. Most likely, additional transcription or translation start sites beyond these target sites are functional under these conditions (FIG. 9c). Thus, sgRNAs that are optimal for inducing thermogenic genes must be identified by such screening methods.

Example 2: Thermogenic Activity in NRIP1KO Adipocytes from Male and Female Mice

Experiments as described in Example 1 were performed on preadipocytes from both male and female mice to determine effects of Nrip1 disruption on adipocyte thermogenesis with equally high editing efficiency. Upregulation of Ucp1 mRNA was over 100 fold in Nrip1 deficient adipocytes derived from both male and female mice (FIG. 2a), and the fold changes in expression of many other genes were also nearly identical in these genetically modified adipocytes from the different sexes (FIG. 2b). This similarity in response to Nrip1 disruption in male versus female mice was also observed in the upregulation of UCP1 protein expression (FIG. 2c).

Figure 2I:
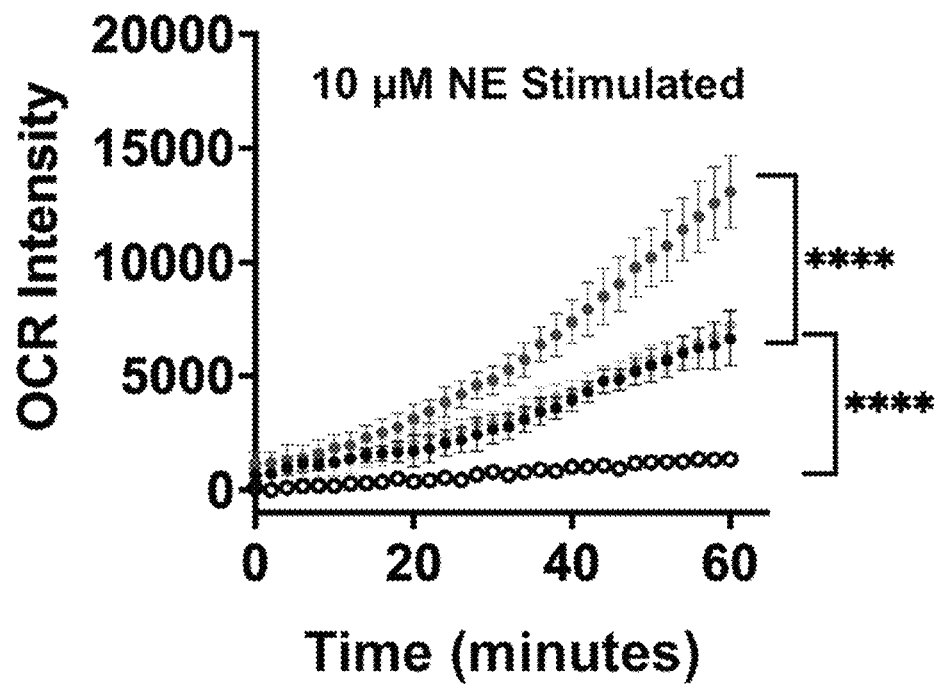
Figure 2J:
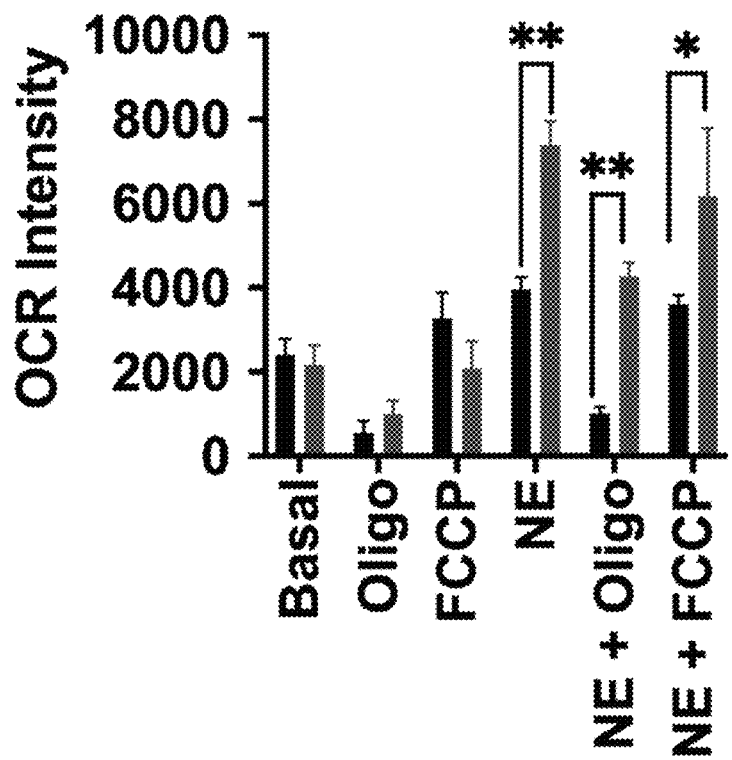

In addition to UCP1 upregulation, NRIP1KO adipocytes also exhibited higher expression of mitochondrial respiratory chain components UQCRC2 of complex III and SDHB of complex II (FIG. 2d). Together with the increased UCP1 expression, the upregulation of these and many other known metabolic enzymes combine to dramatically affect the respiration rates and characteristics of NRIP1KO adipocytes. Confirming this expectation, we found that while there is little change in oxygen consumption between control and NRIP1KO adipocytes under basal (FIG. 2e), unstimulated conditions, norepinephrine (NE) much more robustly increased NRIP1KO adipocyte respiration (FIG. 2f) due to its ability to activate UCP1-mediated uncoupling of mitochondria. This concept was verified upon addition of oligomycin, an inhibitor of coupled but not uncoupled respiration, which was much less effective in inhibiting oxygen consumption in NE stimulated NRIP1KO adipocytes compared to its marked suppression of NE stimulated control adipocyte respiration (FIGS. 2f-2g). These data obtained with adipocytes derived from male mice were similar to the results observed with adipocytes from female mice (FIGS. 2h-2j). Altogether, the data in FIGS. 2a-2j demonstrate that NRIP1 deficiency has similar effects to increase uncoupling and thermogenic properties of mitochondria from female and male adipocytes.

Example 3: Implantation of CRISPR-modfied Mouse Adipocytes

To test the ability of NRIP1-deficient adipocytes to improve metabolism in mice, large numbers of primary preadipocytes obtained from 2-3 week old mice were electroporated with RNPs consisting of either SpyCas9/non-targeting control (NTC) sgRNA or SpyCas9/sgRNA-M6 complexes (NRIP1KO), and then differentiated into adipocytes and implanted into wild type mice. The implanted mice were kept on normal diet for 6 weeks during the development of adipose tissue depots from the injected adipocytes, then placed on a high fat diet (HFD) regimen to enhance weight gain (FIG. 3a). Adipocytes treated with Cas9/sgRNA-M6 displayed upregulation of Ucp1 and other genes highly expressed in brown adipocytes (e.g., Cidea) prior to transplantation (FIG. 10a). A transient decrease in overall body weights were detected between mice implanted with RNPs containing the Cas9/sgRNA-M6 versus the Cas9/NTC-sgRNA group, but by 9 weeks of HFD no significant difference was observed (FIG. 3b). Nonetheless, implantation of NRIP1KO adipocytes prevented the increase in fasting blood glucose concentration due to HFD that occurs in the NTC adipocyte-implanted mice (FIG. 3c). Glucose tolerance was also significantly improved by implantation of NRIP1KO adipocytes (FIGS. 3d-3e). The implanted adipose tissue depots retained their elevated expression of UCP1 16 weeks after implantation, at which time they were excised for analysis (FIG. 4e). The livers and inguinal white adipose tissues (iWAT) from the Cas9/sgRNA-M6 group of mice had lower weights (FIG. 3f) and lower iWAT to body weight ratios (FIG. 10c), revealing a strong systemic effect.

Livers of the NRIP1 deficient adipocyte-implanted mice were less pale (FIG. 3g), were smaller as assessed by lower liver to body weight ratios (FIG. 3h) and displayed lower expression of genes associated with free fatty acid uptake (Cd36) and with inflammation (Mcp1, Tnfα, Ill1β (FIG. 3i) compared to mice implanted with control adipocytes. Lipid droplets in the livers of mice with implants of Cas9/sgRNA-M6-treated adipocytes (FIG. 3j) were greatly decreased as assessed by quantification of lipid droplet area (FIG. 3k), number and size (FIGS. 10j-10k) as well as liver triglyceride determination (FIG. 3l). The decrease in hepatic lipid accumulation and inflammation in response to implantation of the NRIP1 depleted adipocytes suggests that this therapeutic approach might mitigate these T2D co-morbidities in humans[36].

Consistent with our finding that Cas9 was degraded prior to implantation of the engineered cells (FIG. 1b), the recipient mice had no signs of disease or distress. The excised implants had no macroscopic signs of inflammation or necrotic tissue and the Mcp1 gene which signifies an inflammatory response was not upregulated in NTC or NRIP1KO implants compared to the endogenous iWAT tissue (FIG. 10i). Additional assessment of potential inflammatory responses showed no difference in plasma levels of IL-1β, IL-6, IL-10, MCP-1 or TNFα in the NTC or NRIP1KO mice compared to untreated control mice, while LPS treated mice serving as positive controls displayed greatly increased levels of these factors (FIG. 10*l*).

Example 4: Gene Expression Profiles of NRIP1KO Mouse Adipocytes and Implants

To further characterize the NRIP1KO mouse adipocytes in an unbiased manner, transcriptome analysis was performed by RNA-sequencing of mouse primary mature adipocytes on day 6 of adipogenic differentiation of either non-treated control adipocytes (no electroporation or RNPs, NT) or SpyCas9+sgRNA-NTC treated adipocytes or adipocytes treated with either SpyCas9+sgRNA-M6 or SpyCas9+sgRNA-M4 that target and deplete NRIP1 protein (NRIP1KO). Principal component analysis showed a distinct clustering of the control groups and the NRIP1KO samples independent of the specific sgRNA used, indicating distinct gene expression profiling (FIG. 4*a*). Differential gene expression comparison between all the control samples and the NRIP1KO samples revealed 902 significantly upregulated genes including Ucp1, Cidea, Fabp3 and the secreted neurotrophic factor Nrg4 (FIGS. 4*b*) and 511 significantly downregulated genes. Interestingly, the top upregulated pathways upon Nrip1 disruption are related to mitochondrial respiration and fatty acid oxidation (FIG. 4*c*), while a detailed pathway analysis of the upregulated genes revealed functions including adaptive, diet-induced and cold-induced thermogenesis. In particular, 78 of the upregulated genes are associated with the cellular respiration pathway and 18 of the upregulated genes are associated with thermogenesis. In order to assess the overall thermogenic potential, the ProFAT computational tool was applied to the three groups of samples (NT, NTC, NRIP1KO), indicating>90% "brown" adipocyte type probability in the NRIP1KO cells as opposed to the NTC and NT samples that ranged from 0 to only 20% brown probability (FIG. 4*d*)[37].

In order to examine the extent to which the altered transcriptome by NRIP1KO is sustained by the end of the study, the top 15 upregulated genes with >10,000 normalized reads in all NRIP1KO adipocyte samples were selected for screening by RT-PCR in the mouse implants 16 weeks after implantation (FIG. 4*e*). All 15 genes that were screened, tended to be more highly expressed in the NRIP1KO implant samples than in the control implant tissue, with some reaching significance despite the 4-month time lapse in vivo and the potential presence of endogenous cells that had migrated into the implants (FIG. 4*e*). In agreement with the in vitro studies, the mouse NRIP1KO adipocytes possessed a "brown" profile demonstrated by increased thermogenic genes and an increase in the expression of mitochondrial respiration components that was sustained through implantation and many weeks of HFD feeding.

Example 5: Translation to Human Adipocytes

To translate these CRISPR-based methods to human adipocytes, adipocyte progenitors were obtained from small samples of excised subcutaneous adipose tissue as previously described[23]. Electroporation conditions were tested to optimize efficiency of indel formation using various sgRNAs directed against regions of the NRIP1 exon 4 at locations roughly similar to those we targeted in the mouse genomic DNA (compare FIG. 1*a* to FIG. 5*a*). Efficiencies of NRIP1 gene disruption were observed with several sgRNAs in the 90% range (FIG. 5*b*), with indel distributions very similar in preadipocytes and adipocytes (FIG. 5*c*). Electroporated, NRIP1 deficient human preadipocytes could be readily differentiated to adipocytes without apparent disruption following indel formation (FIG. 5*d*). NRIP1 mRNA was equally abundant in all conditions (FIG. 5*e*). Similar to the findings in mouse adipocytes, NRIP1 protein was not depleted when using an sgRNA targeting an upstream site in the genomic DNA, as shown with sgRNA-H1 (FIG. 5*f*). However, with sgRNA-H5, significant depletion of NRIP1 protein was observed (FIG. 5*f*) and associated with an 80-fold upregulation of UCP1 expression (FIGS. 5*g*-5*h*). Functional NRIP1 protein can still be expressed despite high efficiency indel formation in the N-terminal NRIP1 encoded region of the human NRIP1 gene, similar to what was observed with mouse (FIG. 1*g*). Interestingly, NRIP1 disruption in combination with the adenylate cyclase activator forskolin synergistically increased Ucp1 expression (FIG. 5*i*), consistent with the concept that the cAMP pathway acts independently but coordinately with NRIP1 function.

Example 6: Gene Expression Profiles of NRIP1KO Human Adipocytes

To characterize the effect of disrupting NRIP1 in human adipocytes, RNA-seq was performed on NTC or NRIP1KO human mature adipocytes on day 7 after adipogenic differentiation. Interestingly, most differentially expressed genes were found to be upregulated and only 9 genes were downregulated. In agreement with the findings in mouse adipocytes, the top ten pathways associated with upregulated genes by NRIP1KO and the majority of all cellular functions revealed by pathway analysis are related to mitochondrial respiration and fatty acid oxidation (FIGS. 6*a*-6*b*) with 16 and 9 out of the upregulated genes being associated with these pathways respectively. To calculate the thermogenic potential of the NRIP1KO human adipocytes, the ProFAT computational tool[37] was applied to the raw gene expression datasets of the two groups of samples (NTC vs NRIP1KO), indicating a much greater brown-like probability in the NRIP1KO cells (FIG. 6*c*). Many of the human genes known to be related to thermogenesis were found to be highly expressed in NRIP1KO cells, with UCP1 ranked as the most upregulated gene overall (53-fold) (FIG. 6*d*).

Example 7: Implantation of CRISPR-modified Human Adipocytes

To test the efficacy of NRIP1-depleted human adipocytes to provide metabolic benefits in obese glucose intolerant mice, immune-compromised NOD.Cg-Prkdc$^{scid}$Il2rg$^{th1Wj1}$/SzJ (NSG) mice were utilized that lack T cells, B cells and natural killer cells and accept human cell implants in the protocol depicted (FIGS. 7*a*-7*b*). NRIP1 gene disruption was about 80% with the sgRNA-H5 (FIG. 7*c*) and circulating human adiponectin (FIG. 7*d*) was the same from NTC vs sgRNA-H5 groups, indicating similar levels of adipose tissue formation. Human NRIP1KO adipocytes exhibited upregulation of UCP1 levels similar to those shown in FIGS. 5*a*-5*i* and the resulting NRIP1KO adipose tissue implants harvested from the mice 13 weeks later retained the enhanced UCP1 expression (not shown).

While no body weight difference between groups was detected on normal diet, a highly significant decrease in weight gain on the HFD was observed in mice implanted with NRIP1 disrupted adipocytes (FIG. 7*e*). Importantly, mice with control human adipocyte implants displayed significantly decreased glucose tolerance 3 weeks after starting a HFD while animals with NRIP1-depleted adipocyte implants did not (FIGS. 7f-7i). The difference in glucose tolerance between the two groups at the end of the study was highly significant (FIGS. 7h-7i). Relative liver to body weight ratios (FIG. 7j) and liver triglycerides (FIG. 7k) were also decreased when implants were performed with NRIP1 deficient adipocytes compared to control adipocytes.

Example 8: Off-Target Screen by GUIDE-seq and Amplicon NGS Sequencing in Mouse and Human Adipocytes The genome-wide, unbiased identification of DSBs enabled by sequencing (GUIDE-Seq) was used to evaluate the potential off-target editing present in the mouse and human adipocytes described above[38]. In the mouse primary preadipocytes, a total of 12 potential off-target sites were detected and ranked by number of reads and number of sgRNA mismatches in the edited cells (FIG. 11a). A total of 11 off-target sites, mOT1-11, with up to 5 sgRNA mismatches were selected to assess editing with amplicon NGS. Out of these off-target sites screened, five off-target sites were found to have >1% editing with mOT1, mOT8, mOT9, mOT10 being located in unannotated genomic regions and the rest in intronic regions (FIG. 11b). In the human progenitors, GUIDE-seq revealed zero detectable off-target sites in the edited cells compared to the NTC cells, even after transfecting the cells with higher amount of dsODN (FIGS. 11c-11d). To further validate the human GUIDE-seq results, Cas-offinder[39] was used to select a total of 5 off-target sites which were screened by amplicon NGS, revealing no off-target editing (FIGS. 11e-11f).

REFERENCES

1. Pittenger, M. F., et al. 2019. Mesenchymal stem cell perspective: cell biology to clinical progress. *NPJ Regen Med.* 2; 4:22.
2. Kean, L. S., 2018. Defining success with cellular therapeutics: the current landscape for clinical end point and toxicity analysis. *Blood.* 131(24):2630-2639.
3. Rosenberg. S. A., Restifo, N. P., 2015. Adoptive cell transfer as personalized immunotherapy for human cancer. *Science.* 348(6230):62-8.
4. Finck. A., Gill, S. I., June, C. H., 2020. Cancer immunotherapy comes of age and looks for maturity. *Nat Commun.* 11(1):3325.
5. Czech, M. P., 2017. Insulin action and resistance in obesity and type 2 diabetes. *Nat Med.* 23(7):804-814.
6. Roden, M., Shulman, G. I., 2019. The integrative biology of type 2 diabetes. *Nature.* 576(7785):51-60.
7. Petersen, M. C., Vatner, D. F., Shulman, G. I., 2017. Regulation of hepatic glucose metabolism in health and disease. *Nat Rev Endocrinol.* 13(10):572-587.
8. Kusminski, C. M., Bickel, P. E., Scherer, P. E., 2016. Targeting adipose tissue in the treatment of obesity-associated diabetes. *Nat Rev Drug Discov.* 15(9):639-660.
9. Guilherme, A., Virbasius, J. V., Puri, V., Czech, M. P., 2008. Adipocyte dysfunctions linking obesity to insulin resistance and type 2 diabetes. *Nat Rev Mol Cell Biol.* 9(5):367-377.
10. Lee, Y. S., Wollam. J., Olefsky, J. M., 2018. An Integrated View of Immunometabolism. *Cell.* 172(1-2):22-40.
11. Funcke, J. B., Scherer, P. E., 2019. Beyond adiponectin and leptin: adipose tissue-derived mediators of inter-organ communication. *J Lipid Res.* 60(10):1648-1684.
12. Kajimura, S., Spiegelman, B. M., Seale, P., 2015. Brown and Beige Fat: Physiological Roles beyond Heat Generation. *Cell Metab.* 22(4):546-559.
13. Villarroya, F., Cereijo, R., Villarroya, J., Giralt, M., 2017. Brown adipose tissue as a secretory organ. *Nat Rev Endocrinol.* 13(1):26-35.
14. Klepac, K., Georgiadi, A., Tschop, M., Herzig, S., 2019. The role of brown and beige adipose tissue in glycaemic control. *Mol Aspects Med.* 68:90-100.
15. Nedergaard, J., Cannon, B., 2010. The changed metabolic world with human brown adipose tissue: therapeutic visions. *Cell Metab.* 11(4):268-72.
16. Wu, J., et al., 2012. Beige adipocytes are a distinct type of thermogenic fat cell in mouse and human. *Cell.* 150(2):366-76.
17. Rosenwald, M., Perdikari, A., Rüilicke, T., Wolfrum, C., 2013. Bi-directional interconversion of brite and white adipocytes. *Nat Cell Biol.* 15(6):659-67.
18. Wang, GX., et al., 2014. The brown fat-enriched secreted factor Nrg4 preserves metabolic homeostasis through attenuation of hepatic lipogenesis. *Nat Med.* 12, 1436-1443.
19. Chen, Z., et al., 2017. Nrg4 promotes fuel oxidation and a healthy adipokine profile to ameliorate diet-induced metabolic disorders. *Mol Metab.* 6(8):863-872.
20. Stanford, K. I., et al., 2013. Brown adipose tissue regulates glucose homeostasis and insulin sensitivity. *Journal of Clinical Investigation.* 123(1):215-23.
21. White, J. D., Dewal, R. S., Stanford, K. I., 2019. The beneficial effects of brown adipose tissue transplantation. *Mol Aspects of Med.* 68:74-81.
22. Lynes, M. D., et al., 2017. The cold-induced lipokine 12,13-diHOME promotes fatty acid transport into brown adipose tissue. *Nature medicine.* 23, 631-637.
23. Min, S. Y., et al., 2016. Human 'brite/beige' adipocytes develop from capillary networks, and their implantation improves metabolic homeostasis in mice. *Nat Med* 22(3): 312-8.
24. Doudna, J. A., 2020. The promise and challenge of therapeutic genome editing. *Nature.* 578(7794):229-236.
25. Hille, F., et al., 2018. The Biology of CRISPR-Cas: Backward and Forward. *Cell.* 172(6):1239-1259.
26. Leonardsson, G., et al., 2004. Nuclear receptor corepressor RIP140 regulates fat accumulation. *Proc Natl Acad Sci USA.* 101(22):8437-8442.
27. Powelka, A. M., et al., 2006. Suppression of oxidative metabolism and mitochondrial biogenesis by the transcriptional corepressor RIP140 in mouse adipocytes. *J Clin Invest.* 116(1):125-136.
28. Shen, Y., et al., 2018. CRISPR-delivery particles targeting nuclear receptor-interacting protein 1 (Nrip1) in adipose cells to enhance energy expenditure. *J. Biol Chem.* 293(44):17291-17305.
29. Nautiyal, J., Christian, M., Parker, M. G., 2013. Distinct functions for RIP140 in development, inflammation, and metabolism. *Trends Endocrinol Metab.* 24(9):451-9.
30. Chung, J. Y., Ain, Q. U., Song, Y., Yong, S. B., Kim, Y. H., 2019. Targeted delivery of CRISPR interference system against Fabp4 to white adipocytes ameliorates obesity, inflammation, hepatic steatosis, and insulin resistance. *Genome Res.* 29(9):1442-1452.

31. Wang, C. H., et al., 2020. CRISPR-engineered human brown-like adipocytes prevent diet-induced obesity and ameliorate metabolic syndrome in mice. *Sci Transl Med* 12(558):eaaz8664.

32. Charlesworth, C T., et al., 2019. Identification of pre-existing adaptive immunity to Cas9 proteins in humans. *Nat Med.* 25(2):249-254.

33. Hinderer, C., et al., 2018. Severe Toxicity in Nonhuman Primates and Piglets Following High-Dose Intravenous Administration of an Adeno-Associated Virus Vector Expressing Human SMN. *Hum Gene Ther.* March; 29(3): 285-298.

34. Kim, S., Kim, D., Cho, S. W., Kim, J., Kim, J. S., 2014. Highly efficient RNA-guided genome editing in human cells via delivery of purified Cas9 ribonucleoproteins. *Genome Res.* 24(6):1012-9.

35. Huang, R. S., Shih, H. A., Lai, M. C., Chang, Y. J., Lin. S., 2020. Enhanced NK-92 Cytotoxicity by CRISPR Genome Engineering Using Cas9 Ribonucleoproteins. *Front Immunol.* 11:1008.

36. Friedman S. L., Neuschwander-Tetri, B. A., Rinella, M., Sanyal, A. J., 2018. Mechanisms of NAFLD development and therapeutic strategies. *Nat Med.* 24(7):908-922.

37. Cheng, Y., et al., 2018. Prediction of Adipose Browning Capacity by Systematic Integration of Transcriptional Profiles. *Cell Rep.* 23(10): 3112-3125.

38. Tsai, SQ., et al., 2015. GUIDE-seq enables genome-wide profiling of off-target cleavage by CRISPR-Cas nucleases. *Nat Biotechnol.* 33(2):187-197.

39. Bae, S., Park, J., Kim, J S., 2014. Cas-OFFinder: a fast and versatile algorithm that searches for potential off-target sites of Cas9 RNA-guided endonucleases. *Bioinformatics.* 30(10):1473-5.

40. Tran, T. T., Kahn, C. R. 2010. Transplantation of adipose tissue and stem cells: role in metabolism and disease. *Nat Rev Endocrinol. April;* 6(4):195-213.

41. Blumenfeld, N. R., et al. 2018. A direct tissue-grafting approach to increasing endogenous brown fat. *Sci Rep.* May 21; 8(1):7957.

42. Xiong, Y., et al. 2018. A novel brown adipocyte-enriched long non-coding RNA that is required for brown adipocyte differentiation and sufficient to drive thermogenic gene program in white adipocytes. *Biochim Biophys Acta Mol Cell Biol* April; 1863(4):409-419.

43. Ceddia, R. P, Collins, S., 2020. A compendium of G-protein-coupled receptors and cyclic nucleotide regulation of adipose tissue metabolism and energy expenditure. *Clinical Science.* 134: 473-512

44. Vakulskas, C. A., et al., 2018. A high-fidelity Cas9 mutant delivered as a ribonucleoprotein complex enables efficient gene editing in human hematopoietic stem and progenitor cells. *Nat Med* 24(8):1216-1224.

45. Kleinstiver, B. P., et al., 2016. High-fidelity CRISPR-Cas9 nucleases with no detectable genome-wide off-target effects. *Nature.* 529(7587):490-5.

46. Tran, K. V., et al., 2020. Human thermogenic adipocyte regulation by the long noncoding RNA LINC00473. *Nat Metab.* 2020; 2(5):397-412.

47. Wu, Y., et al., 2019. Highly efficient therapeutic gene editing of human hematopoietic stem cells. *Nat Med.* 25(5):776-783.

48. Kamble, P. G., et al., 2020. Proof-of-concept for CRISPR/Cas9 gene editing in human preadipocytes: Deletion of FKBP5 and PPARG and effects on adipocyte differentiation and metabolism. *Sci Rep.* 10(1):10565.

49. Hsiau, T., et al., 2019. Inference of CRISPR Edits from Sanger Trace Data., *bioRxiv* 251082.

50. Brinkman, E. K., Chen, T., Amendola, M., van Steensel, B., 2014. Easy quantitative assessment of genome editing by sequence trace decomposition. *Nucleic Acids Res.* 42(22).

51. Yukselen, O., Turkyilmaz, O., Ozturk, A. R., Garber, M., Kucukural, A., 2020. DolphinNext: a distributed data processing platform for high throughput genomics. *BMC Genomics.* 21(1):310.

52. Bolger, A. M., Lohse, M., & Usadel, B., 2014. Trimmomatic: A flexible trimmer for Illumina Sequence Data. *Bioinformatics.* 30(15):2114-20.

53. Li, B., Dewey, C. N., 2011. RSEM: accurate transcript quantification from RNA-Seq data with or without a reference genome. *BMC Bioinformatics.* 12:323.

54. Love, M I., Huber, W., Anders, S., 2014. Moderated estimation of fold change and dispersion for RNAseq data with DESeq2. *Genome Biology.* 15(12):550.

55. Durinck, S., Spellman, P., Birney, E., Huber, W., 2009. Mapping identifiers for the integration of genomic datasets with the R/Bioconductor package biomaRt. *Nat Protoc.* 4(8):1184-91.

56. Yu, G., Wang, L., Han, Y., He, Q., 2012. clusterProfiler: an R package for comparing biological themes among gene clusters. *OMICS: A Journal of Integrative Biology.* 16(5):284-7.

57. Durinck, S., et al., 2005. BioMart and Bioconductor: a powerful link between biological databases and microarray data analysis. *Bioinformatics.* 21(16):3439-40.

58. Carlson, M., 2019. org.Mm.eg.db: Genome wide annotation for Mouse. R package version 3.8.2.

59. Kucukural, A., et al., 2019. DEBrowser: interactive differential expression analysis and visualization tool for count data. *BMC Genomics.* 20(1):6.

60. Rodriguez, TC., et al., 2021. Genome-wide detection and analysis of CRISPR-Cas off-targets. Reprogramming the Genome: CRISPR-Cas-based Human Disease Therapy, Volume 181.

61. Zhu, L J, et al., 2017. GUIDEseq: a bioconductor package to analyze GUIDE-Seq datasets for CRISPR-Cas nucleases. *BMC genomics.* 18(1):1-0.

62. Clement, K., et al., 2019. CRISPResso2 provides accurate and rapid genome editing sequence analysis. *Nat Biotechnol.* 37(3):224-226.

SEQUENCES

```
Mouse NRIP1 exon 4 (SEQ ID NO: 20):
TACTGACGTGCGTTTGGTGAGCAACGAAAGATGAT

GAAGAAAGAAAACCAGCATATTCCCTGAGACCTGG

GTGCCAGCGCTGCCGCTGTGCTAAGGAAGTTGCGA

GGCTGGCCCTTGCCTAGCCACTCATCAGTGCTGTA

GTCTGCACCCGAGTTTGCCCCAGCCTCTGAGCCCC

TCGTCACTGCCTGAAGATCCCCTGGTCAGAATGTT

AACAGTGCATCTCTGCCCGACTGCTATGGGAGGTG

ATCAGGTGACGCTCACTTCCTGACGTCACGTGGGA

TCTTACTGACGAGAGGAGCTCTTTCACGTGAACGG

AAGCCGAGCCCCTGTGAGCGCTTGTATTGAACATG
```

```
ACTCATGGAGAAGAGCTTGGCTCTGATGTGCATCA
GGATTCTATTGTCTTAACTTACCTCGAAGGGTTAC
TAATGCATCAGGCAGCAGGGGGATCAGGCACTGCC
ATTAACAAAAAGTCTGCTGGCCACAAAGAGGAAGA
CCAGAACTTTAACCTCTCGGGCAGTGCGTTTCCCT
CCTGTCAAAGCAATGGTCCCACTGTCAGTACCCAG
ACGTACCAGGGATCTGGCATGCTGCACCTCAAAAA
AGCCAGACTGCTGCAGTCTTCCGAGGACTGGAACG
CGGCAAAGCGGAAGAGGCTGTCTGATTCCATCGTG
AATTTAAACGTAAAGAAGGAAGCGTTGCTGGCTGG
CATGGTTGACAGTGTGCCTAAAGGCAAACAGGATA
GCACATTGCTGGCCTCTTTGCTTCAGTCATTCAGC
TCTAGGCTGCAGACTGTTGCTCTGTCACAGCAGAT
TAGACAGAGCCTCAAGGAGCAGGGATATGCCCTCA
GTCACGAGTCTTTAAAAGTGGAGAAGGATTTAAGG
TGCTATGGCGTGGCCTCAAGTCACTTAAAAACTCT
GTTGAAGAAAAGTAAAACCAAGGATCAAAAGTCAG
GTCCCACCCTCCCTGACGTGACTCCAAACCTTATC
AGAGATAGCTTTGTTGAGTCATCCCATCCCGCAGT
GGGACAAAGTGGGACAAAGGTCATGAGTGAGCCCT
TGTCATGTGCTGCAAGATTACAGGCTGTTGCCAGC
ATGGTGGAGAAAAGGGCGAGTCCCGCTGCCTCCCC
AAAGCCTAGTGTTGCCTGCAGCCAGTTGGCGCTGC
TCCTGTCCAGCGAGGCCCACCTGCAGCAGTACTCT
CGGGAACATGCTCTAAAAACGCAGAACGCACATCA
GGTGGCAAGCGAAAGACTTGCAGCCATGGCCAGAT
TGCAAGAGAATGGGCAGAAGGACGTGGGCAGTTCG
CAGCTCTCCAAAGGGGTGTCTGGCCATCTCAACGG
GCAGGCCAGAGCACTGCCGGCAAGCAAACTGGTGG
CCAACAAGAATAACGCTGCCACCTTTCAGAGTCCA
ATGGGTGTTGTCCCTTCCTCCCCCAAAAACACGAG
CTATAAGAACTCACTGGAAAGAAACAACCTAAAGC
AGGCTGCTAATAACAGTCTGCTTTTGCATCTCCTC
AAAAGCCAGACCATACCCACGCCGATGAACGGGCA
CAGCCAGAACGAGAGAGCGAGCAGTTTTGAGAGTA
GCACGCCCACCACGATTGATGAGTACTCCGATAAC
AACCCGAGCTTTACAGATGACAGCAGTGGAGACGA
AAGCTCGTACTCCAATTGCGTTCCCATAGACCTGT
CTTGCAAACACCGGATCGAAAAGCCGGAAGCTGAG
CGGCCCGTTTCGCTGGAGAACCTAACCCAGTCCTT
```
```
GTTAAACACGTGGGATCCCAAGATCCCCGGCGTTG
ACATCAAAGAAGATCAAGATACCTCAACAAATTCC
AAGCTGAATTCACACCAGAAAGTCACTCTTCTTCA
GTTGCTGCTCGGCCATAAAAGTGAAGAAACTGTTG
AAAGGAACGCCAGCCCTCAGGACATCCATAGTGAT
GGGACTAAGTTCAGTCCTCAGAATTACACAAGGAC
TTCTGTCATCGAAAGCCCCAGTACCAACAGGACTA
CCCCAGTGAGCACTCCACCACTGTATACAGCCAGC
CAAGCAGAGTCTCCCATCAATCTTTCCCAGCACTC
TCTGGTCATCAAGTGGAATTCCCCGCCGTATGCCT
GCAGTACTCCCGCTTCCAAGCTCACGAACACCGCG
CCTAGCCACCTGATGGACCTCACGAAAGGCAAAGA
GTCCCAAGCCGAGAAACCAGCCCCGAGTGAAGGTG
CACAAAATTCCGCCACGTTCAGTGCCAGTAAACTG
TTACAAAATTTGGCTCAGTGCGGATTGCAGTCTTC
CGGGCCAGGGGAAGAGCAGAGACCCTGCAAACAGC
TGTTAAGTGGAAACCCAGACAAACCTCTCGGTCTG
ATTGATAGATTAAACAGCCCTCTGCTCTCAAATAA
AACCAATGCGGCTGAAGAGAGCAAAGCCTTCAGCA
GTCAGCCTGCCGGGCCTGAGCCGGGACTTCCTGGT
TGTGAGATAGAAAATCTCTTGGAAAGACGGACTGT
CCTTCAGTTGCTCCTGGGAAATTCCAGCAAAGGGA
AGAATGAGAAGAAAGAGAAAACCCCCGCACGAGAC
GAGGCTCCTCAGGAGCATTCGGAGAGGGCTGCAAA
TGAACAGATACTCATGGTGAAGATTAAATCCGAGC
CTTGTGACGACTTCCAGACCCACAACACAAACCTG
CCCTTAAACCACGATGCCAAGAGCGCCCCCTTCTT
AGGTGTGACTCCCGCCATCCACAGGAGCACAGCGG
CCTTACCAGTGTCGGAGGACTTTAAATCCGAGCCT
GCTTCACCTCAGGATTTCTCTTTCTCAAAGAACGG
GCTGTTGAGTCGCTTGCTGAGACAGAATCAAGAGA
GTTACCCGGCAGATGAGCAGGACAAGAGTCACAGA
AACAGTGAGCTGCCAACCCTGGAGTCGAAGAACAT
CTGCATGGTCCCGAAGAAAGGAAGCTGTATACGG
AACCACTGGAGAATCCATTTAAAAAGATGAAAAAT
ACTGCCGTAGATACTGCCAATCATCACAGCGGCCC
GGAAGTACTCTACGGGTCGTTGCTTCATCAGGAAG
AGCTGAAGTTTAGCAGGAATGAGCTCGATTATAAA
TACCCTGCTGGGCATAGTTCAGCCAGCGATGGTGA
CCACAGGAGTTGGGCCAGAGAGAGCAAAAGCTTCA
ATGTTCTCAAGCAGCTGCTGCTCTCCGAGAACTGT
```

-continued

GTGCGAGATCTGTCCCCACACAGGAGTGACTCTGT

CCCCGACACGAAAAAGAAAGGACACAAAAACAACG

CGCCCGGCAGCAAACCTGAATTCGGCATTTCTTCT

TTAAATGGACTGATGTATAGTTCCCCGCAGCCTGG

CAGTTGTGTGACGGATCATAGGACATTTTCATACC

CGGGAATGGTAAAGACCCCTCTGAGCCCTCCTTTC

CCAGAGCACTTGGGCTGTGTGGGGTCCAGACCAGA

ACCTGGGCTTTTGAATGGATGTTCCGTGCCCGGTG

AGAAGGGACCCATTAAGTGGGTCATCGCAGATATG

GATAAGAATGAATACGAAAAGACTCTCCAAGACT

GACCAAAACTAATCCGATCCTCTATTACATGCTCC

AGAAGGGAGGGGCAATTCTGTTACCACACAAGAA

ACCCAGGACAAAGACATCTGGAGGGAGCCTGCGTC

AGCCGAGAGTCTCTCACAGGTTACAGTCAAAGAAG

AGCTACTTCCCGCTGCAGAAACTAAAGCTTCTTTC

TTTAATCTAAGAAGCCCGTACAATAGCCATATGGG

AAATAATGCTTCTCGCCCACACAGTACAAATGGAG

AAGTGTATGGACTTCTGGGAAACGCGCTCACCATA

AAAAAGAGTCAGAATAAATGTGTACCTGCCATAC

CACTTTGGGTCTTTTTAAAATTTAGTCAGTATGAA

CTTGAGATCTGTATAAATAAGAGCATGATTTGAGA

AAAGCATGGTATAACTGAAACTCCTTCCTTTTGAA

AGTATTGGTCACTGGTGATGTTTAAATATGCATAC

TAATTTTTGCTTAACATTAGATGTCATGAGGAAAC

AATTGAACTCGAGGTTGGTTGTTTACTATTTCTGT

ATGCATCAGATAACAACTGTGACTAGCCTACGAAT

GAACCTGTTTTTATAATCGTAAATAAGAGGCATAC

ATTAAAATGCACAACTTCACCAG

Human INTUP1 exon 4 (SEQ ID NO: 21):
ACACTGATATTTGCATTTAATGGGGAACAAAAGAT

GAAGAAGGAAAAGGAATATATTCACTAAGGATTCT

ATCTGCTTACTGCTACAGACCTATGTGTTAAGGAA

TTCTTCTCCTCCTCCTTGCGTAGAAGTTGATCAGC

ACTGTGGTCAGACTGCATTTATCTTGTCATTGCCA

GAAGAAATCTTGGACAGAATGTAACAGTACGTCTC

TCTCTGATTGCGATGGAAGGTGATAAACTGATACT

CCTTTATTAAAGTTACATCGCACTCACCACAGAAA

ACCATTCTTTAAAGTGAATAGAAACCAAGCCCTTG

TGAACACTTCTATTGAACATGACTCATGGAGAAGA

GCTTGGCTCTGATGTGCACCAGGATTCTATTGTTT

TAACTTACCTAGAAGGATTACTAATGCATCAGGCA

-continued

GCAGGGGATCAGGTACTGCCGTTGACAAAAAGTC

TGCTGGGCATAATGAAGAGGATCAGAACTTTAACA

TTTCTGGCAGTGCATTTCCCACCTGTCAAAGTAAT

GGTCCAGTTCTAATACACATACATATCAGGGGTC

TGGCATGCTGCACCTCAAAAAAGCCAGACTGTTGC

AGTCTTCTGAGGACTGGAATGCAGCAAAGCGGAAG

AGGCTGTCTGATTCTATCATGAATTTAAACGTAAA

GAAGGAAGCTTTGCTAGCTGGCATGGTTGACAGTG

TGCCTAAAGGCAAACAGGATAGCACATTACTGGCC

TCTTTGCTTCAGTCATTCAGCTCTAGGCTGCAGAC

TGTTGCTCTGTCACAACAAATCAGGCAGAGCCTCA

AGGAGCAAGGATATGCCCTCAGTCATGATTCTTTA

AAAGTGGAGAAGGATTTAAGGTGCTATGGTGTTGC

ATCAAGTCACTTAAAAACTTTGTTGAAGAAAAGTA

AAGTTAAAGATCAAAAGCCTGATACGAATCTTCCT

GATGTGACTAAAAACCTCATCAGAGATAGGTTTGC

AGAGTCTCCTCATCATGTTGGACAAAGTGGAACAA

AGGTCATGAGTGAACCGTTGTCATGTGCTGCAAGA

TTACAGGCTGTTGCAAGCATGGTGGAAAAAAGGGC

TAGTCCTGCCACCTCACCTAAACCTAGTGTTGCTT

GTAGCCAGTTAGCATTACTTCTGTCAAGCGAAGCC

CATTTGCAGCAGTATTCTCGAGAACACGCTTTAAA

AACGCAAAATGCAAATCAAGCAGCAAGTGAAAGAC

TTGCTGCTATGGCCAGATTGCAAGAAAATGGCCAG

AAGGATGTTGGCAGTTACCAGCTCCCAAAAGGAAT

GTCAAGCCATCTTAATGGTCAGGCAAGAACATCAT

CAAGCAAACTGATGGCTAGCAAAAGTAGTGCTACA

GTGTTTCAAAATCCAATGGGTATCATTCCTTCTTC

CCCTAAAAATGCAGGTTATAAGAACTCACTGGAAA

GAAACAATATAAAACAAGCTGCTAACAATAGTTTG

CTTTTACATCTTCTTAAAAGCCAGACTATACCTAA

GCCAATGAATGGACACAGTCACAGTGAGAGAGGAA

GCATTTTGAGGAAAGTAGTACACCTACAACTATT

GATGAATATTCAGATAACAATCCTAGTTTTACAGA

TGACAGCAGTGGTGATGAAAGTTCTTATTCCAACT

GTGTTCCCATAGACTTGTCTTGCAAACACCGAACT

GAAAAATCAGAATCTGACCAACCTGTTTCCCTGGA

TAACTTCACTCAATCCTTGCTAAACACTTGGGATC

CAAAAGTCCCAGATGTAGATATCAAAGAAGATCAA

GATACCTCAAAGAATTCTAAGCTAAACTCACACCA

```
GAAAGTAACACTTCTTCAATTGCTACTTGGCCATA

AGAATGAAGAAAATGTAGAAAAAAACACCAGCCCT

CAGGGAGTACACAATGATGTGAGCAAGTTCAATAC

ACAAAATTATGCAAGGACTTCTGTGATAGAAAGCC

CCAGTACAAATCGGACTACTCCAGTGAGCACTCCA

CCTTTACTTACATCAAGCAAAGCAGGGTCTCCCAT

CAATCTCTCTCAACACTCTCTGGTCATCAAATGGA

ATTCCCCACCATATGTCTGCAGTACTCAGTCTGAA

AAGCTAACAAATACTGCATCTAACCACTCAATGGA

CCTTACAAAAAGCAAAGACCCACCAGGAGAGAAAC

CAGCCCAAAATGAAGGTGCACAGAACTCTGCAACG

TTTAGTGCCAGTAAGCTGTTACAAAATTTAGCACA

ATGTGGAATGCAGTCATCCATGTCAGTGGAAGAGC

AGAGACCCAGCAAACAGCTGTTAACTGGAAACACA

GATAAACCGATAGGTATGATTGATAGATTAAATAG

CCCTTTGCTCTCAAATAAAACAAATGCAGTTGAAG

AAAATAAAGCATTTAGTAGTCAACCAACAGGTCCT

GAACCAGGGCTTTCTGGTTCTGAAATAGAAAATCT

GCTTGAAAGACGTACTGTCCTCCAGTTGCTCCTGG

GGAACCCCAACAAAGGGAAGAGTGAAAAAAAAGAG

AAAACTCCCTTAAGAGATGAAAGTACTCAGGAACA

CTCAGAGAGAGCTTTAAGTGAACAAATACTGATGG

TGAAAATAAAATCTGAGCCTTGTGATGACTTACAA

ATTCCTAACACAAATGTGCACTTGAGCCATGATGC

TAAGAGTGCCCCATTCTTGGGTATGGCTCCTGCTG

TGCAGAGAAGCGCACCTGCCTTACCAGTGTCCGAA

GACTTTAAATCGGAGCCTGTTTCACCTCAGGATTT

TTCTTTCTCCAAGAATGGTCTGCTAAGTCGATTGC

TAAGACAAAATCAAGATAGTTACCTGGCAGATGAT

TCAGACAGGAGTCACAGAAATAATGAAATGGCACT

TCTAGAATCAAAGAATCTTTGCATGGTCCCTAAGA

AAAGGAAGCTTTATACTGAGCCATTAGAAAATCCA

TTTAAAAAGATGAAAAACAACATTGTTGATGCTGC

AAACAATCACAGTGCCCCAGAAGTACTGTATGGGT

CCTTGCTTAACCAGGAAGAGCTGAAATTTAGCAGA

AATGATCTTGAATTTAAATATCCTGCTGGTCATGG

CTCAGCCAGCGAAAGTGAACACAGGAGTTGGGCCA

GAGAGAGCAAAAGCTTTAATGTTCTGAAACAGCTG

CTTCTCTCAGAAAACTGTGTGCGAGATTGTCCCC

GCACAGAAGTAACTCTGTGGCTGACAGTAAAAAGA

AAGGACACAAAAATAATGTGACCAACAGCAAACCT

GAATTTAGCATTTCTTCTTTAAATGGACTGATGTA

CAGTTCCACTCAGCCCAGCAGTTGCATGGATAACA

GGACATTTTCATACCCAGGTGTAGTAAAAACTCCT

GTGAGTCCTACTTTCCCTGAGCACTTGGGCTGTGC

AGGGTCTAGACCAGAATCTGGGCTTTTGAATGGGT

GTTCCATGCCCAGTGAGAAAGGACCCATTAAGTGG

GTTATCACTGATGCGGAGAAGAATGAGTATGAAAA

AGACTCTCCAAGATTGACCAAAACCAACCCAATAC

TATATTACATGCTTCAAAAAGGAGGCAATTCTGTT

ACCAGTCGAGAAACACAAGACAAGGACATTTGGAG

GGAGGCTTCATCTGCTGAAAGTGTCTCACAGGTCA

CAGCCAAAGAAGAGTTACTTCCTACTGCAGAAACG

AAAGCTTCTTTCTTTAATTTAAGAAGCCCTTACAA

TAGCCATATGGGAAATAATGCTTCTCGCCCACACA

GCGCAAATGGAGAAGTTTATGGACTTCTGGGAAGC

GTGCTAACGATAAAGAAAGAATCAGAATAAAATGT

ACCTGCCATCCAGTTTTGGATCTTTTTAAAACTAA

TGAGTATGAACTTGAGATCTGTATAAATAAGAGCA

TGATTTGAAAAAAAGCATGGTATAATTGAAACTTT

TTTCATTTTGAAAAGTATTGGTTACTGGTGATGTT

GAAATATGCATACTAATTTTTGCTTAACATTAGAT

GTCATGAGGAAACTACTGAACTAGCAATTGGTTGT

TTAACACTTCTGTATGCATCAGATAACAACTGTGA

GTAGCCTATGAATGAAATTCTTTTATAAATATTAG

GCATAAATTAAAATGTAAAACTCCATTCATAGTGG

ATTAATGCATTTTGCTGCCTTTATTAGGGTACTTT

ATTTTGCTTTTCAGAAGTCAGCCTACATAACACAT

TTTTAAAGTCTAAACTGTTAAACAACTCTTTAAAG

GATAATTATCCAATAAAAAAAAACCTAGTGCTGAT

TCACAGCTTATTATCCAATTCAAAAATAAATTAGA

AAAATATATGCTTACATTTTTCACTTTTGCTAAAA

AGAAAAAAAAAGGTGTTTATTTTTAACTCTTGGA

AGAGGTTTTGTGGTTCCCAATGTGTCTGTCCCACC

CTGATCCTTTTCAATATATATTTCTTTAAACCTTG

TGCTACTTAGTAAAAATTGATTACAATTGAGGGAA

GTTTGATAGATCCTTTAAAAAAAAGGCAGATTTCC

ATTTTTTGTATTTTAACTACTTTACTAAAATTAATA

CTCCTCCTTTTACAGAATTAGAAAAGTTAACATTT

ATCTTTAGGTGGTTTCCTGAAAAGTTGAATATTTA

AGAAATTGTTTTTAACAGAAGCAAAATGGCTTTTC
```

```
TTTGGACAGTTTTCACCATCTCTTGTAAAAGTTAA
TTCTCACCATTCCTGTGGTACCTGCGAGTGTTATG
ACCAGGATTCCTTAAACCTGAACTCAGACCACTTG
CATTAGAACCATCTGGAGCACTTGTTTTAAAATGC
AGATTCATAGGCAGCATCTCAGATCTACAGAACAA
GAATCTCTGCTAAGTGGACCTGGAATCTTCCATCT
GCATCTTAACATGCTCTCTAGGTGTTTCTTGTGTT
TGAGAACCATGACTTATGACTTTCCTCAGAACATG
AGACTGTAAAACAAAAACAAAAAACTATGTGATGC
CTCTATTTTCCCCAATACAGTCACACATCAGCTCA
AAATTTGCAATATTGTAGTTCATATATTACCGTTA
TGTCTTTGGAAATCGGGTTCAGAACACTTTTTATG
ACAAAAATTGGGTGGAGGGGATAACTTTCATATCT
GGCTCAACATCTCAGGAAAATCTGTGATTATTTGT
GTGTTCTAATGAGTAACATCTACTTAGTTAGCCTT
AGGGATGGAAAAACAGGGCCACTTACCAAACTCAG
GTGATTCCAGGATGGTTTGGAAACTTCTCCTGAAT
GCATCCTTAACCTTTATTAAAACCATTGTCCTAAG
AACAATGCCAACAAAGCTTACAACATTTAGTTTAA
ACCCAAGAAGGGCACTAAACTCAGATTGACTAAAT
AAAAAGTACAAAGGGCACATATACGTGACAGAATT
GTACACAATCACTCCATTGGATCTTTTACTTTAAA
GTAGTGATGAAAAGTACATGTTGATACTGTCTTAG
AAGAAATTAATATATTAGTGAAGCCACATGGGGTT
TCAGTTGCGAAACAGGTCTGTTTTTATGTTCAGTT
TGTACAATCCACAATTCATTCACCAGATATTTTGT
TCTTAATTGTGAACCAGGTTAGCAAATGACCTATC
AAAAATTATTCTATAATCACTACTAGTTAGGATAT
TGATTTAAAATTGTTCTACTTGAAGTGGTTTCTAA
GATTTTATATTAAAAATAGGTGTGATTTCCTAAT
ATGATCTAAAACCCTAAATGGTTATTTTTCCTCAG
AATGATTTGTAAATAGCTACTGGAAATATTATACA
GTAATAGGAGTGGGTATTATGCAACATCATGGAGA
AGTGAAGGCATAGGCTTATTCTGACATAAAATTCC
ACTGGCCAGTTGAATATATTCTATTCCATGTCCAT
ACTATGACAATCTTATTGTCAACACTATATAAATA
AGCTTTTAAACAAGTCATTTTCTTGATCGTTGTG
GAAGGTTTGGAGCCTTAGAGGTATGTCAGAAAAAA
TATGTTGGTATTCTCCCTTGGGTAGGGGAAATGA
CCTTTTTACAAGAGAGTGAAATTTAGGTCAGGGAA
AAGACCAAGGGCCAGCATTGCTACTTTTGTGTGTG
TGTGTGTGGGTTTTGTTTTGTTTTTTTGGTTGGCT
GGTTGTTTTCGTTGTTGTTAACAAAGGAATGAGAA
TATGTAATACTTAAATAAACATGACCACGAAGAAT
GCTGTTCTGATTTACTAGAGAATGTTCCCAATTTG
AATTTAGGGTGATTTTAAAGAACAGTGAGAAAGGG
CATACATCCACAGATTCACTTTGTTTATGCATATG
TAGATACAAGGATGCACATATACACATTTTCAAGG
ACTATTTTAGATATCTAGACAATTTCTTCTAATAA
AGTCATTTGTGAAAGGGTACTACAGCTTATTGACA
TCAGTAAGGTAGCATTCATTACCTGTTTATTCTCT
GCTGCATCTTACAGAAGAGTAAACTGGTGAGAGTA
TATATTTATATATATATATATATATATATATATA
ATATGTATATATATATATATTGACTTGTTACATGA
AGATGTTAAAATCGGTTTTTAAAGGTGATGTAAAT
AGTGATTTCCTTAATGAAAAATACATATTTTGTAT
TGTTCTAATGCAACAGAAAAGCCTTTTAATCTCTT
TGGTTCCTGTATATTCCATGTATAAGTGTAAATAT
AATCAGACAGGTTTAAAAGTTGTGCATGTATGTAT
ACAGTTGCAAGTCTGGACAAATGTATAGAATAAAC
CTTTTATTTAAGTTGTGATTACCTGCTGCATGAAA
AGTGCATGGGGACCCTGTGCATCTGTGCATTTGG
CAAAATGTCTTAACAAATCAGATCAGATGTTCATC
CTAACATGACAGTATTCCATTTCTGGACATGACGT
CTGTGGTTTAAGCTTTGTGAAAGAATGTGCTTTGA
TTCGAAGGGTCTTAAAGAATTTTTTTAATCGTCAA
CCACTTTTAAACATAAAGAATTCACACAACTACTT
TCATGAATTTTTTAATCCCATTGCAAACATTATTC
CAAGAGTATCCCAGTATTAGCAATACTGGAATATA
GGCACATTACCATTCATAGTAAGAATTCTGGTGTT
TACACAACCAAATTTGATGCGATCTGCTCAGTAAT
ATAATTTGCCATTTTTATTAGAAATTTAATTTCTT
CATGTGATGTCATGAAACTGTACATACTGCAGTGT
GAATTTTTTGTTTTGTTTTTAATCTTTTAGTGT
TTACTTCCTGCAGTGAATTTGAATAAATGAGAAAA
AATGCATTGTC
```

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising an RNA-guided nuclease (RGN) and a guide RNA (gRNA), wherein the gRNA comprises a target sequence within exon 4 of a human nuclear receptor interacting protein 1 (Nrip1) gene, and wherein the gRNA comprises the sequence of SEQ ID NO: 16, SEQ ID NO: 17, or SEQ ID NO: 18.

2. The composition of claim 1, wherein the gRNA comprises a modification.

3. A method of making a population of mature adipose cells, the method comprising:
   obtaining a population of adipose progenitor cells,
   introducing into the population of adipose progenitor cells the composition of claim 1 to produce a population of adipose progenitor cells comprising a disrupted Nrip1 gene, and
   maintaining the population of adipose progenitor cells comprising the disrupted Nrip1 gene in culture under conditions sufficient to induce differentiation of the adipose progenitor cells into mature adipose cells comprising the disrupted Nrip1 gene.

4. The method of claim 3, wherein the adipose progenitor cells are Human Adipose Capillary Progenitor Cells (HACAPS) or primary adipose progenitor cells.

5. The method of claim 3, wherein the mature adipose cells are white, brite, or brown adipose cells.

6. The method of claim 3, wherein the conditions sufficient to induce differentiation comprise maintaining the adipose progenitor cells in culture in the presence of adenylate cyclase activators or adrenergic agonists to induce differentiation of the adipose progenitor cells into brite adipose cells.

7. The method of claim 3, wherein the RGN and gRNA are delivered to the progenitor cells as a ribonucleoprotein (RNP) complex.

8. The method of claim 7, wherein the RNP complex comprises *Streptococcus pyogenes* Cas9 (SpCas9) and the gRNA.

9. The method of claim 7, wherein the RNP complex is delivered to the adipose progenitor cells by electroporation.

10. The population of mature adipose cells produced by the method of claim 3.

* * * * *